US009107926B2

(12) United States Patent
Belvin et al.

(10) Patent No.: US 9,107,926 B2
(45) Date of Patent: Aug. 18, 2015

(54) MUTANT SELECTIVITY AND COMBINATIONS OF A PHOSPHOINOSITIDE 3-KINASE INHIBITOR COMPOUND AND CHEMOTHERAPEUTIC AGENTS FOR THE TREATMENT OF CANCER

(71) Applicant: Genentech, Inc., South San Francisco, CA (US)

(72) Inventors: Marcia Belvin, Albany, CA (US); Lori Friedman, San Carlos, CA (US); Deepak Sampath, San Francisco, CA (US); Jeffrey Wallin, Berkeley, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days.

(21) Appl. No.: 13/912,281

(22) Filed: Jun. 7, 2013

(65) Prior Publication Data
US 2014/0044706 A1 Feb. 13, 2014

Related U.S. Application Data

(60) Provisional application No. 61/657,484, filed on Jun. 8, 2012, provisional application No. 61/808,727, filed on Apr. 5, 2013.

(51) Int. Cl.
*C07D 498/00* (2006.01)
*C07D 513/00* (2006.01)
(Continued)

(52) U.S. Cl.
CPC ............ *A61K 31/553* (2013.01); *A61K 31/138* (2013.01); *A61K 31/337* (2013.01);
(Continued)

(58) Field of Classification Search
None
See application file for complete search history.

(56) References Cited

U.S. PATENT DOCUMENTS 5,824,492 A   10/1998   Hiles et al.
5,846,824 A   12/1998   Hiles et al.
(Continued)

FOREIGN PATENT DOCUMENTS

WO   2009/103790 A2   8/2009
WO   2011/036280 A1   3/2011

OTHER PUBLICATIONS

Sabnis et al. Inhibition of phosphatidylinositol 3-kinase/ AKT pathway improves response of long-term estrogen-deprived breast cancer xenografts to antiestrogens. Clin. Cancer Res. 2007; 13: 2751-2757.*
(Continued)

*Primary Examiner* — Anna Pagonakis
(74) *Attorney, Agent, or Firm* — Alex Andrus; Genetech, Inc.

(57) ABSTRACT

Methods and compositions are provided for treating hyperproliferative disorders in patients with a PI3K inhibitor, GDC-0032 as a single agent or in combination with chemotherapeutic agents.

11 Claims, 38 Drawing Sheets

(51) Int. Cl.

| | | |
|---|---|---|
| A61K 31/553 | (2006.01) | |
| A61K 39/395 | (2006.01) | |
| A61K 45/06 | (2006.01) | |
| A61K 31/138 | (2006.01) | |
| A61K 31/337 | (2006.01) | |
| A61K 31/357 | (2006.01) | |
| A61K 31/4196 | (2006.01) | |
| A61K 31/437 | (2006.01) | |
| A61K 31/4523 | (2006.01) | |
| A61K 31/513 | (2006.01) | |
| A61K 31/555 | (2006.01) | |
| A61K 31/565 | (2006.01) | |
| A61K 31/573 | (2006.01) | |
| A61K 31/7068 | (2006.01) | |
| G01N 33/50 | (2006.01) | |
| C12Q 1/68 | (2006.01) | |
| C07K 16/32 | (2006.01) | |

(52) U.S. Cl.
CPC ........... *A61K31/357* (2013.01); *A61K 31/4196* (2013.01); *A61K 31/437* (2013.01); *A61K 31/4523* (2013.01); *A61K 31/513* (2013.01); *A61K 31/555* (2013.01); *A61K 31/565* (2013.01); *A61K 31/573* (2013.01); *A61K 31/7068* (2013.01); *A61K 39/39558* (2013.01); *A61K 45/06* (2013.01); *C12Q 1/6886* (2013.01); *G01N 33/5011* (2013.01); *G01N 33/5023* (2013.01); *C07K 16/32* (2013.01); *C12Q 2600/106* (2013.01); *C12Q 2600/136* (2013.01); *C12Q 2600/142* (2013.01); *C12Q 2600/156* (2013.01); *C12Q 2600/158* (2013.01)

(56) References Cited

U.S. PATENT DOCUMENTS

| | | | |
|---|---|---|---|
| 6,274,327 | B1 | 8/2001 | Hiles et al. |
| 7,781,433 | B2 | 8/2010 | Chuckowree et al. |
| 8,242,104 | B2 | 8/2012 | Blaquiere et al. |
| 8,247,397 | B2 | 8/2012 | Belvin et al. |
| 8,263,633 | B2 | 9/2012 | Blaquiere et al. |
| 8,324,206 | B2 | 12/2012 | Chuckowree et al. |
| 8,343,955 | B2 | 1/2013 | Blaquiere et al. |
| 8,536,161 | B2 | 9/2013 | Ebens et al. |

OTHER PUBLICATIONS

Miller et al. Hyperactivation of phosphatdiylinositol-3 kinase promotes escape from hormone dependence in estrogen receptor-positive human breast cancer. The Journal of Clinical Investigation. vol. 120, No. 7, Jul. 2010.*

Chou and Talalay, "Quantitative analysis of dose-effect relationships; the combined effects of multiple drugs or enzyme inhibitors" Adv Enzyme Regul. 22:27-55 ( 1984).

Friedman et al., "Selective PI3K and dual Pl3K/mTOR inhibitors enhance the efficacy of endocrine therapies in breast cancer models" Cancer Research—AACR San Antonio Breast Cancer Symposium (Abstract), 72(24 SUPPL 3) (Dec. 4-8, 2012)

Higgins et al., "Antitumor activity of erlotinib (OSI-774, Tarceva) alone or in combination in human non-small cell lung cancer tumor xenograft models" Anti-Cancer Drugs 15:503-512 (2004).

Janku et al., "PIK3CA Mutations in Patients with Advanced Cancers Treated with PI3K/AKT/mTOR Axis Inhibitors" Mol Cancer Ther 10(3):558-65 ( 2011).

Miller et al., "Phosphatidylinositol 3-Kinase and Antiestrogen Resistance in Breast Cancer" J Clin Oncol 29:4452-4461 ( 2011).

Ndubaku et al., "Discovery of 2-{3-[2-(1-Isopropyl-3-methyl-1H-1,2-4-triazol-5-yl)-5,6-dihydrobenzo[f]imidazo[1,2-d][1,4]oxazepin-9-yl]-1H-pyrazol-1-yl}-2-methylpropanamide (GDC-0032): A β-Sparing Phosphoinositide 3-Kinase Inhibitor with High Unbound Exposure and Robust in Vivo Antitumor Activity" J. Med. Chem. 56:4597-4610 ( 2013)

O'Shaughnessy et al., "Capecitabine/Taxane Combination Therapy: Evolving Clinical Utility in Breast Cancer" Clinical Breast Cancer 7(1):42-50 ( 2006).

Ouchi et al., "Antitumor activity of erlotinib in combination with capecitabine in human tumor xenograft models" Cancer Chemother. Pharmacol. 57:693-702 ( 2006).

Samuels et al., "High frequency of mutations of the PIK3CA gene in human cancers" Science 304:554 (Apr. 23, 2004).

Sawada et al., "Induction of thymidine phosphorylase activity and enhancement of capecitabine efficacy by taxol/taxotere in human cancer xenografts" Clin. Cancer Res. 4:1013-19 ( 1998).

She et al., "Breast Tumor Cells with PI3K Mutation or HER2 Amplification Are Selectively Addicted to Akt Signaling" PLoS ONE 3(8):1-10 ( 2008).

Spoerke et al., "Phosphoinositide 3-Kinase (PI3K) Pathway Alterations Are Associated with Histologic Subtypes and Are Predictive of Sensitivity to PI3K Inhibitors in Lung Cancer Preclinical Models" Clin Cancer Res 18:6771-83 ( 2012).

Staben et al., "Discovery of thiazolobenzoxepin PI3-kinase inhibitors that spare the PI3-kinase β Isoform" Bioorganic and Medicinal Chemistry Letters 23(9):2606-13 (May 1, 2013).

Steinbach et al., "Combination and Sequential Antifungal Therapy for Invasive Aspergillosis: Review of Published In Vitro and In Vivo Interactions and 6281 Clinical Cases from 1966 to 2001" Clin. Inf. Dis. 37( SUPPL 3):S188-224 (Oct. 1, 2003).

Sutherlin et al., "Discovery of a potent, selective, and orally available class I phosphatidylinositol 3-kinase (PI3K)/mammalian target of rapamycin (mTOR) kinase inhibitor (GDC-0980) for the treatment of cancer" J Med Chem. 54(21):7579-87 ( 2011).

Vadas, "Structural Basis for Activation and Inhibition of Class I Phosphoinositide 3-Kinases" Science Signaling 4(195):1-12 ( 2011).

Wallin et al., "GDC-0941, a Novel Class I Selective PI3K Inhibitor, Enhances the Efficacy of Docetaxel in Human Breast Cancer Models by Increasing Cell Death In Vitro and In Vivo" Clin Cancer Res 18:3901-11 ( 2012).

Wallin et al., "GDC-0980 is a novel class I PI3K/mTOR kinase inhibitor with robust activity in cancer models driven by the PI3K pathway" Mol Cancer Ther. 10(12):2426-36 ( 2011).

Wallin et al., "Nuclear Phospho-Akt Increase Predicts Synergy of PI3K Inhibition and Doxorubicin in Breast and Ovarian Cancer" Sci Transl Med 2:48ra66 ( 2010).

Weigelt et al., "PIK3CA mutation, but not PTEN loss of functionm, determines the sensitivity of breast cancer cells to mTOR inhibitory drugs," Oncogene 30:3222-33 ( 2011).

Juric et al., "Phase Ib Study of the PI3K Inhibitor GDC-0032 in Combination with Fulvestrant in Patients with Hormone Receptor-Positive Advanced Breast Cancer" ((SABCS 2013)).

* cited by examiner

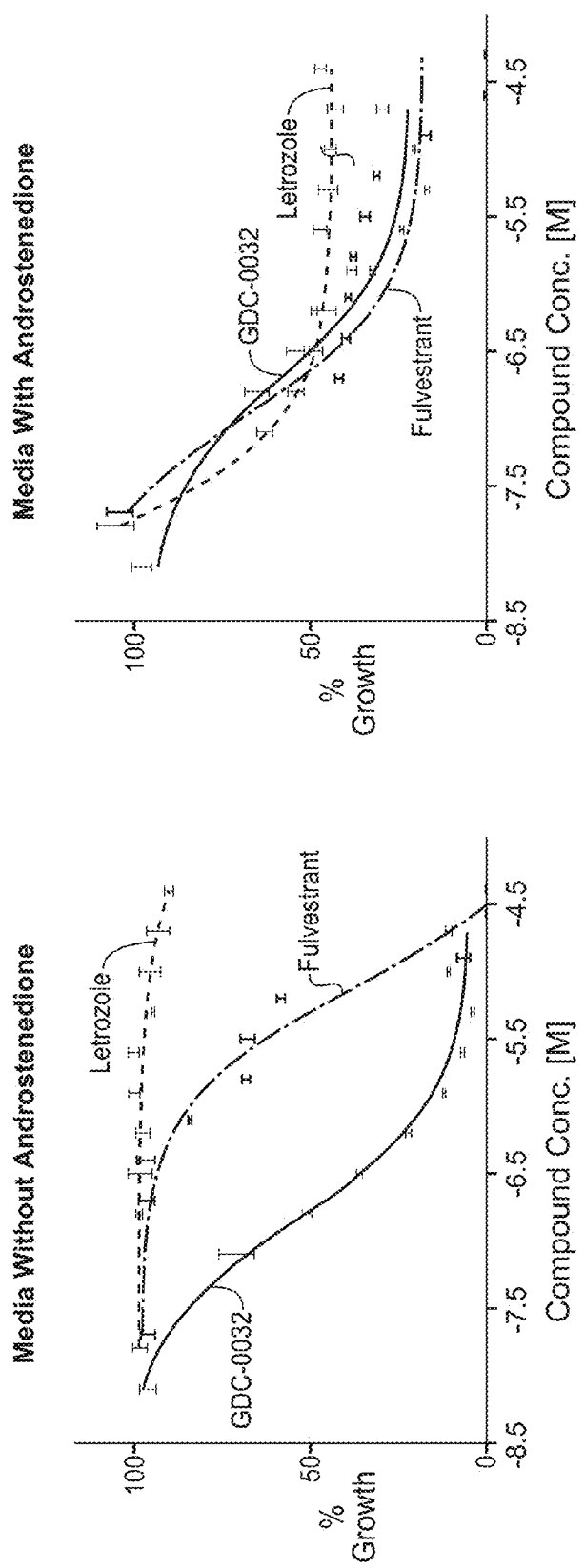

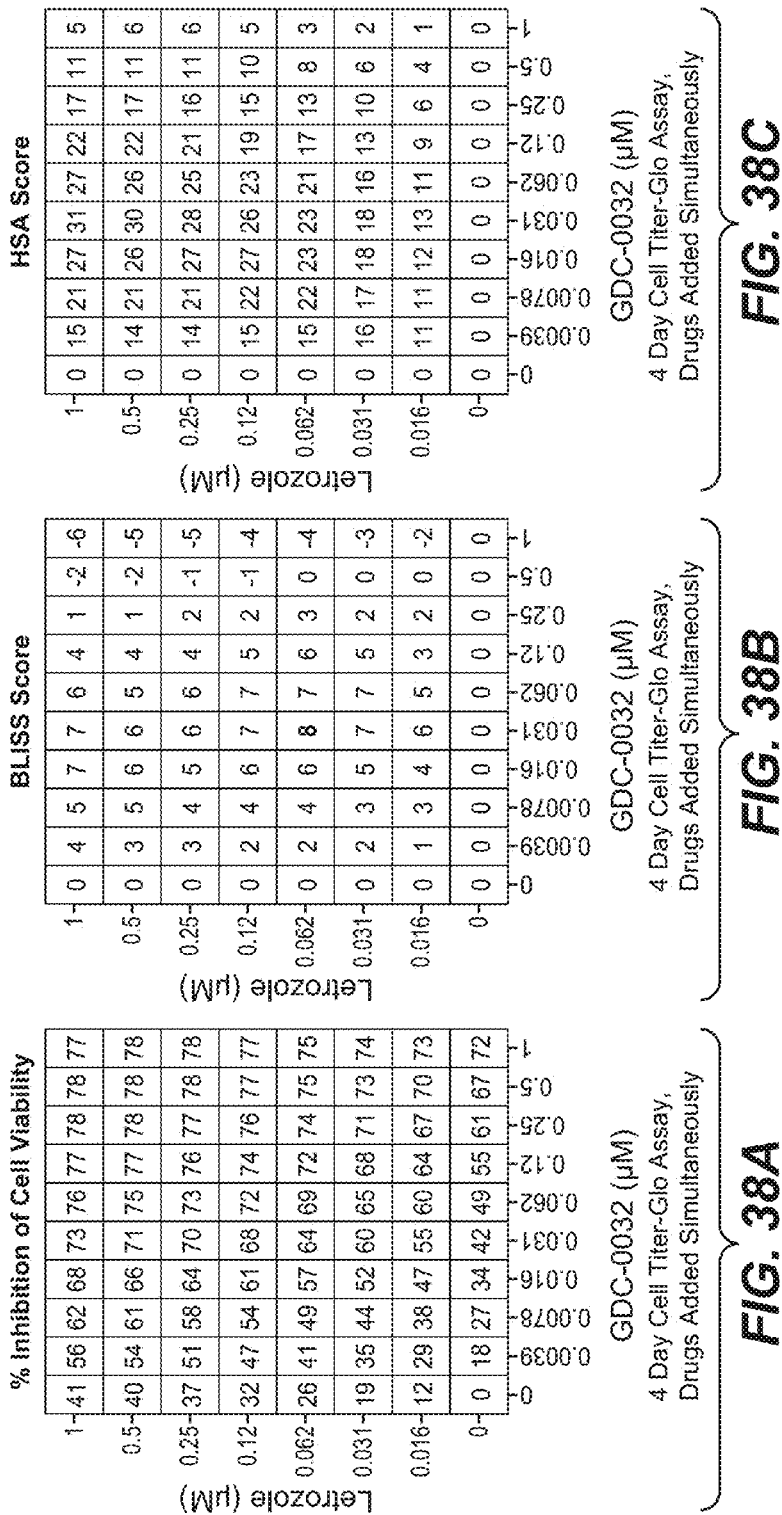

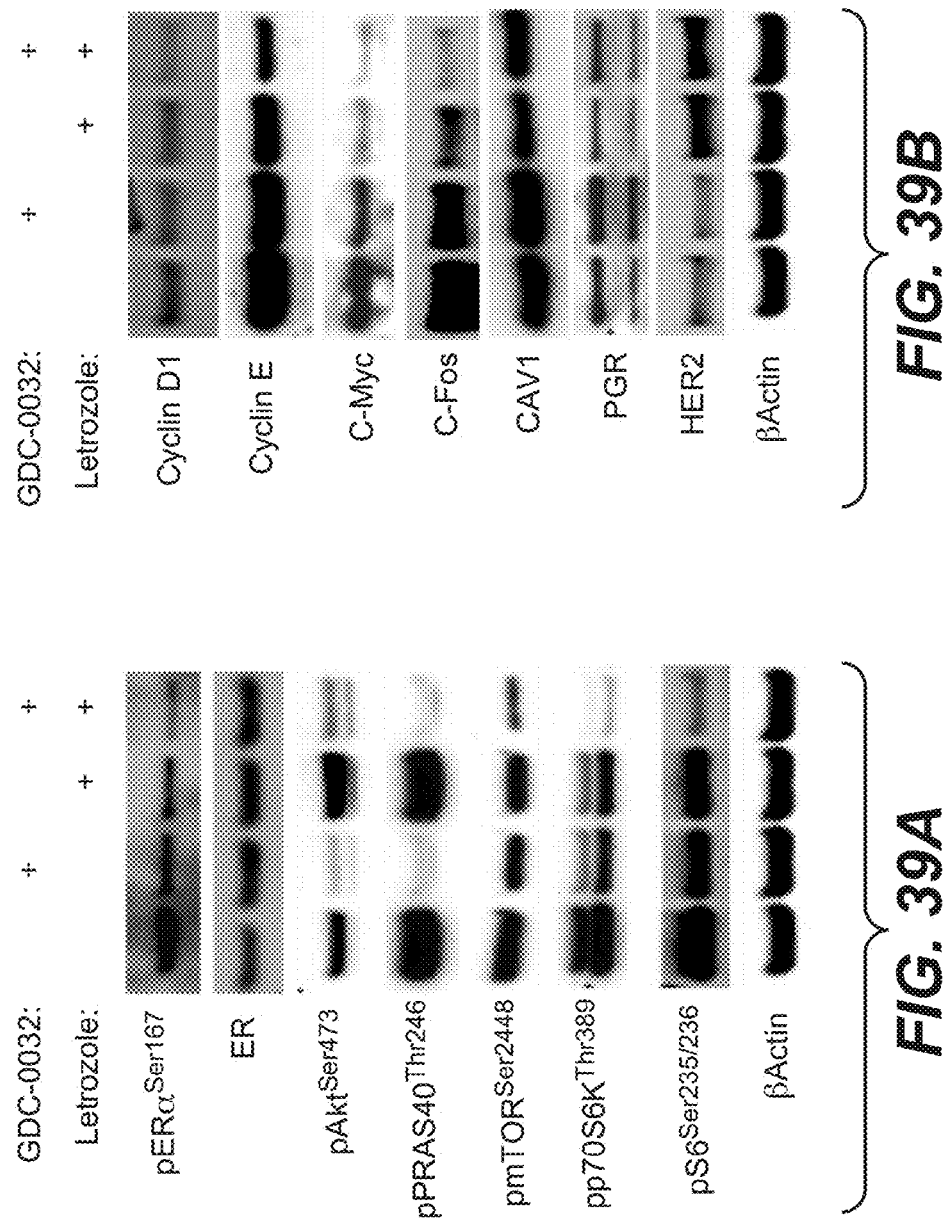

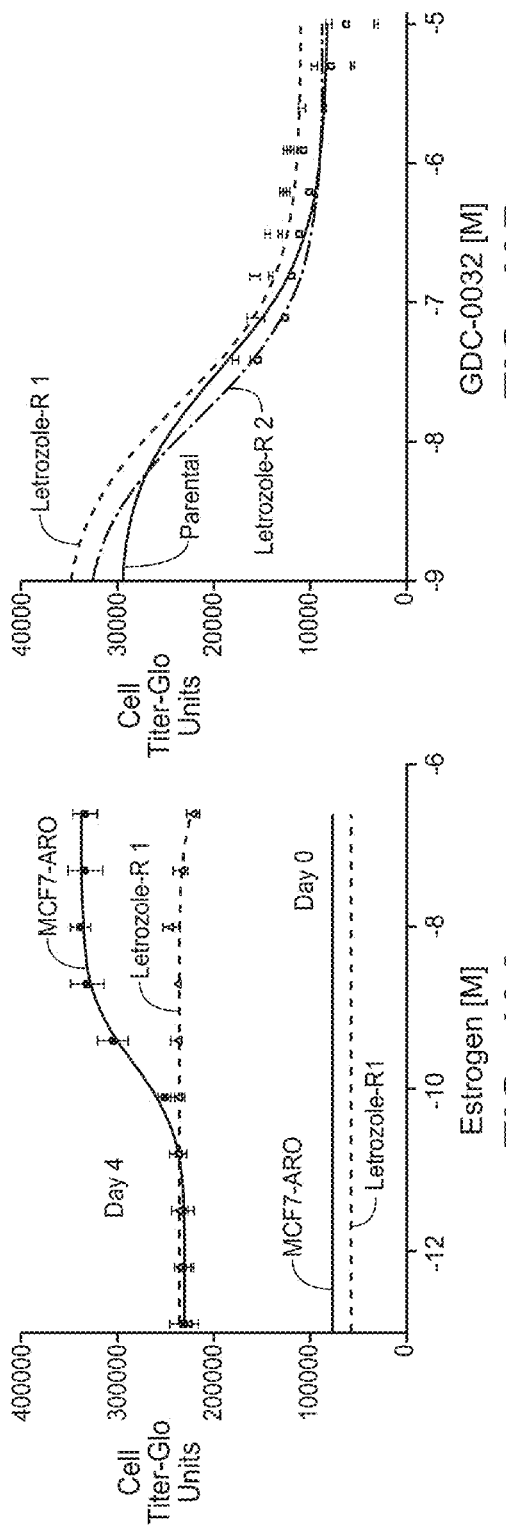
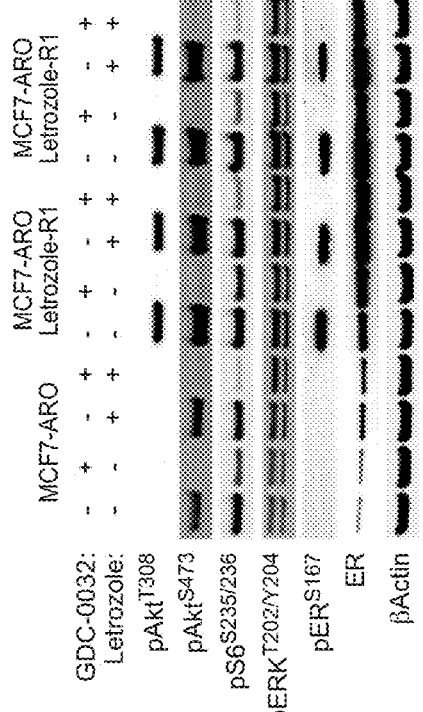
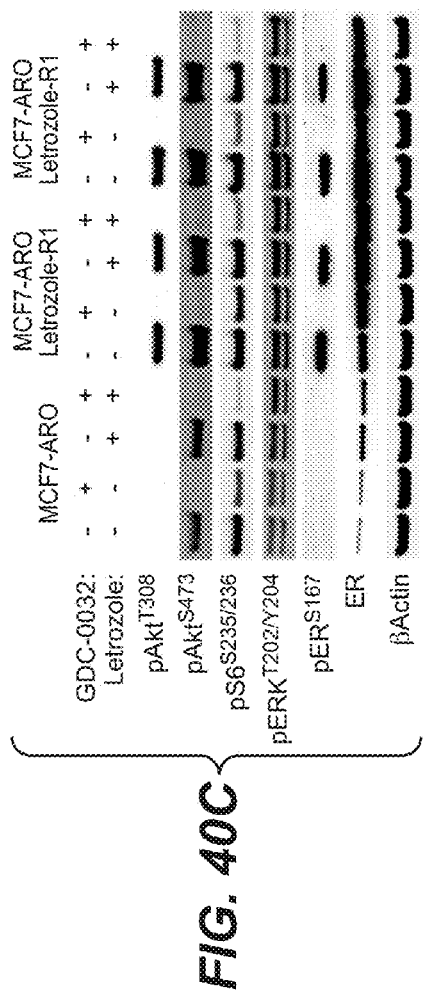
FIG. 40A
FIG. 40B
FIG. 40C

MUTANT SELECTIVITY AND COMBINATIONS OF A PHOSPHOINOSITIDE 3-KINASE INHIBITOR COMPOUND AND CHEMOTHERAPEUTIC AGENTS FOR THE TREATMENT OF CANCER

CROSS REFERENCE TO RELATED APPLICATIONS

This non-provisional application filed under 37 CFR §1.53 (b), claims the benefit under 35 USC §119(e) of U.S. Provisional Application Ser. No. 61/657,484 filed on 8 Jun. 2012 and U.S. Provisional Application Ser. No. 61/808,727 filed on 5 Apr. 2013, which are incorporated by reference in their entirety.

FIELD OF THE INVENTION

The invention relates generally to treatment of hyperproliferative disorders such as cancer with compounds that inhibit PI3 kinase activity. The invention also relates to methods of using the compounds for in vitro, in situ, and in vivo diagnosis or treatment of mammalian cells, or associated pathological conditions.

BACKGROUND OF THE INVENTION

Combinations of anti-cancer pharmaceutical therapeutics administered simultaneously or sequentially in a dosing regimen are now common in cancer treatment. Successful combination therapy provides improved and even synergistic effect over mono-therapy, i.e. pharmaceutical treatment limited to one drug (Ouchi et al (2006) Cancer Chemother. Pharmacol. 57:693-702; Higgins et al (2004) Anti-Cancer Drugs 15:503-512). Preclinical research has been the basis for prediction of clinical stage synergy of anti-cancer pharmaceutical therapeutic combinations such as capecitabine and taxanes for the treatment of breast cancer (Sawada et al (1998) Clin. Cancer Res. 4:1013-1019). Certain doses and schedules of combination therapy can improve safety without compromising efficacy (O'Shaughnessy et al (2006) Clin. Breast Cancer April 7(1):42-50). Synergistic effects in vitro have been correlated with clinical stage synergy (Steinbach et al (2003) Clin. Inf. Dis. October 1:37 Suppl 3:S188-224).

Upregulation of the phosphoinositide-3 kinase (PI3K)/Akt signaling pathway is a common feature in most cancers (Yuan and Cantley (2008) Oncogene 27:5497-510). Genetic deviations in the pathway have been detected in many human cancers (Osaka et al (2004) Apoptosis 9:667-76) and act primarily to stimulate cell proliferation, migration and survival. Activation of the pathway occurs following activating point mutations or amplifications of the PIK3CA gene encoding the p110a PI3K isoforms (Hennessy et al (2005) Nat. Rev. Drug Discov. 4:988-1004). Genetic deletion or loss of function mutations within the tumor suppressor PTEN, a phosphatase with opposing function to PI3K, also increases PI3K pathway signaling (Zhang and Yu (2010) Clin. Cancer Res. 16:4325-30. These aberrations lead to increased downstream signaling through kinases such as Akt and mTOR and increased activity of the PI3K pathway has been proposed as a hallmark of resistance to cancer treatment (Opel et al (2007) Cancer Res. 67:735-45; Razis et al (2011) Breast Cancer Res. Treat. 128:447-56).

Phosphatidylinositol 3-Kinase (PI3K) is a major signaling node for key survival and growth signals for lymphomas and is opposed by the activity of the phosphatase PTEN. The PI3K pathway is dysregulated in aggressive forms of lymphoma (Abubaker (2007) Leukemia 21:2368-2370). Eight percent of DLBCL (diffuse large B-cell lymphoma) cancers have PI3CA (phosphatidylinositol-3 kinase catalytic subunit alpha) missense mutations and 37% are PTEN negative by immunohistochemistry test.

Phosphatidylinositol is one of a number of phospholipids found in cell membranes, and which participate in intracellular signal transduction. Cell signaling via 3'-phosphorylated phosphoinositides has been implicated in a variety of cellular processes, e.g., malignant transformation, growth factor signaling, inflammation, and immunity (Rameh et al (1999) J. Biol Chem. 274:8347-8350). The enzyme responsible for generating these phosphorylated signaling products, phosphatidylinositol 3-kinase (also referred to as PI 3-kinase or PI3K), was originally identified as an activity associated with viral oncoproteins and growth factor receptor tyrosine kinases that phosphorylate phosphatidylinositol (PI) and its phosphorylated derivatives at the 3'-hydroxyl of the inositol ring (Panayotou et al (1992) Trends Cell Biol 2:358-60). Phosphoinositide 3-kinases (PI3K) are lipid kinases that phosphorylate lipids at the 3-hydroxyl residue of an inositol ring (Whitman et al (1988) Nature, 332:664). The 3-phosphorylated phospholipids (PIP3s) generated by PI3-kinases act as second messengers recruiting kinases with lipid binding domains (including plekstrin homology (PH) regions), such as Akt and PDK1, phosphoinositide-dependent kinase-1 (Vivanco et al (2002) Nature Rev. Cancer 2:489; Phillips et al (1998) Cancer 83:41).

The PI3 kinase family comprises at least 15 different enzymes sub-classified by structural homology and are divided into 3 classes based on sequence homology and the product formed by enzyme catalysis. The class I PI3 kinases are composed of 2 subunits: a 110 kd catalytic subunit and an 85 kd regulatory subunit. The regulatory subunits contain SH2 domains and bind to tyrosine residues phosphorylated by growth factor receptors with a tyrosine kinase activity or oncogene products, thereby inducing the PI3K activity of the p110 catalytic subunit which phosphorylates its lipid substrate. Class I PI3 kinases are involved in important signal transduction events downstream of cytokines, integrins, growth factors and immunoreceptors, which suggests that control of this pathway may lead to important therapeutic effects such as modulating cell proliferation and carcinogenesis. Class I PI3Ks can phosphorylate phosphatidylinositol (PI), phosphatidylinositol-4-phosphate, and phosphatidylinositol-4,5-biphosphate (PIP2) to produce phosphatidylinositol-3-phosphate (PIP), phosphatidylinositol-3,4-biphosphate, and phosphatidylinositol-3,4,5-triphosphate, respectively. Class II PI3Ks phosphorylate PI and phosphatidylinositol-4-phosphate. Class III PI3Ks can only phosphorylate PI. A key PI3-kinase isoform in cancer is the Class I PI3-kinase, p110α as indicated by recurrent oncogenic mutations in p110α (Samuels et al (2004) Science 304:554; U.S. Pat. No. 5,824,492; U.S. Pat. No. 5,846,824; U.S. Pat. No. 6,274,327). Other isoforms may be important in cancer and are also implicated in cardiovascular and immune-inflammatory disease (Workman P (2004) Biochem Soc Trans 32:393-396; Patel et al (2004) Proc. Am. Assoc. of Cancer Res. (Abstract LB-247) 95th Annual Meeting, March 27-31, Orlando, Fla., USA; Ahmadi K and Waterfield M D (2004) "Phosphoinositide 3-Kinase: Function and Mechanisms" Encyclopedia of Biological Chemistry (Lennarz W J, Lane M D eds) Elsevier/Academic Press), Oncogenic mutations of p10 alpha have been found at a significant frequency in colon, breast, brain, liver, ovarian, gastric, lung, and head and neck solid tumors. About 35-40% of hormone receptor positive (HR+) breast cancer tumors harbor a PIK3CA mutation.

PTEN abnormalities are found in glioblastoma, melanoma, prostate, endometrial, ovarian, breast, lung, head and neck, hepatocellular, and thyroid cancers.

PI3 kinase is a heterodimer consisting of p85 and p110 subunits (Otsu et al (1991) Cell 65:91-104; Hiles et al (1992) Cell 70:419-29). Four distinct Class I PI3Ks have been identified, designated PI3K α (alpha), β (beta), δ (delta), and ω (gamma), each consisting of a distinct 110 kDa catalytic subunit and a regulatory subunit. Three of the catalytic subunits, i.e., p110 alpha, p110 beta and p110 delta, each interact with the same regulatory subunit, p85; whereas p110 gamma interacts with a distinct regulatory subunit, p101. The patterns of expression of each of these PI3Ks in human cells and tissues are distinct. In each of the PI3K alpha, beta, and delta subtypes, the p85 subunit acts to localize PI3 kinase to the plasma membrane by the interaction of its SH2 domain with phosphorylated tyrosine residues (present in an appropriate sequence context) in target proteins (Rameh et al (1995) Cell, 83:821-30; Volinia et al (1992) Oncogene, 7:789-93).

Measuring expression levels of biomarkers (e.g., secreted proteins in plasma) can be an effective means to identify patients and patient populations that will respond to specific therapies including, e.g., treatment with chemotherapeutic agents. There is a need for more effective means for determining which patients with hyperproliferative disorders such as cancer will respond to which treatment with chemotherapeutic agents, and for incorporating such determinations into more effective treatment regimens for patients, whether the chemotherapeutic agents are used as single agents or combined with other agents.

The PI3 kinase/Akt/PTEN pathway is an attractive target for cancer drug development since such agents would be expected to inhibit cellular proliferation, to repress signals from stromal cells that provide for survival and chemoresistance of cancer cells, to reverse the repression of apoptosis and surmount intrinsic resistance of cancer cells to cytotoxic agents. PI3 kinase inhibitors have been reported (Yaguchi et al (2006) Jour. of the Nat. Cancer Inst. 98(8):545-556; U.S. Pat. No. 7,173,029; U.S. Pat. No. 7,037,915; U.S. Pat. No. 6,608,056; U.S. Pat. No. 6,608,053; U.S. Pat. No. 6,838,457; U.S. Pat. No. 6,770,641; U.S. Pat. No. 6,653,320; U.S. Pat. No. 6,403,588; U.S. Pat. No. 7,750,002; WO 2006/046035; U.S. Pat. No. 7,872,003; WO 2007/042806; WO 2007/042810; WO 2004/017950; US 2004/092561; WO 2004/007491; WO 2004/006916; WO 2003/037886; US 2003/149074; WO 2003/035618; WO 2003/034997; US 2003/158212; EP 1417976; US 2004/053946; JP 2001247477; JP 08175990; JP 08176070).

Certain thienopyrimidine compounds have p110 alpha binding, PI3 kinase inhibitory activity, and inhibit the growth of cancer cells (Wallin et al (2011) Mol. Can. Ther. 10(12): 2426-2436; Sutherlin et al (2011) Jour. Med. Chem. 54:7579-7587; US 2008/0207611; U.S. Pat. No. 7,846,929; U.S. Pat. No. 7,781,433; US 2008/0076758; U.S. Pat. No. 7,888,352; US 2008/0269210. GDC-0941 (CAS Reg. No. 957054-30-7, Genentech Inc.), is a selective, orally bioavailable inhibitor of PI3K with promising pharmacokinetic and pharmaceutical properties (Folkes et al (2008) Jour. of Med. Chem. 51(18): 5522-5532; U.S. Pat. No. 7,781,433; Belvin et al, American Association for Cancer Research Annual Meeting 2008, 99th: April 15, Abstract 4004; Folkes et al, American Association for Cancer Research Annual Meeting 2008, 99th: April 14, Abstract LB-146; Friedman et al, American Association for Cancer Research Annual Meeting 2008, 99th: April 14, Abstract LB-110) and shows synergistic activity in vitro and in vivo in combination with certain chemotherapeutic agents against solid tumor cell lines (US 2009/0098135).

GDC-0032 (Roche RG7604, CAS Reg. No. 1282512-48-4), named as 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanamide, has potent PI3K activity (WO 2011/036280; U.S. Pat. No. 8,242,104; U.S. Pat. No. 8,343,955) and is being studied in patients with locally advanced or metastatic solid tumors.

SUMMARY OF THE INVENTION

It has been determined that additive or synergistic effects in inhibiting the growth of cancer cells in vitro and in vivo can be achieved by administering the compound GDC-0032, or a pharmaceutically acceptable salt thereof, in combination with certain other specific chemotherapeutic agents. The combinations and methods may be useful in the treatment of hyperproliferative disorders such as cancer.

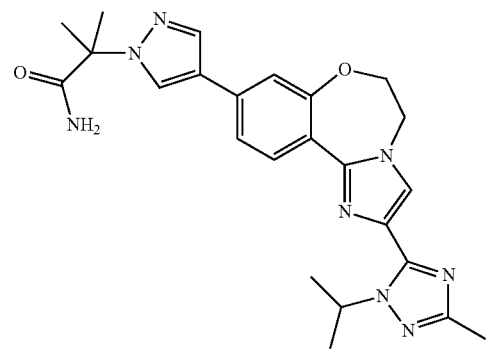 [SMILES: Cc1nc(-c2cn3c(n2)-c2ccc(-c4cnn(C(C)(C)C(N)=O)c4)cc2OCC3)n(C(C)C)n1]

GDC-0032

In one aspect the invention includes a method for the treatment of a hyperproliferative disorder comprising administering a therapeutic combination as a combined formulation or by alternation to a mammal, wherein the therapeutic combination comprises a therapeutically effective amount of GDC-0032 and a therapeutically effective amount of a chemotherapeutic agent selected from 5-FU, docetaxel, eribulin, gemcitabine, GDC-0973, GDC-0623, paclitaxel, tamoxifen, fulvestrant, dexamethasone, pertuzumab, trastuzumab emtansine, trastuzumab and letrozole.

In one aspect the invention provides a method for treating the hyperproliferative disorder wherein administration of GDC-0032 and one or more chemotherapeutic agents selected from 5-FU, docetaxel, eribulin, gemcitabine, GDC-0973, GDC-0623, paclitaxel, tamoxifen, fulvestrant, dexamethasone, pertuzumab, trastuzumab emtansine, trastuzumab and letrozole provides a synergistic effect in treating the hyperproliferative disorder. In a further aspect, the synergistic effect has a Combination Index value of less than about 0.8.

In one aspect the invention provides the therapeutic combination further including carboplatin.

In one aspect the invention includes the therapeutic combination further including an anti-VEGF antibody.

In one aspect of the invention includes the anti-VEGF antibody is bevacizumab.

In one aspect of the invention includes the pharmaceutically acceptable salt of GDC-0032 is selected from a salt formed with hydrochloric acid, hydrobromic acid, hydroiodic acid, sulfuric acid, nitric acid, phosphoric acid, methanesulfonic acid, benzenesulfonic acid, formic acid, acetic acid, trifluoroacetic acid, propionic acid, oxalic acid, malonic acid, succinic acid, fumaric acid, maleic acid, lactic acid, malic acid, tartaric acid, citric acid, ethanesulfonic acid, aspartic acid and glutamic acid.

In one aspect the invention includes a method of treating a hyperproliferative disorder in a patient comprising administering a therapeutically effective amount of GDC-0032, or a combination of GDC-0032 and a chemotherapeutic agent, to the patient, wherein a biological sample obtained from the patient, prior to administration of the combination to the patient, has been tested for status of a biomarker, and wherein the biomarker status is indicative of therapeutic responsiveness by the patient to GDC-0032, or a combination of GDC-0032 and a chemotherapeutic agent. In one embodiment, the biological sample has been tested by measuring functional biomarker protein level, wherein an increased level of functional biomarker indicates that the patient will be resistant to GDC-0032 or the combination. In another embodiment, the biological sample has been tested by measuring functional biomarker level, wherein an increased or decreased level of functional biomarker indicates that the patient will be resistant to GDC-0032 or the combination.

In one aspect the invention includes a pharmaceutical formulation comprising GDC-0032 and a chemotherapeutic agent selected from 5-FU, docetaxel, eribulin, gemcitabine, GDC-0973, GDC-0623, paclitaxel, tamoxifen, fulvestrant, dexamethasone, pertuzumab, trastuzumab emtansine, trastuzumab and letrozole.

In one aspect the invention includes a use of a therapeutic combination of GDC-0032 and a chemotherapeutic agent selected from 5-FU, docetaxel, eribulin, gemcitabine, GDC-0973, GDC-0623, paclitaxel, tamoxifen, fulvestrant, dexamethasone, pertuzumab, trastuzumab emtansine, trastuzumab and letrozole in the manufacture of a medicament for the treatment of cancer selected from breast, cervical, colon, endometrial, glioma, lung, melanoma, ovarian, pancreatic, and prostate.

In one aspect the invention includes an article of manufacture for treating a hyperproliferative disorder comprising:
  a) a therapeutic combination of GDC-0032 and a chemotherapeutic agent selected from 5-FU, docetaxel, eribulin, gemcitabine, GDC-0973, GDC-0623, paclitaxel, tamoxifen, fulvestrant, dexamethasone, pertuzumab, trastuzumab emtansine, trastuzumab and letrozole; and
  b) instructions for use.

In one aspect the invention includes a product comprising GDC-0032 and a chemotherapeutic agent selected from 5-FU, docetaxel, eribulin, gemcitabine, GDC-0973, GDC-0623, paclitaxel, tamoxifen, fulvestrant, dexamethasone, pertuzumab, trastuzumab emtansine, trastuzumab and letrozole; as a combined formulation for separate, simultaneous or sequential use in the treatment of a hyperproliferative disorder.

In one aspect the invention includes a method for determining compounds to be used in combination for the treatment of cancer comprising:
  a) treating an in vitro tumor cell line with a K-ras mutation with a therapeutic combination of GDC-0032 and a chemotherapeutic agent selected from 5-FU, docetaxel, eribulin, gemcitabine, GDC-0973, GDC-0623, paclitaxel, tamoxifen, fulvestrant, dexamethasone, pertuzumab, trastuzumab emtansine, trastuzumab and letrozole, and
  b) measuring a synergistic or non-synergistic effect;
  whereby a synergistic therapeutic combination for the treatment of cancer is determined.

In one aspect the invention includes a method for selecting compounds to be used in combination for the treatment of cancer comprising:
  a) administering a therapeutic combination of GDC-0032 and a chemotherapeutic agent selected from 5-FU, docetaxel, eribulin, gemcitabine, GDC-0973, GDC-0623, paclitaxel, tamoxifen, fulvestrant, dexamethasone, pertuzumab, trastuzumab emtansine, trastuzumab and letrozole to tumor cells;
  b) measuring a change in pAkt level; and
  c) selecting a synergistic therapeutic combination which shows an increase in pAkt levels.

In one aspect the invention includes a method of treating a hyperproliferative disorder in a patient comprising administering a therapeutically effective amount of GDC-0032 or a combination of GDC-0032 and a chemotherapeutic agent selected from 5-FU, docetaxel, eribulin, gemcitabine, GDC-0973, GDC-0623, paclitaxel, tamoxifen, fulvestrant, dexamethasone, pertuzumab, trastuzumab emtansine, trastuzumab and letrozole to the patient, wherein a biological sample obtained from the patient, prior to administration of the combination to the patient, has been tested for PIK3CA or PTEN mutation status, and wherein PIK3CA or PTEN mutation status is indicative of therapeutic responsiveness by the patient to the combination. The patient is administered a therapeutically effective amount of GDC-0032 as a single agent, or a combination of GDC-0032 and a chemotherapeutic agent. The biological sample may be tested by measuring functional PI3K protein level after administration of GDC-0032 or the combination of GDC-0032 and the chemotherapeutic agent, wherein a change in the level of functional PI3K protein indicates that the patient will be resistant or responsive to GDC-0032 or the combination of GDC-0032 and a chemotherapeutic agent.

In one aspect the invention includes a method of monitoring whether a patient with a hyperproliferative disorder will respond to treatment with GDC-0032 or a combination of GDC-0032 and a chemotherapeutic agent, the method comprising:
  (a) detecting a PIK3CA or PTEN mutation in a biological sample obtained from the patient following administration of the at least one dose of GDC-0032 or the combination of GDC-0032 and a chemotherapeutic agent selected from 5-FU, docetaxel, eribulin, gemcitabine, GDC-0973, GDC-0623, paclitaxel, tamoxifen, fulvestrant, dexamethasone, pertuzumab, trastuzumab emtansine, trastuzumab and letrozole; and
  (b) comparing PIK3CA or PTEN mutation status in a biological sample obtained from the patient prior to administration of GDC-0032 or the combination of GDC-0032 and a chemotherapeutic agent to the patient,
  wherein a change or modulation of PIK3CA or PTEN mutation status in the sample obtained following administration of GDC-0032 or the combination of GDC-0032 and a chemotherapeutic agent identifies a patient who will respond to treatment with GDC-0032 or the combination of GDC-0032 and a chemotherapeutic agent.

In one aspect the invention includes a method of optimizing therapeutic efficacy of GDC-0032 or the combination of GDC-0032 and a chemotherapeutic agent, the method comprising:
  (a) detecting a PIK3CA or PTEN mutation in a biological sample obtained from a patient following administration of at least one dose of GDC-0032 or the combination of GDC-0032 and a chemotherapeutic agent selected from 5-FU, docetaxel, eribulin, gemcitabine, GDC-0973, GDC-0623, paclitaxel, tamoxifen, fulvestrant, dexamethasone, pertuzumab, trastuzumab emtansine, trastuzumab and letrozole; and
(b) comparing the PIK3CA or PTEN status in a biological sample obtained from the patient prior to administration of GDC-0032 or the combination of GDC-0032 and a chemotherapeutic agent to the patient,
wherein a change or modulation of PIK3CA or PTEN in the sample obtained following administration of GDC-0032 or the combination of GDC-0032 and a chemotherapeutic agent identifies a patient who has an increased likelihood of benefit from treatment with GDC-0032 or the combination of GDC-0032 and a chemotherapeutic agent.

In one aspect the invention includes a method of identifying a biomarker for monitoring responsiveness to GDC-0032 or the combination of GDC-0032 and a chemotherapeutic agent, the method comprising:
(a) detecting the expression, modulation, or activity of a biomarker selected from a PIK3CA or PTEN mutation in a biological sample obtained from a patient who has received at least one dose of GDC-0032 or the combination of GDC-0032 and a chemotherapeutic agent selected from 5-FU, docetaxel, eribulin, gemcitabine, GDC-0973, GDC-0623, paclitaxel, tamoxifen, fulvestrant, dexamethasone, pertuzumab, trastuzumab emtansine, trastuzumab and letrozole; and
(b) comparing the expression, modulation, or activity of the biomarker to the status of the biomarker in a reference sample wherein the reference sample is a biological sample obtained from the patient prior to administration of GDC-0032 or the combination of GDC-0032 and a chemotherapeutic agent to the patient;
wherein the modulation of the biomarker changes by at least 2 fold lower or higher compared to the reference sample is identified as a biomarker useful for monitoring responsiveness to GDC-0032 or the combination of GDC-0032 and a chemotherapeutic agent. In one embodiment the biomarker is pAkt.

In one aspect the invention includes a method of treating a hyperproliferative disorder in a patient, comprising administering a therapeutically effective amount of GDC-0032 or the combination of GDC-0032 and a chemotherapeutic agent selected from 5-FU, docetaxel, eribulin, gemcitabine, GDC-0973, GDC-0623, paclitaxel, tamoxifen, fulvestrant, dexamethasone, pertuzumab, trastuzumab emtansine, trastuzumab and letrozole to the patient, wherein treatment is based upon a sample from the patient having a PIK3CA or PTEN mutation. The biomarker mutation may be the H1047R, H1047L, E545K, or E542K mutation of PIK3CA.

In one aspect the invention includes a use of GDC-0032 or a combination of GDC-0032 and a chemotherapeutic agent in treating a hyperproliferative disorder in a patient comprising administering a therapeutically effective amount of GDC-0032 or the combination of GDC-0032 and a chemotherapeutic agent selected from 5-FU, docetaxel, eribulin, gemcitabine, GDC-0973, GDC-0623, paclitaxel, tamoxifen, fulvestrant, dexamethasone, pertuzumab, trastuzumab emtansine, trastuzumab and letrozole to the patient,
wherein a biological sample obtained from the patient, prior to administration of GDC-0032 or the combination of GDC-0032 and a chemotherapeutic agent to the patient, has been tested for PIK3CA or PTEN mutation status, and wherein PIK3CA or PTEN mutation status is indicative of therapeutic responsiveness by the patient to GDC-0032 or the combination of GDC-0032 and a chemotherapeutic agent.

BRIEF DESCRIPTION OF THE DRAWINGS

FIG. 37A shows the activity of letrozole and GDC-0032 in aromatase expressing MCF7 cells without androstenedione.

FIG. 37B shows the activity of letrozole and GDC-0032 in aromatase expressing MCF7 cells with androstenedione.

FIG. 38A shows GDC-0032 combines well with letrozole in vitro by quantitative scoring of inhibition of cell viability in a 4 day Cell Titer-Glo Assay.

FIG. 38B shows GDC-0032 combines well with letrozole in vitro by quantitative BLISS Score in a 4 day Cell Titer-Glo Assay.

FIG. 38C shows GDC-0032 combines well with letrozole in vitro by quantitative HSA Score in a 4 day Cell Titer-Glo Assay.

FIG. 38D shows cleavage of PARP in a 4 day Cell Titer-Glo Assay in cells treated with GDC-0032, letrozole, the combination of GDC-0032 and letrozole, and negative control.

FIG. 39A shows cross-talk between the PI3K and ER pathways suggesting a mechanism of action for the combination of GDC-0032 and letrozole.

FIG. 39B shows cross-talk between the PI3K and ER pathways suggesting a mechanism of action for the combination of GDC-0032 and letrozole.

FIG. 40A shows endocrine resistant MCF7-ARO cells in a 4 day CellTiter-Glo assay.

FIG. 40B shows endocrine resistant MCF7-ARO cells are sensitive to GDC-0032 after 24 hr treatments in a 4 day CellTiter-Glo assay.

FIG. 40C shows endocrine resistant MCF7-ARO cells have elevated PI3K pathway signaling and are sensitive to GDC-0032 after 24 hr treatments in a 4 day CellTiter-Glo assay.

Figure 44:
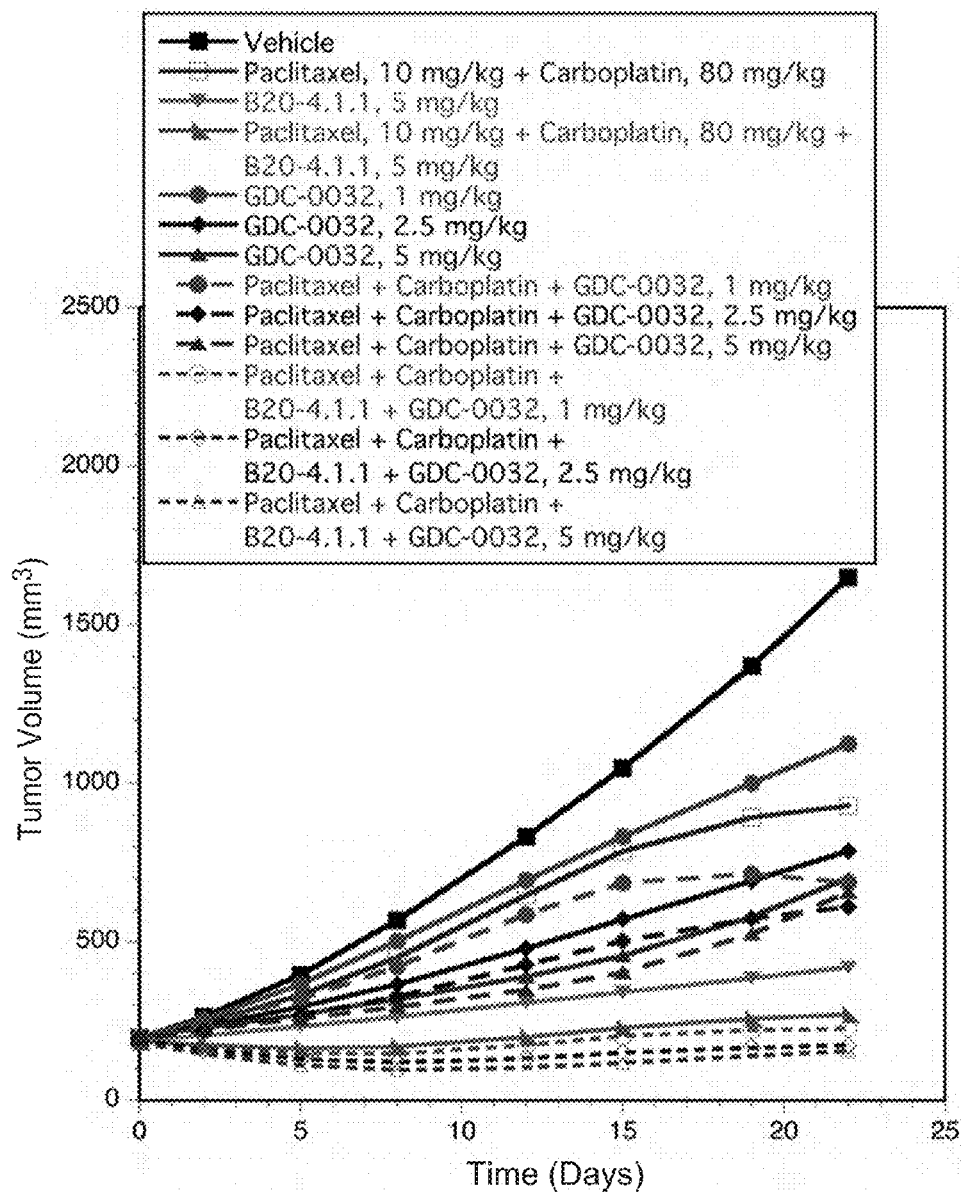

FIG. 44 shows the fitted tumor volume change over 22 days in cohorts of 10 immunocompromised mice with H292 (KR-ASmut) NSCLC (non-small cell lung cancer) xenografts dosed with vehicle, paclitaxel, carboplatin, anti-VEGF antibody (B20-4.1.1), GDC-0032, and triple and quadruple combinations of GDC-0032+paclitaxel (PTX), carboplatin, +/−anti-VEGF. GDC-0032 was dosed orally (PO) and daily (QD) for 21 days. Paclitaxel was dosed intravenously on day 1 with 10 mg/kg of drug, carboplatin was dosed intraperitoneally on day 1 with 80 mg/kg of drug, and anti-VEGF was dosed intraperitoneally twice a week for 3 weeks with 5 mg/kg of drug.

DETAILED DESCRIPTION OF EXEMPLARY EMBODIMENTS

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

DEFINITIONS

The words "comprise," "comprising," "include," "including," and "includes" when used in this specification and claims are intended to specify the presence of stated features, integers, components, or steps, but they do not preclude the presence or addition of one or more other features, integers, components, steps, or groups thereof.

The terms "treat" and "treatment" refer to both therapeutic treatment and prophylactic or preventative measures, wherein the object is to prevent or slow down (lessen) an undesired physiological change or disorder, such as the growth, development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The term "detection" includes any means of detecting, including direct and indirect detection.

The term "diagnosis" is used herein to refer to the identification or classification of a molecular or pathological state, disease or condition. For example, "diagnosis" may refer to identification of a particular type of cancer, e.g., a lung cancer. "Diagnosis" may also refer to the classification of a particular type of cancer, e.g., by histology (e.g., a non small cell lung carcinoma), by molecular features (e.g., a lung cancer characterized by nucleotide and/or amino acid variation(s) in a particular gene or protein), or both.

The term "prognosis" is used herein to refer to the prediction of the likelihood of cancer-attributable death or progression, including, for example, recurrence, metastatic spread, and drug resistance, of a neoplastic disease, such as cancer.

The term "prediction" (and variations such as predicting) is used herein to refer to the likelihood that a patient will respond either favorably or unfavorably to a drug or set of drugs. In one embodiment, the prediction relates to the extent of those responses. In another embodiment, the prediction relates to whether and/or the probability that a patient will survive following treatment, for example treatment with a particular therapeutic agent and/or surgical removal of the primary tumor, and/or chemotherapy for a certain period of time without cancer recurrence. The predictive methods of the invention can be used clinically to make treatment decisions by choosing the most appropriate treatment modalities for any particular patient. The predictive methods of the present invention are valuable tools in predicting if a patient is likely to respond favorably to a treatment regimen, such as a given therapeutic regimen, including for example, administration of a given therapeutic agent or combination, surgical intervention, chemotherapy, etc., or whether long-term survival of the patient, following a therapeutic regimen is likely.

The term "increased resistance" to a particular therapeutic agent or treatment option, when used in accordance with the invention, means decreased response to a standard dose of the drug or to a standard treatment protocol.

The term "decreased sensitivity" to a particular therapeutic agent or treatment option, when used in accordance with the invention, means decreased response to a standard dose of the agent or to a standard treatment protocol, where decreased response can be compensated for (at least partially) by increasing the dose of agent, or the intensity 5 of treatment.

"Patient response" can be assessed using any endpoint indicating a benefit to the patient, including, without limitation, (1) inhibition, to some extent, of tumor growth, including slowing down or complete growth arrest; (2) reduction in the number of tumor cells; (3) reduction in tumor size; (4) inhibition (e.g., reduction, slowing down or complete stopping) of tumor cell infiltration into adjacent peripheral organs and/or tissues; (5) inhibition (e.g., reduction, slowing down or complete stopping) of metastasis; (6) enhancement of anti-tumor immune response, which may, but does not have to, result in the regression or rejection of the tumor; (7) relief, to some extent, of one or more symptoms associated with the tumor; (8) increase in the length of survival following treatment; and/or (9) decreased mortality at a given point of time following treatment.

A "biomarker" is a characteristic that is objectively measured and evaluated as an indicator of normal biological processes, pathogenic processes, or pharmacological responses to a therapeutic intervention. Biomarkers may be of several types: predictive, prognostic, or pharmacodynamics (PD). Predictive biomarkers predict which patients are likely to respond or benefit from a particular therapy. Prognostic biomarkers predict the likely course of the patient's disease and may guide treatment. Pharmacodynamic biomarkers confirm drug activity, and enables optimization of dose and administration schedule.

"Change" or "modulation" of the status of a biomarker, including a PIK3CA mutation or set of PIK3CA mutations, as it occurs in vitro or in vivo is detected by analysis of a biological sample using one or more methods commonly employed in establishing pharmacodynamics (PD), including: (1) sequencing the genomic DNA or reverse-transcribed PCR products of the biological sample, whereby one or more mutations are detected; (2) evaluating gene expression levels by quantitation of message level or assessment of copy number; and (3) analysis of proteins by immunohistochemistry, immunocytochemistry, ELISA, or mass spectrometry whereby degradation, stabilization, or post-translational modifications of the proteins such as phosphorylation or ubiquitination is detected.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. Gastric cancer, as used herein, includes stomach cancer, which can develop in any part of the stomach and may spread throughout the stomach and to other organs; particularly the esophagus, lungs, lymph nodes, and the liver.

The term "hematopoietic malignancy" refers to a cancer or hyperproliferative disorder generated during hematopoiesis involving cells such as leukocytes, lymphocytes, natural killer cells, plasma cells, and myeloid cells such as neutrophils and monocytes. Hematopoietic malignancies include non-Hodgkin's lymphoma, diffuse large hematopoietic lymphoma, follicular lymphoma, mantle cell lymphoma, chronic lymphocytic leukemia, multiple myeloma, acute myelogenous leukemia, and myeloid cell leukemia. Lymphocytic leukemia (or "lymphoblastic") includes Acute lymphoblastic leukemia (ALL) and Chronic lymphocytic leukemia (CLL). Myelogenous leukemia (also "myeloid" or "nonlymphocytic") includes Acute myelogenous (or Myeloblastic) leukemia (AML) and Chronic myelogenous leukemia (CML).

A "chemotherapeutic agent" is a biological (large molecule) or chemical (small molecule) compound useful in the treatment of cancer, regardless of mechanism of action.

The term "mammal" includes, but is not limited to, humans, mice, rats, guinea pigs, monkeys, dogs, cats, horses, cows, pigs and sheep.

The term "package insert" is used to refer to instructions customarily included in commercial packages of therapeutic products, that contain information about the indications, usage, dosage, administration, contraindications and/or warnings concerning the use of such therapeutic products.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

The desired pharmaceutically acceptable salt may be prepared by any suitable method available in the art. For example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. Acids which are generally considered suitable for the formation of pharmaceutically useful or acceptable salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1 19; P. Gould, International J. of Pharmaceutics (1986) 33 201 217; Anderson et al, The Practice of Medicinal Chemistry (1996), Academic Press, New York; Remington's Pharmaceutical Sciences, 18$^{th}$ ed., (1995) Mack Publishing Co., Easton Pa.; and in The Orange Book (Food & Drug Administration, Washington, D.C. on their website). These disclosures are incorporated herein by reference thereto.

The phrase "pharmaceutically acceptable" indicates that the substance or composition must be compatible chemically and/or toxicologically, with the other ingredients comprising a formulation, and/or the mammal being treated therewith.

The term "synergistic" as used herein refers to a therapeutic combination which is more effective than the additive effects of the two or more single agents. A determination of a synergistic interaction between a compound of GDC-0032 or a pharmaceutically acceptable salt thereof and one or more chemotherapeutic agent may be based on the results obtained from the assays described herein. The results of these assays can be analyzed using the Chou and Talalay combination method and Dose-Effect Analysis with CalcuSyn software in order to obtain a Combination Index (Chou and Talalay, 1984, Adv. Enzyme Regul. 22:27-55). The combinations provided by this invention have been evaluated in several assay systems, and the data can be analyzed utilizing a standard program for quantifying synergism, additivism, and antagonism among anticancer agents. The program utilized, for example in FIG. 10, is that described by Chou and Talalay, in "New Avenues in Developmental Cancer Chemotherapy," Academic Press, 1987, Chapter 2. Combination Index values less than 0.8 indicates synergy, values greater than 1.2 indicate antagonism and values between 0.8 and 1.2 indicate additive effects. The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes or in separate pills or tablets. In general, during alternation therapy, an effective dosage of each active ingredient is administered sequentially, i.e., serially, whereas in combination therapy, effective dosages of two or more active ingredients are administered together. Combination effects were evaluated using both the BLISS independence model and the highest single agent (HSA) model (Lehár et al. 2007, Molecular Systems Biology 3:80). BLISS scores quantify degree of potentiation from single agents and a BLISS score >0 suggests greater than simple additivity. An HSA score >0 suggests a combination effect greater than the maximum of the single agent responses at corresponding concentrations.

"ELISA" (Enzyme-linked immunosorbent assay) is a popular format of a "wet-lab" type analytic biochemistry assay that uses one sub-type of heterogeneous, solid-phase enzyme immunoassay (EIA) to detect the presence of a substance in a liquid sample or wet sample (Engvall E, Perlman P (1971). "Enzyme-linked immunosorbent assay (ELISA). Quantitative assay of immunoglobulin G". Immunochemistry 8 (9): 871-4; Van Weemen B K, Schuurs A H (1971). "Immunoassay using antigen-enzyme conjugates". FEBS Letters 15 (3): 232-236). ELISA can perform other forms of ligand binding assays instead of strictly "immuno" assays, though the name carried the original "immuno" because of the common use and history of development of this method. The technique essentially requires any ligating reagent that can be immobilized on the solid phase along with a detection reagent that will bind specifically and use an enzyme to generate a signal that can be properly quantified. In between the washes only the ligand and its specific binding counterparts remain specifically bound or "immunosorbed" by antigen-antibody interactions to the solid phase, while the nonspecific or unbound components are washed away. Unlike other spectrophotometric wet lab assay formats where the same reaction well (e.g. a cuvette) can be reused after washing, the ELISA plates have the reaction products immunosorbed on the solid phase which is part of the plate and thus are not easily reusable. Performing an ELISA involves at least one antibody with specificity for a particular antigen. The sample with an unknown amount of antigen is immobilized on a solid support (usually a polystyrene microtiter plate) either non-specifically (via adsorption to the surface) or specifically (via capture by another antibody specific to the same antigen, in a "sandwich" ELISA). After the antigen is immobilized, the detection antibody is added, forming a complex with the antigen. The detection antibody can be covalently linked to an enzyme, or can itself be detected by a secondary antibody that is linked to an enzyme through bioconjugation. Between each step, the plate is typically washed with a mild detergent solution to remove any proteins or antibodies that are not specifically bound. After the final wash step, the plate is developed by adding an enzymatic substrate to produce a visible signal, which indicates the quantity of antigen in the sample.

"Immunohistochemistry" (IHC) refers to the process of detecting antigens (e.g., proteins) in cells of a tissue section by exploiting the principle of antibodies binding specifically to antigens in biological tissues. Immunohistochemical staining is widely used in the diagnosis of abnormal cells such as those found in cancerous tumors. Specific molecular markers are characteristic of particular cellular events such as proliferation or cell death (apoptosis). IHC is also widely used to understand the distribution and localization of biomarkers and differentially expressed proteins in different parts of a biological tissue. Visualising an antibody-antigen interaction can be accomplished in a number of ways. In the most common instance, an antibody is conjugated to an enzyme, such as peroxidase, that can catalyze a color-producing reaction (see immunoperoxidase staining). Alternatively, the antibody can also be tagged to a fluorophore, such as fluorescein or rhodamine (see immunofluorescence).

"Immunocytochemistry" (ICC) is a common laboratory technique that uses antibodies that target specific peptides or protein antigens in the cell via specific epitopes. These bound antibodies can then be detected using several different methods. ICC can evaluate whether or not cells in a particular sample express the antigen in question. In cases where an immunopositive signal is found, ICC also determines which sub-cellular compartments are expressing the antigen.

DETAILED DESCRIPTION OF EXEMPLARY EMBODIMENTS

Preparation of GDC-0032

The compound of the invention is known as GDC-0032 (CAS Reg. No. 1282512-48-4), named as 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanamide, and has the structure:

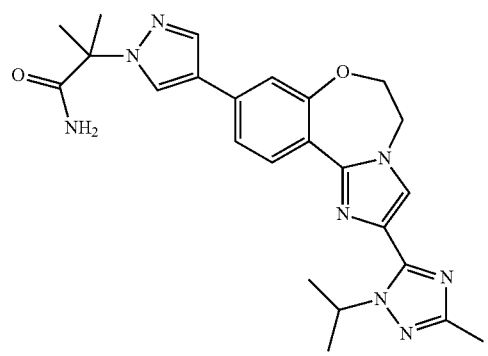

including stereoisomers, geometric isomers, tautomers, and pharmaceutically acceptable salts thereof.

GDC-0032 can be prepared and characterized as described in WO 2011/036280, U.S. Pat. No. 8,242,104, and U.S. Pat. No. 8,343,955, or as described in Example 1 below.

Chemotherapeutic Agents

Certain chemotherapeutic agents have demonstrated surprising and unexpected properties in combination with GDC-0032, in inhibiting cellular proliferation in vitro and in vivo. Such chemotherapeutic agents include: 5-FU, docetaxel, eribulin, gemcitabine, GDC-0973, GDC-0623, paclitaxel, tamoxifen, fulvestrant, dexamethasone, pertuzumab, trastuzumab emtansine, trastuzumab and letrozole.

5-FU (fluorouracil, 5-fluorouracil, CAS Reg. No. 51-21-8) is a thymidylate synthase inhibitor and has been used for decades in the treatment of cancer, including colorectal and pancreatic cancer (U.S. Pat. No. 2,802,005; U.S. Pat. No. 2,885,396; Duschinsky et al (1957) J. Am. chem. Soc. 79:4559; Hansen, R. M. (1991) Cancer Invest. 9:637-642). 5-FU is named as 5-fluoro-1H-pyrimidine-2,4-dione, and has the structure:

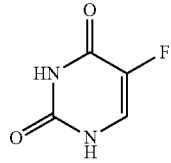

Docetaxel (TAXOTERE®, Sanofi-Aventis) is used to treat breast, ovarian, and NSCLC cancers (U.S. Pat. No. 4,814,470; U.S. Pat. No. 5,438,072; U.S. Pat. No. 5,698,582; U.S. Pat. No. 5,714,512; U.S. Pat. No. 5,750,561; Mangatal et al (1989) Tetrahedron 45:4177; Ringel et al (1991) J. Natl. Cancer Inst. 83:288; Bissery et al (1991) Cancer Res. 51:4845; Herbst et al (2003) Cancer Treat. Rev. 29:407-415; Davies et al (2003) Expert. Opin. Pharmacother. 4:553-565). Docetaxel is named as (2R,3S)—N-carboxy-3-phenylisoserine, N-tert-butyl ester, 13-ester with 5,20-epoxy-1,2,4,7,10,13-hexahydroxytax-11-en-9-one 4-acetate 2-benzoate, trihydrate (U.S. Pat. No. 4,814,470; EP 253738; CAS Reg. No. 114977-28-5) and has the structure:

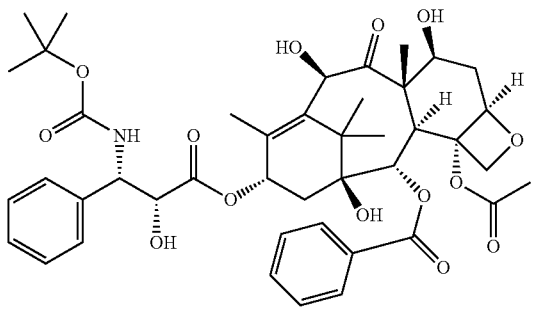

Eribulin (HALAVEN®, Eisai co., E7389, ER-086526, NSC 707389 (NS NCI designation)) is approved to treat patients with metastatic breast cancer who have received at least two prior chemotherapy regimens for late-stage breast cancer, and is being investigated for treatment of other solid tumors, including non-small cell lung cancer (NSCLC), prostate cancer and sarcoma. Eribulin is an analog of a marine sponge natural procut halichondrin B (Towle et al (2001) Cancer Res. 61(3):1013-1021; Yu et al (2005) Anticancer agents from natural products. Wash. D.C., Taylor & Francis, ISBN 0-8493-1863-7; Kim et al (2009) J. Am. Chem. Soc 131(43):15636-15641) from the *Halichondra* genus of sponges (Hirata, Y. and Uemura D. (1986) Pure Appl. Chem. 58(5):701-710; Bai et al (1991) J. Biol. Chem. 266(24): 15882-15889). Eribulin is an inhibitor of microtubules, binding predominantly to a selective group of high affinity sites at the plus ends of existing microtubules and exerts its anticancer effects by triggering apoptosis of cancer cells following prolonged and irreversible mitotic blockade (Jordan et al (2005) Mol. Cancer Ther. 4(7):1086-1095; Okouneva et al (2008) Mol. Cancer Ther. 7(7):2003-2011; Smith et al (2010) Biochem. 49(6)1331-1337; Kuznetsov et al (2004) Cancer Res. 64(16):5760-5766; Towle et al (2011 Cancer Res. 71(2): 496-505). Eribulin is named as 2-(3-Amino-2-hydroxypropyl)hexacosahydro-3-methoxy-26-methyl-20,27-bis(methylene) 11,15-18,21-24,28-triepoxy-7,9-ethano-12,15-methano-9H,15H-furo(3,2-i)furo(2',3'-5,6)pyrano(4,3-b)(1,4)dioxacyclopentacosin-5-(4H)-one (CAS Reg. No. 253128-41-5) and has the structure:

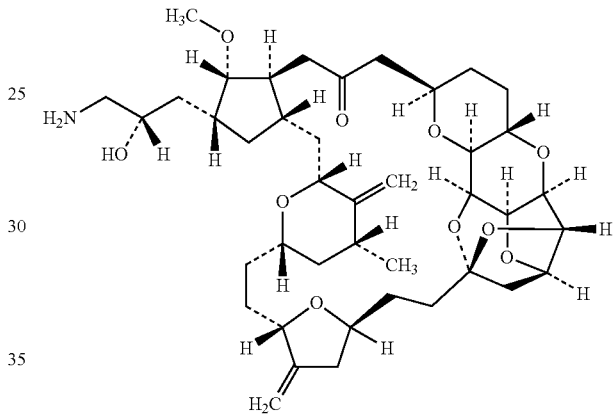

Gemcitabine (GEMZAR®, Lilly, CAS Reg. No. 95058-81-4) is a nucleoside analog which blocks DNA replication, is used to treat various carcinomas including pancreatic, breast, NSCLC, and lymphomas (U.S. Pat. No. 4,808,614; U.S. Pat. No. 5,464,826; Hertel et al (1988) J. Org. Chem. 53:2406; Hertel et al (1990) Cancer Res. 50:4417; Lund et al (1993) Cancer Treat. Rev. 19:45-55). Gemcitabine is named as 4-amino-1-[3,3-difluoro-4-hydroxy-5-(hydroxymethyl) tetrahydrofuran-2-yl]-1H-pyrimidin-2-one, and has the structure:

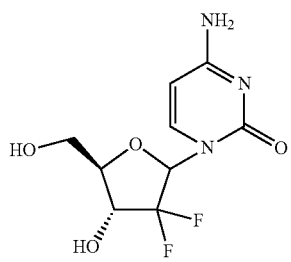 [SMILES: Nc1ccn(C2O[C@H](CO)[C@@H](O)C2(F)F)c(=O)n1]

GDC-0973 (XL-518, CAS Reg. Number: 934660-93-2, Genentech Inc. and Exelixis) is a potent and highly selective small-molecule inhibitor of MEK, to be orally administered, for the potential treatment of cancer, including solid tumors (U.S. Pat. No. 7,803,839; U.S. Pat. No. 7,999,006; U.S. Pat. No. 7,915,250). GDC-0973 and GDC-0941, a class I PI3K inhibitor, are in early stage clinical trials both as single agents and in combination (Hoeflich et al (2012) Cancer Research, 72(1):210-219; US 20110086837). Aberrant activation of the ERK pathway is common in human tumors. This pathway consists of a three-tiered kinase module comprising the kinases RAF, mitogen-activated protein kinase (MAPK) kinase (MEK), and extracellular signal-regulated kinase (ERK) that functions as a negative feedback amplifier to confer robustness and stabilization of pathway output. Because the ERK pathway is frequently dysregulated in human cancers, intense efforts are under way to develop selective inhibitors of the ERK pathway as anticancer drugs. The combination of GDC-0973 with the PI3K inhibitor GDC-0941 resulted in combination efficacy in vitro and in vivo via induction of biomarkers associated with apoptosis, including Bcl-2 family proapoptotic regulators. GDC-0973 is named as (S)-(3,4-difluoro-2-((2-fluoro-4-iodophenyl) amino)phenyl)(3-hydroxy-3-(piperidin-2-yl)azetidin-1-yl) methanone, and has the structure:

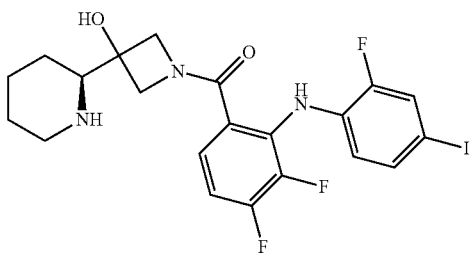 [SMILES: O=C(c1ccc(F)c(F)c1Nc1ccc(I)cc1F)N1CC(O)([C@@H]2CCCCN2)C1]

GDC-0623 (CAS Reg. Number: 1168091-68-6, Genentech Inc.) is a potent and highly selective small-molecule inhibitor of MEK, to be orally administered, for the potential treatment of cancer, including solid tumors (U.S. Pat. No. 7,923,456; US 2011/0158990). GDC-0623 is named as 5-((2-fluoro-4-iodophenyl)amino)-N-(2-hydroxyethoxy)imidazo[1,5-a]pyridine-6-carboxamide, and has the structure:

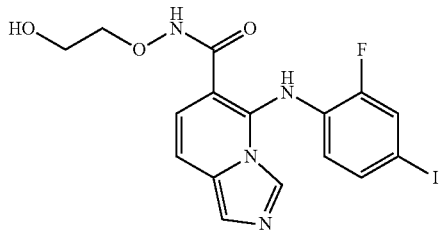 [SMILES: O=C(NOCCO)c1ccc2cncn2c1Nc1ccc(I)cc1F]

Paclitaxel (TAXOL®, Bristol-Myers Squibb Oncology, Princeton N.J., CAS Reg. No. 33069-62-4) is isolated the compound from the bark of the Pacific yew tree, *Taxus brevifolia*, and used to treat lung, ovarian, breast cancer, and advanced forms of Kaposi's sarcoma (Wani et al (1971) J. Am. Chem. Soc. 93:2325; Mekhail et al (2002) Expert. Opin. Pharmacother. 3:755-766). Paclitaxel is named as 3-(benzoylamino)-α-hydroxy-,6,12b-bis(acetyloxy)-12-(benzoyloxy)-2a,3,4,4a,5,6,9,10,11,12,12a,12b-dodecahydro-4,11-dihydroxy-4a,8,13,13-tetramethyl-5-oxo-7,11-methano-1H-cyclodeca(3,4)benz(1,2-b)oxet-9-ylester,(2aR-(2a-α,4-β,4a-β,6-β,9-α(α-R*,β-S*),11-α,12-α,12a-α,2b-α))-benzenepropanoic acid, and has the structure:

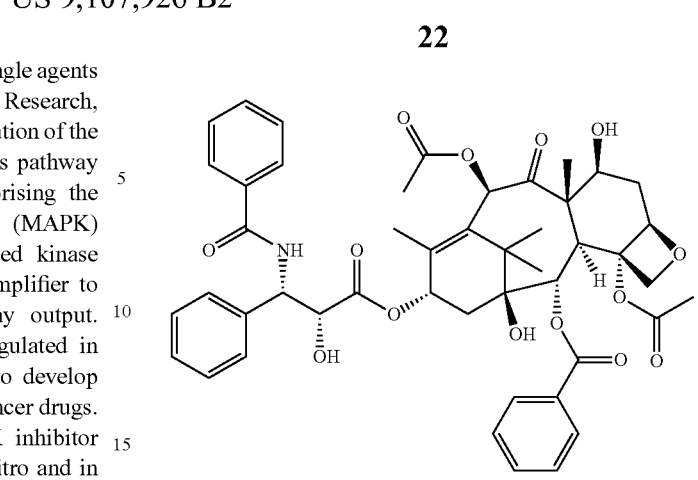

Tamoxifen (NOLVADEX®, ISTUBAL®, VALODEX®, CAS Reg. No. 10540-29-1) is an antagonist of the estrogen receptor in breast tissue via its active metabolite, hydroxytamoxifen. In other tissues such as the endometrium, it behaves as an agonist, and thus may be characterized as a mixed agonist/antagonist (New Engl. J. Med. (2009) 361:766 Aug. 20, 2009). Tamoxifen is the usual endocrine (anti-estrogen) therapy for hormone receptor-positive breast cancer in premenopausal women, and is also a standard in post-menopausal women although aromatase inhibitors are also frequently used in that setting. Tamoxifen is currently used for the treatment of both early and advanced ER+ (estrogen receptor positive) breast cancer in pre- and post-menopausal women (Jordan, V. (1993) Br J Pharmacol 110(2): 507-17). Tamoxifen is named as (Z)-2-[4-(1,2-diphenylbut-1-enyl) phenoxy]-N,N-dimethylethanamine, and has the structure:

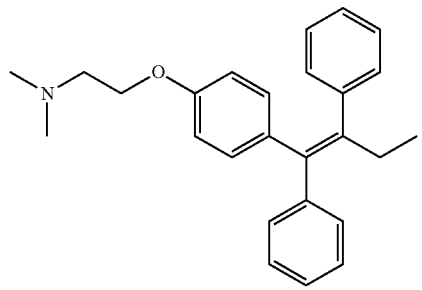 [SMILES: CC/C(=C(\c1ccccc1)c1ccc(OCCN(C)C)cc1)c1ccccc1]

Fulvestrant (FASLODEX®, AstraZeneca, CAS Reg. No. 129453-61-8) is a drug treatment of hormone receptor-positive metastatic breast cancer in postmenopausal women with disease progression following anti-estrogen therapy (Kansra (2005) Mol Cell Endocrinol 239(1-2):27-36). It is an estrogen receptor antagonist with no agonist effects, which works both by down-regulating and by degrading the estrogen receptor (Croxtall (2011) Drugs 71(3):363-380). Fulvestrant is a selective estrogen receptor down-regulator (SERD). Fulvestrant is indicated for the treatment of hormone receptor positive metastatic breast cancer in postmenopausal women with disease progression following anti-estrogen therapy (Flemming et al (2009) Breast Cancer Res Treat. May; 115(2):255-68; Valachis et al (2010) Crit Rev Oncol Hematol. March; 73(3):220-7). Fulvestrant is named as (7a,17l3)-7-{9-[(4,4,5,5,5-pentafluoropentyl)sulfinyl]nonyl}estra-1,3,5(10)-triene-3,17-diol and has the structure:

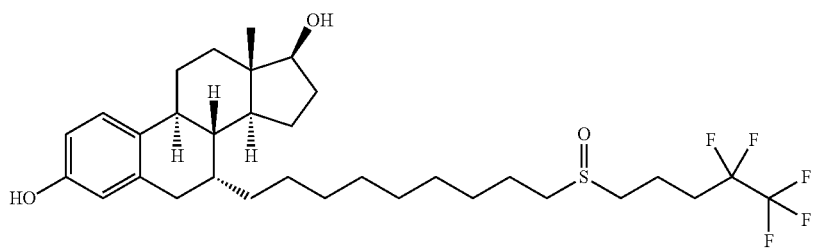

Dexamethasone is a potent glucocorticoid steroid hormone, with anti-inflammatory and immunosuppressant activity. In oncology, dexamethasone is given to cancer patients undergoing chemotherapy, to counteract certain side-effects of their antitumor treatment. Dexamethasone can augment the antiemetic effect of 5-$HT_3$ receptor antagonists like ondansetron. Dexamethasone is also used in certain hematological malignancies, especially in the treatment of multiple myeloma, in which dexamethasone is given alone or together with thalidomide (thal-dex) or a combination of Adriamycin (doxorubicin) and vincristine (VAD). In brain tumors (primary or metastatic), dexamethasone is used to counteract the development of edema, which could eventually compress other brain structures. Dexamethasone is named as (8S,9R,10S,11S,13S,14S,16R,17R)-9-fluoro-11,17-dihydroxy-17-(2-hydroxyacetyl)-10,13,16-trimethyl-6,7,8,11,12,14,15,16-octahydrocyclopenta[a]phenanthren-3-one (CAS Reg. No. 50-02-2) and has the structure:

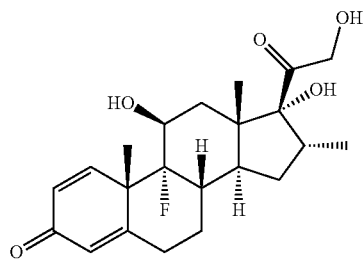

Pertuzumab (OMNITARG®, 2C4, rhuHAb 2C4, CAS Reg. No. 380610-27-5, Genentech) is a recombinant, humanized monoclonal antibody that inhibits dimerization of HER2 (U.S. Pat. No. 6,054,297; U.S. Pat. No. 6,407,213; U.S. Pat. No. 6,800,738; U.S. Pat. No. 6,627,196, U.S. Pat. No. 6,949,245; U.S. Pat. No. 7,041,292). Pertuzumab and trastuzumab target different extracellular regions of the HER-2 tyrosine kinase receptor (Nahta et al (2004) Cancer Res. 64:2343-2346). The hybridoma cell line expressing 2C4 (pertuzumab) was deposited with the American Type Culture Collection (ATCC), 10801 University Boulevard, Manassas, Va. 20110-2209, USA as ATCC HB-12697 on Apr. 8, 1999. Pertuzumab blocks the ability of the HER2 receptor to collaborate with other HER receptor family members, i.e. HER1/EGFR, HER3, and HER4 (Agus et al (2002) Cancer Cell 2:127-37; Jackson et al (2004) Cancer Res 64:2601-9; Takai et al (2005) Cancer 104:2701-8; U.S. Pat. No. 6,949,245). In cancer cells, interfering with the ability of HER2 to collaborate with other HER family receptors blocks cell signaling and may ultimately lead to cancer cell growth inhibition and death of the cancer cell. HDIs, because of their unique mode of action, have the potential to work in a wide variety of tumors, including those that do not overexpress HER2 (Mullen et al (2007) Molecular Cancer Therapeutics 6:93-100). Pertuzumab is being developed for the treatment of metastatic HER2-positive (+) breast cancer.

Trastuzumab emtansine (KADCYLA™, trastuzumab-DM1, PR-132365, PRO-132365; R-3502; RG-3502; Tmab-MCC-DM1, trastuzumab-mertansine Trastuzumab-MCC-DM1, T-DM1, Genentech Inc.) is an antibody-drug conjugate (CAS Reg. No. 139504-50-0) approved for treatment of HER2-positive (HER2+) metastatic breast cancer (Burris et al (2011) Clinical Breast Cancer, 11(5):275-82; Phillips et al (2008) Cancer Res 2008; 68(22):9280-9290. Trastuzumab emtansine has the structure:

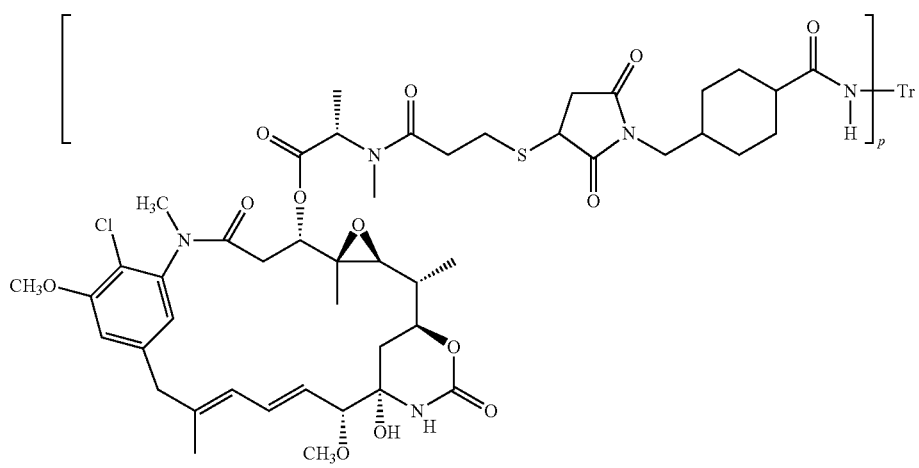

where Tr is trastuzumab, linked through linker moiety MCC, to the maytansinoid drug moiety, DM1 (U.S. Pat. No. 5,208,020; U.S. Pat. No. 6,441,163). The drug to antibody ratio or drug loading is represented by p in the above structure of trastuzumab-MCC-DM1, and ranges in integer values from 1 to about 8. The drug loading value p is 1 to 8. Trastuzumab-MCC-DM1 includes all mixtures of variously loaded and attached antibody-drug conjugates where 1, 2, 3, 4, 5, 6, 7, and 8 drug moieties are covalently attached to the antibody trastuzumab (U.S. Pat. No. 7,097,840; US 2005/0276812; US 2005/0166993).

Trastuzumab (HERCEPTIN®, huMAb4D5-8, rhuMAb HER2, Genentech) is a recombinant DNA-derived humanized, IgG1 kappa, monoclonal antibody version of the murine HER2 antibody which selectively binds with high affinity in a cell-based assay (Kd=5 nM) to the extracellular domain of the human epidermal growth factor receptor2 protein, HER2 (ErbB2) (U.S. Pat. No. 5,821,337; U.S. Pat. No. 6,054,297; U.S. Pat. No. 6,407,213; U.S. Pat. No. 6,639,055; Coussens L, et al (1985) Science 230:1132-9; Slamon D J, et al (1989) Science 244:707-12). Trastuzumab contains human framework regions with the complementarity-determining regions of a murine antibody (4D5) that binds to HER2. Trastuzumab binds to the HER2 antigen and thus inhibits the growth of cancerous cells. Trastuzumab has been shown, in both in vitro assays and in animals, to inhibit the proliferation of human tumor cells that overexpress HER2 (Hudziak R M, et al (1989) Mol Cell Biol 9:1165-72; Lewis G D, et al (1993) Cancer Immunol Immunother; 37:255-63; Baselga J, et al (1998) Cancer Res. 58:2825-2831). Trastuzumab is a mediator of antibody-dependent cellular cytotoxicity, ADCC (Hotaling T E, et al (1996) [abstract]. Proc. Annual Meeting Am Assoc Cancer Res; 37:471; Pegram M D, et al (1997) [abstract]. Proc Am Assoc Cancer Res; 38:602; Sliwkowski et al (1999) Seminars in Oncology 26(4), Suppl 12:60-70; Yarden Y. and Sliwkowski, M. (2001) Nature Reviews: Molecular Cell Biology, Macmillan Magazines, Ltd., Vol. 2:127-137). HERCEPTIN® was approved in 1998 for the treatment of patients with ErbB2-overexpressing metastatic breast cancers (Baselga et al, (1996) J. Clin. Oncol. 14:737-744). The FDA approved HERCEPTIN® in 2006 as part of a treatment regimen containing doxorubicin, cyclophosphamide and paclitaxel for the adjuvant treatment of patients with HER2-positive, node-positive breast cancer. There is a significant clinical need for developing further HER2-directed cancer therapies for those patients with HER2-overexpressing tumors or other diseases associated with HER2 expression that do not respond, or respond poorly, to HERCEPTIN® treatment.

Letrozole (FEMARA®, Novartis Pharm.) is an oral non-steroidal aromatase inhibitor for the treatment of hormonally-responsive breast cancer after surgery (Bhatnagar et al (1990) J. Steroid Biochem. and Mol. Biol. 37:1021; Lipton et al (1995) Cancer 75:2132; Goss, P. E. and Smith, R. E. (2002) Expert Rev. Anticancer Ther. 2:249-260; Lang et al (1993) The Journal of Steroid Biochem. and Mol. Biol. 44 (4-6):421-8; EP 236940; U.S. Pat. No. 4,978,672). FEMARA® is approved by the FDA for the treatment of local or metastatic breast cancer that is hormone receptor positive (HR+) or has an unknown receptor status in postmenopausal women. Letrozole is named as 4,4'-((1H-1,2,4-triazol-1-yl)methylene)dibenzonitrile (CAS Reg. No. 112809-51-5), and has the structure:

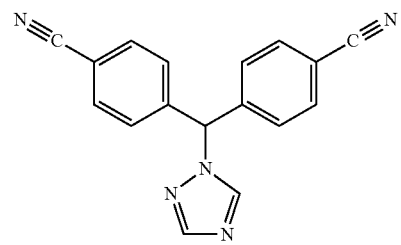 [SMILES: N#Cc1ccc(C(c2ccc(C#N)cc2)n2cncn2)cc1]

Carboplatin (CAS Reg. No. 41575-94-4) is a chemotherapeutic drug used against ovarian carcinoma, lung, head and neck cancers (U.S. Pat. No. 4,140,707). Carboplatin is named as azanide; cyclobutane-1,1-dicarboxylic acid platinum, and has the structure:

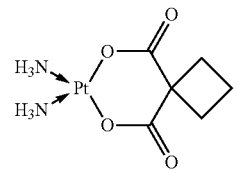

Bevacizumab (CAS Reg. No. 216974-75-3, AVASTIN®, Genentech) is an anti-VEGF monoclonal antibody against vascular endothelial growth factor (U.S. Pat. No. 7,227,004; U.S. Pat. No. 6,884,879; U.S. Pat. No. 7,060,269; U.S. Pat. No. 7,169,901; U.S. Pat. No. 7,297,334) used in the treatment of cancer, where it inhibits tumor growth by blocking the formation of new blood vessels. Bevacizumab was the first clinically available angiogenesis inhibitor in the United States, approved by the FDA in 2004 for use in combination with standard chemotherapy in the treatment of metastatic colon cancer and most forms of metastatic non-small cell lung cancer. Several late-stage clinical studies are underway to determine its safety and effectiveness for patients with: adjuvant/non-metastatic colon cancer, metastatic breast cancer, metastatic renal cell carcinoma, metastatic glioblastoma multiforme, metastatic ovarian cancer, metastatic hormone-refractory prostate cancer, and metastatic metastatic or unresectable locally advanced pancreatic cancer.

An anti-VEGF antibody will usually not bind to other VEGF homologues such as VEGF-B or VEGF-C, nor other growth factors such as PlGF, PDGF or bFGF. Preferred anti-VEGF antibodies include a monoclonal antibody that binds to the same epitope as the monoclonal anti-VEGF antibody A4.6.1 produced by hybridoma ATCC HB 10709; a recombinant humanized anti-VEGF monoclonal antibody generated according to Presta et al. (1997) Cancer Res. 57:4593-4599, including but not limited to bevacizumab which includes mutated human IgG1 framework regions and antigen-binding complementarity-determining regions from the murine anti-hVEGF monoclonal antibody A.4.6.1 that blocks binding of human VEGF to its receptors. Approximately 93% of the amino acid sequence of bevacizumab, including most of the framework regions, is derived from human IgG1, and about 7% of the sequence is derived from the murine antibody A4.6.1. Bevacizumab has a molecular mass of about 149,000 daltons and is glycosylated. Bevacizumab and other humanized anti-VEGF antibodies are further described in U.S. Pat. No. 6,884,879. Additional anti-VEGF antibodies include the G6 or B20 series antibodies (e.g., G6-31, B20-4.1), as described in any one of FIGS. 27-29 of WO2005/012359. In one embodiment, the B20 series antibody binds to a functional epitope on human VEGF comprising residues F17, M18, D19, Y21, Y25, Q89, I91, K101, E103, and C104. The A 4.6.1 (ATCC HB 10709) and B 2.6.2 (ATCC HB 10710) anti-VEGF expressing hybridoma cell lines have been deposited and maintained with the American Type Culture Collection (ATCC), 10801 University Boulevard, Manassas, Va. 20110-2209 USA. B20-4.1.1 is a bevacizumab surrogate (Liang et al (2006) Jour. Biol. Chem. 281:951-961). The clone expressing VEGF-E polypeptide (U.S. Pat. No. 6,391,311) encoded by the nucleotide sequence insert of the ATCC deposit identified as DNA29101-1276 was deposited on Mar. 5, 1998 and maintained as ATCC 209653 with the American Type Culture Collection, 10801 University Boulevard, Manassas, Va. 20110-2209, USA.

Biological Evaluation

The biological activities of GDC-0032 were measured as a single agent, and in combination with a variety of chemotherapeutic agents, including both small-molecules and large-molecules (proteins, antibodies). Such biological activities of GDC-0032, as a single agent and in combinations, were compared with PI3K inhibitors GDC-0941 and GDC-0980, both being developed by Genentech for the treatment of cancer.

GDC-0941 (pictrelisib, Genentech Inc., Roche, RG-7321) is a potent multitargeted class I (pan) inhibitor of PI3K isoforms. GDC-0941 is currently in phase II clinical trials for the treatment of advanced solid tumors. GDC-0941 is named as 4-(2-(1H-indazol-4-yl)-6-((4-(methylsulfonyl)piperazin-1-yl)methyl)thieno[3,2-d]pyrimidin-4-yl)morpholine (U.S. Pat. No. 7,781,433; U.S. Pat. No. 7,750,002; Folkes et al (2008) Jour. of Med. Chem. 51(18):5522-5532), and has the structure:

GDC0941

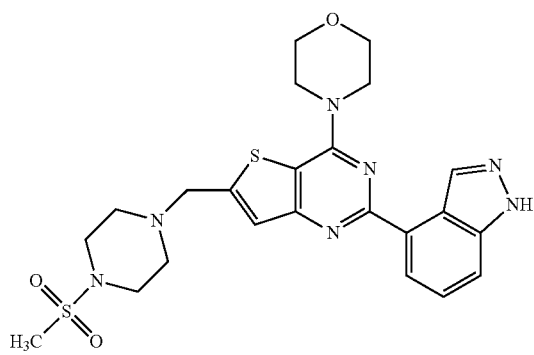

including stereoisomers, geometric isomers, tautomers, and pharmaceutically acceptable salts thereof.

GDC-0980 (Genentech Inc., Roche, RG-7422) is a potent dual inhibitor of mTOR and PI3K (Wallin et al (2011) Mol. Can. Ther. 10(12):2426-2436; Sutherlin et al (2011) Jour. Med. Chem. 54:7579-7587). GDC-0980 demonstrates broad activity in preclinical xenograft cancer models; breast, ovarian, lung, and prostate, and is being developed for the potential oral treatment of cancer including solid tumors and non-Hodgkin's lymphoma (Wagner A J; Burris III H A; de Bono J S et al AACR-NCI-EORTC International Congress (2009), 21st: November 17 (Abs B137) "Pharmacokinetics and Pharmacodynamic biomarkers for the dual PI3K/mTOR inhibitor GDC-0980: initial phase I evaluation"; U.S. Pat. No. 7,888,352; US 2009/0098135; US 2010/0233164). GDC-0980 is currently in phase II clinical trials for the treatment of advanced solid tumors. GDC-0980 is named as (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one, and has the structure:

GDC-0980

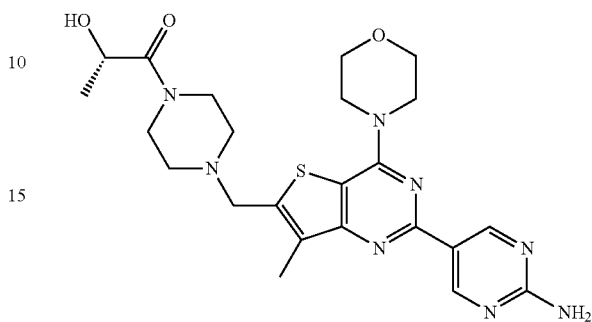

including stereoisomers, geometric isomers, tautomers, and pharmaceutically acceptable salts thereof.

TABLE 1

Comparison of binding activities of GDC-0032 and GDC-0941*

| Single agent binding activity (Example 2) | GDC-0032 | GDC-0941 |
|---|---|---|
| Ki PI3K alpha | 0.22 nM | 3.0 |
| Selectivity beta PI3K | 38x, | 11x |
| Selectivity delta PI3K | 0.4x, | 1.0x |
| Selectivity gamma PI3K | 3x | 25x |
| PI3K alpha H1047R mutant | 0.4x | 1x |
| PI3K alpha E545K mutant | 0.4x | 1x |

*Folkes et al (2008) Jour. of Med. Chem. 51(18): 5522-5532)

The phosphoinositide 3-kinase (PI3K) signaling cascade, a key mediator of cellular survival, growth, and metabolism, is frequently altered in human cancer. Activating mutations in PIK3CA, the gene which encodes the α-catalytic subunit of PI3K, occur in approximately 30% of breast cancers. These mutations result in constitutive activity of the enzyme and are oncogenic. Expression of mutant PIK3CA H1047R in the luminal mammary epithelium evokes heterogeneous tumors that express luminal and basal markers and are positive for the estrogen receptor. The PIK3CA H1047R oncogene targets a multipotent progenitor cells and recapitulates features of human breast tumors with PIK3CA H1047R (Meyer et al (2011). Cancer Res; 71(13):4344-51). Hyperactivation of PI3K can occur as a result of somatic mutations in PIK3CA, the gene encoding the p110α subunit of PI3K. The HER2 oncogene is amplified in 25% of all breast cancers and some of these tumors also harbor PIK3CA mutations. PI3K can enhance transformation and confer resistance to HER2-directed therapies. PI3K mutations E545K and H1047R introduced in MCF10A human mammary epithelial cells that also overexpress HER2 conferred a gain of function to MCF10A/HER2 cells. Aromatase-expressing MCF7 cells convert androstenedione to estrogen in culture. Expression of H1047R PI3K but not E545K PI3K markedly upregulated the HER3/HER4 ligand heregulin (HRG) (Chakrabarty et al (2010) Oncogene 29(37):5193-5203).

GDC-0032 Single Agent In Vitro Activity

The cytotoxic or cytostatic activity of GDC-0032 as a single agent was measured by: establishing a proliferating mammalian tumor cell line in a cell culture medium, adding a test compound, culturing the cells for a period from about 6 hours to about 5 days; and measuring cell viability (Example 3). Cell-based in vitro assays were used to measure viability, i.e. proliferation ($IC_{50}$), cytotoxicity ($EC_{50}$), and induction of apoptosis (caspase activation).

The in vitro potency of GDC-0032 was measured by the cell proliferation assay of Example 3; the CellTiter-Glo® Luminescent Cell Viability Assay, commercially available from Promega Corp., Madison, Wis. This homogeneous assay method is based on the recombinant expression of *Coleoptera* luciferase (U.S. Pat. No. 5,583,024; U.S. Pat. No. 5,674,713; U.S. Pat. No. 5,700,670) and determines the number of viable cells in culture based on quantitation of the ATP present, an indicator of metabolically active cells (Crouch et al (1993) J. Immunol. Meth. 160:81-88; U.S. Pat. No. 6,602, 677). The CellTiter-Glo® Assay was conducted in 96 or 384 well format, making it amenable to automated high-throughput screening (HTS) (Cree et al (1995) AntiCancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons. The extended half-life eliminates the need to use reagent injectors and provides flexibility for continuous or batch mode processing of multiple plates. This cell proliferation assay can be used with various multiwell formats, e.g. 96 or 384 well format. Data can be recorded by luminometer or CCD camera imaging device. The luminescence output is presented as relative light units (RLU), measured over time.

The anti-proliferative effects of GDC-0032, and GDC-0941 for comparison, were measured by the CellTiter-Glo® Assay (Example 3) against the tumor cell lines in FIGS. 1-4 and Table 2. $EC_{50}$ values were established for the experiments. The range of in vitro cell potency activities was about 100 nM to about 10 μM.

TABLE 2

Single agent in vitro activity of GDC-0032 in cell proliferation assays

| Cell Line | Tissue Type | Status | EC50 (μmol) GDC-0032 |
|---|---|---|---|
| IPC298 | Melanoma | NRAS Q61L | 10.000 |
| INK-134 | Glioma | Helical-HET.545E > D, HET.1043M > I | 0.976 |
| AU565 | Breast | HER2 Amplified | 0.093 |
| BT474 | Breast | HER2 Amplified | 0.084 |
| BT549 | Breast | PTEN | 1.200 |
| Cal 85-1 | Breast | WT | 0.520 |
| CAL-148 | Breast | Kinase(HET.1047H > R)/-PTEN | 0.375 |
| CAL120 | Breast | WT | 3.838 |
| CAL51 | Breast | PTEN/HET.542E > K | 0.326 |
| CAMA-1 | Breast | PTEN* | 5.621 |
| EFM-19 | Breast | Kinase-HOM.1047H > L | 0.013 |
| EVSA-T | Breast | PTEN | 1.123 |
| HCC-1143 | Breast | WT | 2.968 |
| HCC-1428 | Breast | WT | 10.000 |
| HCC-202 | Breast | Helical-HET.545E > K, HET.866L > F, HET.391I > M | 0.018 |
| HCC-70 | Breast | PTEN | 0.043 |
| HCC1954 | Breast | Kinase-HOM.1047H > L | 0.102 |
| HDQ-P1 | Breast | WT | 0.258 |
| HS 578T-1x2 | Breast | WT | 2.073 |
| KPL4 | Breast | Kinase-HET.1047H > R, HET.350D > N | 0.016 |
| MCF7-neo/HER2 | Breast | Helical-HET.545E > K | 0.178 |
| MDA-MB-436 | Breast | PTEN | 4.686 |
| MDA-MB-453 | Breast | Kinase-HET.1047H > R, HET.350D > N | 0.044 |
| MDA-MB-468 | Breast | PTEN | 7.882 |
| MFM223 | Breast | Kinase-HET.1047H > R, HET.350D > N | 0.211 |
| MX-1 | Breast | PTEN | 0.892 |
| SKBR3 | Breast | HER2 Amplified | 0.043 |
| T47D | Breast | Kinase-HET.1047H > R, HET.350D > N | 0.045 |
| EFM-192A | Breast | HET.420C > R | 0.101 |
| HCC-1419 | Breast | WT | 0.046 |
| HCC-2218 | Breast | WT | 0.090 |
| ZR75-30 | Breast | WT | 0.021 |
| HT-29 | Colon | K-RAS | 0.075 |
| SW620 | Colon | K-RAS | 10.000 |
| LS-180 | Colon | KRAS/HET.1047H > R | 0.795 |
| HCT116 | Colon | KRAS/HET.1047H > R | 0.897 |
| DLD-1 | Colon | KRAS/HET.545E > K | 2.500 |
| SW403 | Colon | KRAS/HET.546Q > K | 0.143 |
| SW948 | Colon | KRAS/HOM.542E > K | 0.062 |
| KM12 | Colon | PTEN | 4.687 |
| MDST8 | Colon | PTEN/B-Raf | 4.009 |

TABLE 2-continued

Single agent in vitro activity of GDC-0032 in cell proliferation assays

| Cell Line | Tissue Type | Status | EC50 (µmol) GDC-0032 |
|---|---|---|---|
| LN-229 | Glioma | Helical-HET.545E > K | 3.414 |
| U87MG | Glioma | PTEN | 1.019 |
| SF539 | Glioma | PTEN | 1.881 |
| SW1783 | Glioma | PTEN | 3.106 |
| U-118MG | Glioma | PTEN | 3.196 |
| G22 | Glioma | PTEN | 6.018 |
| MO59K | Glioma | PTEN/KRAS | 4.975 |
| MO59J | Glioma | PTEN/KRAS | 5.652 |
| G96 | Glioma | WT | 0.201 |
| SF268 | Glioma | WT | 1.067 |
| Detroit562 | Head/Neck | Kinase-H1047R | 0.058 |
| H838 | Lung(NSCLC) | WT | 3.101 |
| LXFL-529 | Lung(NSCLC) | Helical-HET.542E > K | 0.057 |
| H596 | Lung(NSCLC) | Helical-HET.545E > K, HET.997L > P | 0.058 |
| HOP18 | Lung(NSCLC) | K-RAS | 0.077 |
| H358 | Lung(NSCLC) | K-RAS | 0.220 |
| H292 | Lung(NSCLC) | K-RAS | 0.274 |
| SW1573 | Lung(NSCLC) | K-RAS | 0.285 |
| H2122 | Lung(NSCLC) | K-RAS | 0.366 |
| H2009 | Lung(NSCLC) | K-RAS | 0.710 |
| A549 | Lung(NSCLC) | K-RAS | 0.906 |
| EBC-1 | Lung(NSCLC) | K-RAS | 1.655 |
| H2030 | Lung(NSCLC) | K-RAS | 2.313 |
| H23 | Lung(NSCLC) | K-RAS | 2.741 |
| HOP62 | Lung(NSCLC) | K-RAS | 3.089 |
| KNS-62 | Lung(NSCLC) | K-RAS | 3.565 |
| H647 | Lung(NSCLC) | K-RAS | 9.017 |
| A427 | Lung(NSCLC) | K-RAS | 10.000 |
| Calu-6 | Lung(NSCLC) | K-RAS | 10.000 |
| H441 | Lung(NSCLC) | K-RAS | 10.000 |
| H650 | Lung(NSCLC) | K-RAS | 10.000 |
| H460 | Lung(NSCLC) | KRAS/HEt.545E > K | 0.603 |
| H1299 | Lung(NSCLC) | N-RAS | 1.725 |
| ABC-1 | Lung(NSCLC) | WT | 0.234 |
| HOP92 | Lung(NSCLC) | WT | 1.691 |
| H520 | Lung(NSCLC) | PTEN | 0.264 |
| H1781 | Lung(NSCLC) | PTEN | 0.561 |
| H1650 | Lung(NSCLC) | PTEN | 1.477 |
| H1703 | Lung(NSCLC) | WT | 0.136 |
| H322 | Lung(NSCLC) | WT | 0.280 |
| H661 | Lung(NSCLC) | WT | 0.497 |
| H1793 | Lung(NSCLC) | WT | 2.018 |
| H1568 | Lung(NSCLC) | WT | 10.000 |
| H522 | Lung(NSCLC) | WT | 10.000 |
| H417 | Lung(SC) | Helical-HET.546Q > K, HOM.391I > M | 1.279 |
| H2171 | Lung(SC) | K-RAS | 1.452 |
| H1048 | Lung(SC) | Kinase-HET.1047H > R, HET.391I > M | 0.014 |
| H82 | Lung(SC) | PTEN | 10.000 |
| 888-MEL | Melanoma | B-Raf | 10.000 |
| A375 | Melanoma | B-Raf | 10.000 |
| C32 | Melanoma | PTEN/B-Raf | 5.810 |
| A2058 | Melanoma | PTEN/B-Raf | 9.240 |
| SKOV3 | Ovarian | Kinase-HET.1047H > R, HET.350D > N | 0.076 |
| IGROV1 | Ovarian | Kinase-HET.1069O > W | 0.031 |
| FUOV1 | Ovarian | WT | 0.062 |
| Caov3 | Ovarian | WT | 4.785 |
| OVCAR3 | Ovarian | WT | 0.398 |
| EFO21 | Ovarian | PTEN | 10.000 |
| TOV21GX1 | Ovarian | PTEN/HET.1047H > Y | 10.000 |
| HPAC | Pancreatic | K-RAS | 0.645 |
| KP4x1 | Pancreatic | K-RAS | 2.940 |
| 22RV1 | Prostate | Helical-HET.546Q > R | 0.050 |
| PC3 | Prostate | PTEN | 0.864 |

Table 2 shows significant potency of GDC-0032 as a single agent activity in cell proliferation in vitro assays against PIK3CA and HER2 amplified cell lines.

Figure 1A:
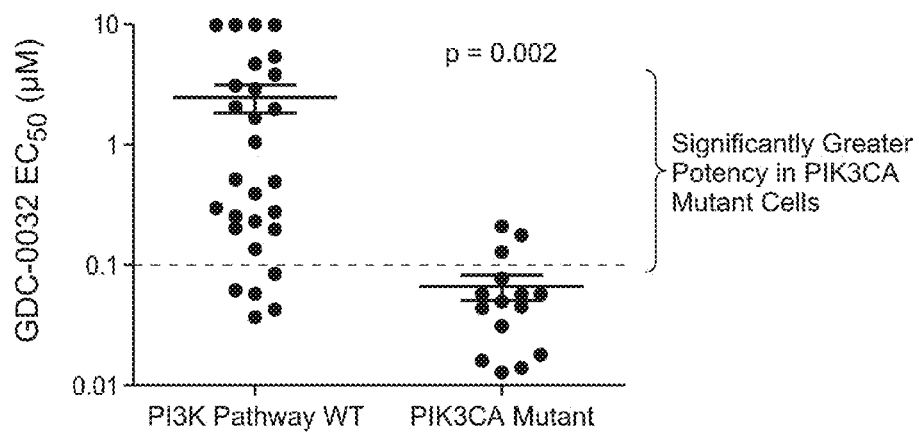
FIG. 1A shows a plot of efficacy (EC50 micromolar) of GDC-0032 in a cell proliferation (Cell-Titer Glo®, Promega) assay against PIK3CA wild type (WT) and mutant cell lines. Each dot represents a different cancer cell line.
Figure 1B:
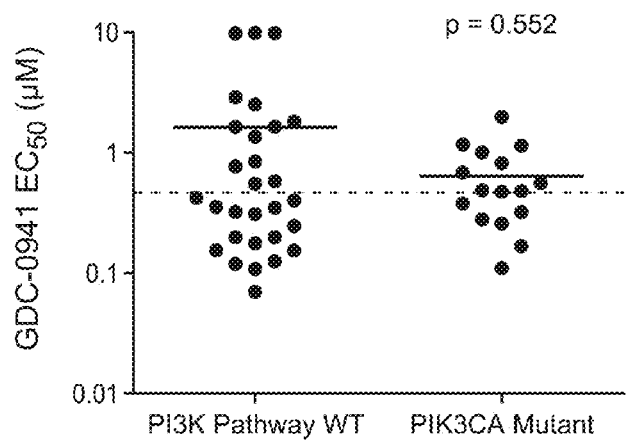
FIG. 1B shows a plot of efficacy (EC50 micromolar) of GDC-0941 (4-(2-(1H-indazol-4-yl)-6-((4-(methylsulfonyl) piperazin-1-yl)methyl)thieno[3,2-d]pyrimidin-4-yl)morpholine) in a cell proliferation (Cell-Titer Glo®, Promega) assay against PIK3CA wild type (WT) and mutant cell lines. Each dot represents a different cancer cell line.
Figure 2A:
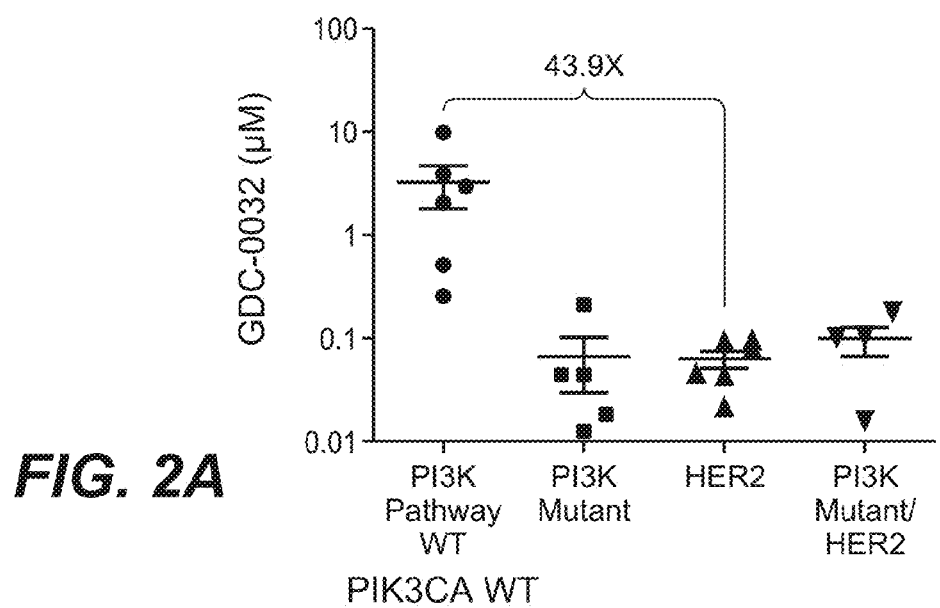
FIG. 2A shows a plot of efficacy (EC50 micromolar) of GDC-0032 in cell proliferation assays against PIK3CA wild type (WT), PIK3CA mutant, HER2 expressing, and PI3K mutant/HER2 expressing cell lines. Each dot represents a different cell line.
Figure 2B:
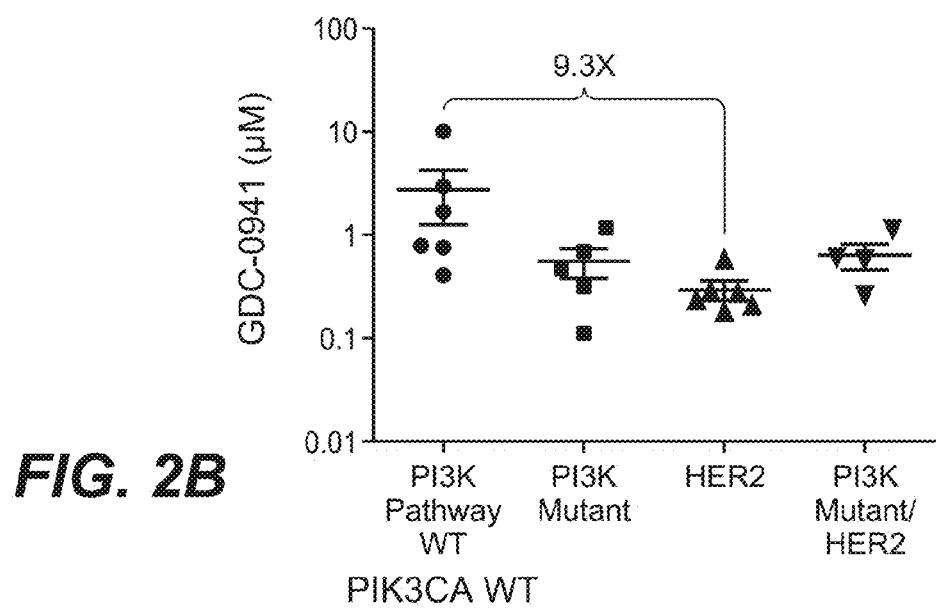
FIG. 2B shows a plot of efficacy (EC50 micromolar) of GDC-0941 in cell proliferation assays against PIK3CA wild type (WT), PIK3CA mutant, HER2 expressing, and PI3K mutant/HER2 expressing cell lines. Each dot represents a different cell line.

FIGS. 1A and 1B show two plots of efficacy (EC50 micromolar) of GDC-0032 and GDC-0941 (4-(2-(1H-indazol-4-yl)-6-((4-(methylsulfonyl)piperazin-1-yl)methyl)thieno[3,2-d]pyrimidin-4-yl)morpholine) in cell proliferation assays against PIK3CA wild type (WT) and mutant cell lines, including HCC-1954 with the H1047R mutation. FIG. 1A shows that GDC-0032 has a wider therapeutic window against PIK3CA mutant cell lines than the pan inhibitor GDC-0941 (FIG. 1B). FIGS. 2A and 2B show two plots of efficacy (EC50 micromolar) of GDC-0032 and GDC-0941 in cell proliferation assays against PIK3CA wild type (WT), PIK3CA mutant, HER2 expressing, and PI3K mutant/HER2 expressing cell lines. FIGS. 1A and 1B, and FIGS. 2A and 2B show that GDC-0032 is more potent against PIK3CA mutant cells and HER2+ breast cancer cells than GDC-0941. Cancer cell lines with HER2 amplification are about 44 times more sensitive to GDC-0032 than those without HER2 amplification, compared to 9 times more sensitive to GDC-0941.

FIG. 2A shows a plot of efficacy (EC50 micromolar) of GDC-0032 in cell proliferation assays against PIK3CA wild type (WT), PIK3CA mutant, HER2 expressing, and PI3K mutant/HER2 expressing cell lines. Each dot represents a different cell line.

FIG. 2B shows a plot of efficacy (EC50 micromolar) of GDC-0941 in cell proliferation assays against PIK3CA wild type (WT), PIK3CA mutant, HER2 expressing, and PI3K mutant/HER2 expressing cell lines. Each dot represents a different cell line.

Figure 3A:
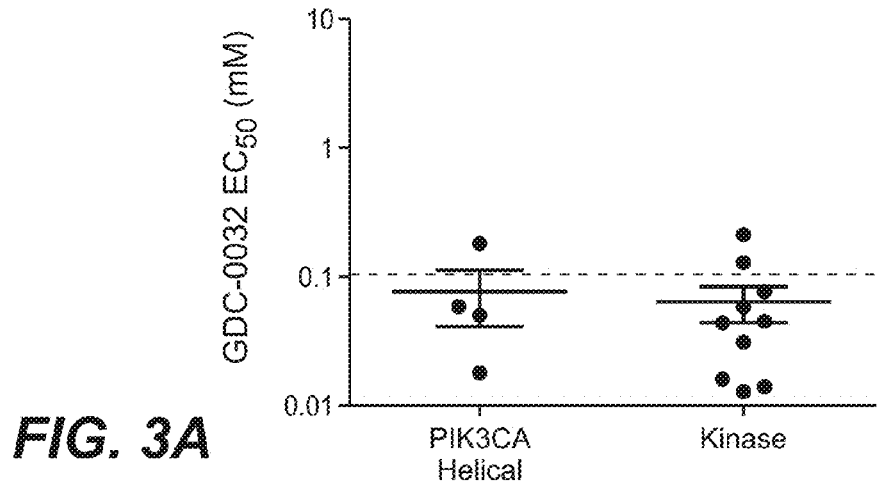
FIG. 3 shows three plots of efficacy (EC50 micromolar) of GDC-0032 against: (3a, top) PIK3CA helical and kinase domain mutant cell lines; (3b, middle) PIK3CA wild type, PIK3CA mutant, PTEN null, and PTEN/PIK3CA mutant cell lines; and (3c, bottom) PIK3CA wild type, PIK3CA mutant, Ras mutant, and Ras/PIK3CA mutant cell lines in 4 day Cell-Titer Glo® viability assays. Each dot represents a different cell line.
Figure 3B:
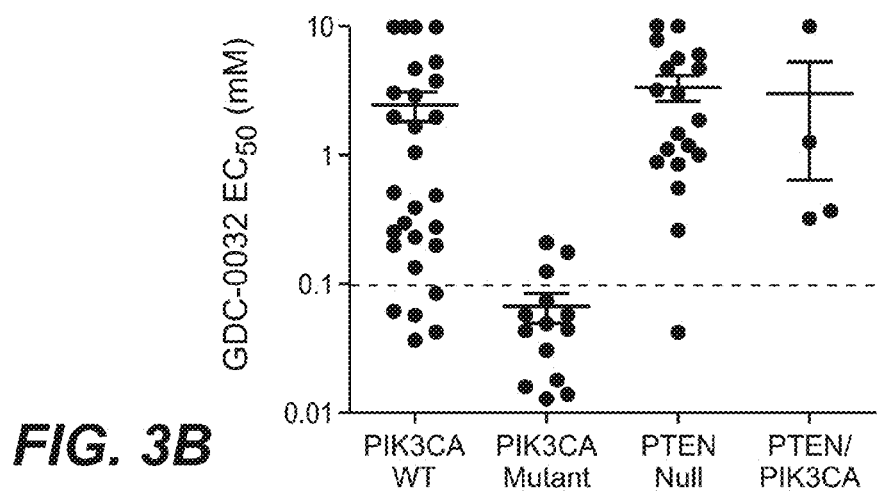
Figure 3C:
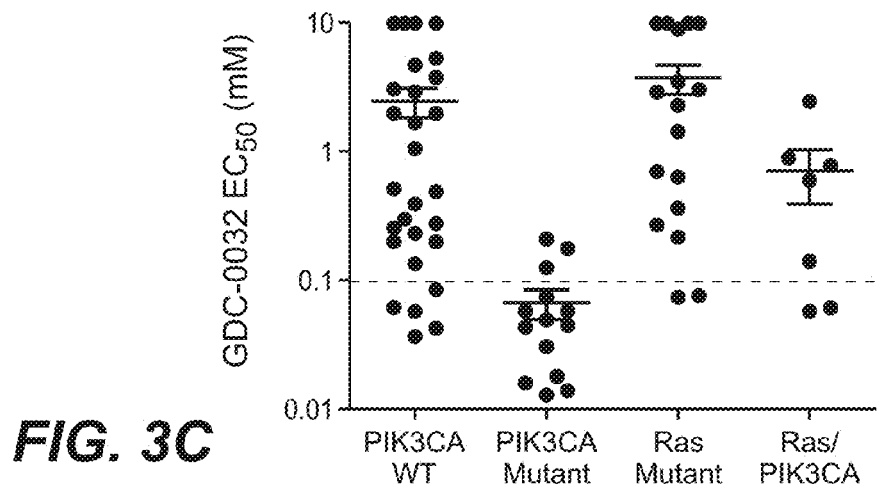

FIG. 3 shows three plots of efficacy (EC50 micromolar) of GDC-0032 against: (3a, top) helical and kinase domain mutant cell lines; (3b, middle) PI3K pathway wild type, PIK3CA mutant, PTEN null, and PTEN/PIK3CA cell lines; and (3c, bottom) PI3K pathway wild type, PIK3CA mutant, Ras mutant, and Ras/PIK3CA mutant cell lines. The results show that GDC-0032 is less effective when PIK3CA mutant tumors have co-mutations in Ras or loss of PTEN.

Figure 4A:
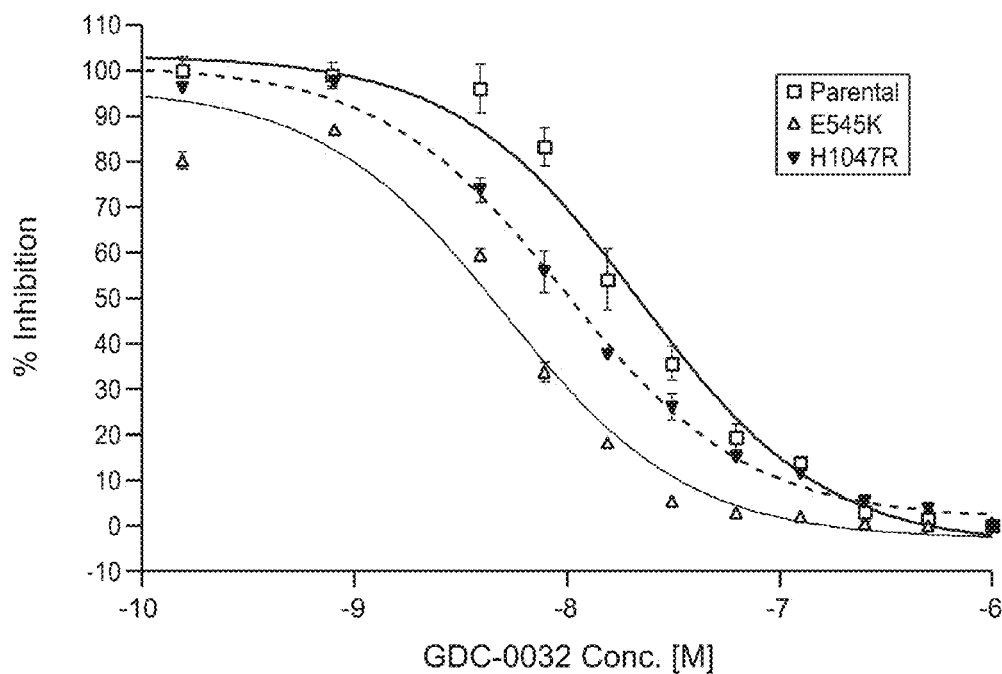
FIG. 4a shows the potency of GDC-0032 in an SW48 isogenic cell line set. SW48 parental cells and knock-in mutant subclones harboring common PIK3CA hotspot mutations E545K or H1047R were obtained from Horizon Discovery. GDC-0032 EC50 viability values were determined in these lines using a four day CellTiter-Glo® assay.

FIG. 4a shows the potency of GDC-0032 in an SW48 isogenic cell line set. SW48 parental and knock-in mutant subclones harboring common PI3K hotspot mutations E545K or H1047R were obtained from Horizon Discovery and GDC-0032 EC50 viability values were determined in these lines using a four day CellTiter-Glo (Promega) assay. Viability EC50 values for the three cell subtypes were 0.022 µM parental, 0.005 µM E545K, and 0.008 µM H1047R. Taken together, isogenic cell lines with PI3K mutations demonstrate increased sensitivity to GDC-0032.

Figure 4B:
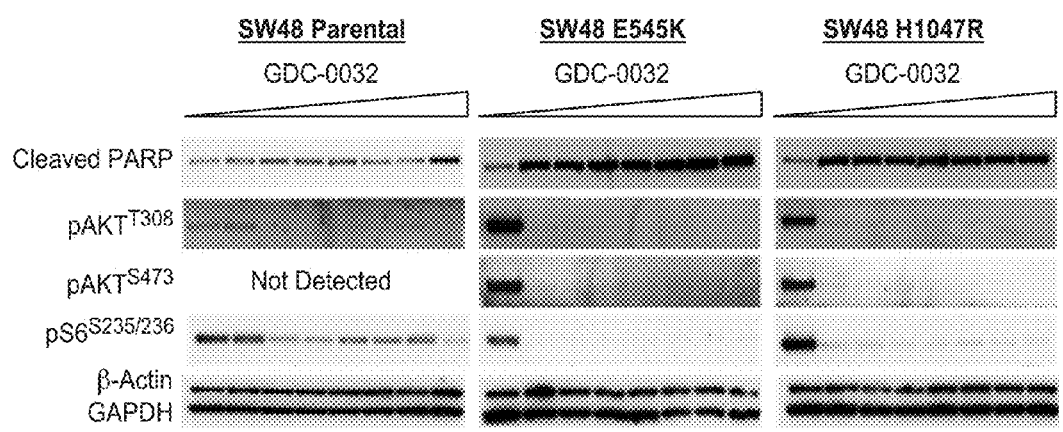
FIG. 4b shows western blot autoradiograms of gel electrophoresis of cell lysates collected after 18 hours of GDC-0032 exposure at a range of concentrations in the SW48 isogenic cells; parental and PIK3CA knock-in mutants E545K and H1047R.

FIG. 4b shows autoradiograms of gel electrophoresis of lysates collected 18 hours post dosing of the SW48 isogenic cells; parental and PI3K mutant knock-in mutants E545K and H1047R. GDC-0032 induces apoptosis in cells harboring PI3K mutations at very low compound concentrations. Similar effects were observed in PI3K mutant isogenic cells from MCF10 breast cell line and HCC-1954 (PI3K H1047R mutant breast cancer cell line).

GDC-0032 and Chemotherapeutic Combination In Vitro Activity

The cytotoxic or cytostatic activity of combinations of GDC-0032 and exemplary chemotherapeutic agents was measured by: establishing a proliferating mammalian tumor cell line in a cell culture medium, adding a test compound, culturing the cells for a period from about 6 hours to about 5 days; and measuring cell viability (Example 3). Cell-based in vitro assays were used to measure viability, i.e. proliferation ($IC_{50}$), cytotoxicity ($EC_{50}$), and induction of apoptosis (caspase activation).

The in vitro potency of the combinations of GDC-0032 with chemotherapeutic agents was measured by the cell proliferation assay of Example 3; the CellTiter-Glo® Luminescent Cell Viability Assay, commercially available from Promega Corp., Madison, Wis. This homogeneous assay method is based on the recombinant expression of *Coleoptera* luciferase (U.S. Pat. No. 5,583,024; U.S. Pat. No. 5,674,713; U.S. Pat. No. 5,700,670) and determines the number of viable cells in culture based on quantitation of the ATP present, an indicator of metabolically active cells (Crouch et al (1993) J. Immunol. Meth. 160:81-88; U.S. Pat. No. 6,602,677). The CellTiter-Glo® Assay was conducted in 96 or 384 well format, making it amenable to automated high-throughput screening (HTS) (Cree et al (1995) AntiCancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing.

The anti-proliferative effects of combinations of GDC-0032 and chemotherapeutic agents were measured by the CellTiter-Glo® Assay (Example 3) against the tumor cell lines in FIGS. 5-12. $EC_{50}$ values were established for the tested compounds and combinations. The range of in vitro cell potency activities was about 100 nM to about 10 µM.

The individual measured EC50 values of GDC-0032 and of the chemotherapeutic agent against the particular cell are compared to the combination EC50 value. The combination index (CI) score is calculated by the Chou and Talalay method (Chou, T. and Talalay, P. (1984) Adv. Enzyme Regul. 22:27-55). A CI less than about 0.7 indicates synergy. A CI between 0.8 and 1.2 indicates additivity. A CI greater than 1.2 indicates antagonism. The strength of synergy is assessed according to Chou and Talalay. Certain therapeutic combinations in FIGS. 4-6 show the surprising and unexpected property of synergy in the in vitro cell proliferation assays with tumor type cell lines including non-Hodgkin's lymphoma (NHL), diffuse large B-cell lymphoma (DLBCL), and multiple myeloma. Other combinations show no synergy; and only show mere additivity or antagonism. Certain combinations are synergistic with one or more tumor types, but not others. The synergy demonstrated in the in vitro cell proliferation assays provides a basis to expect a corresponding synergy in treating cancer in human patients.

Figure 5A:
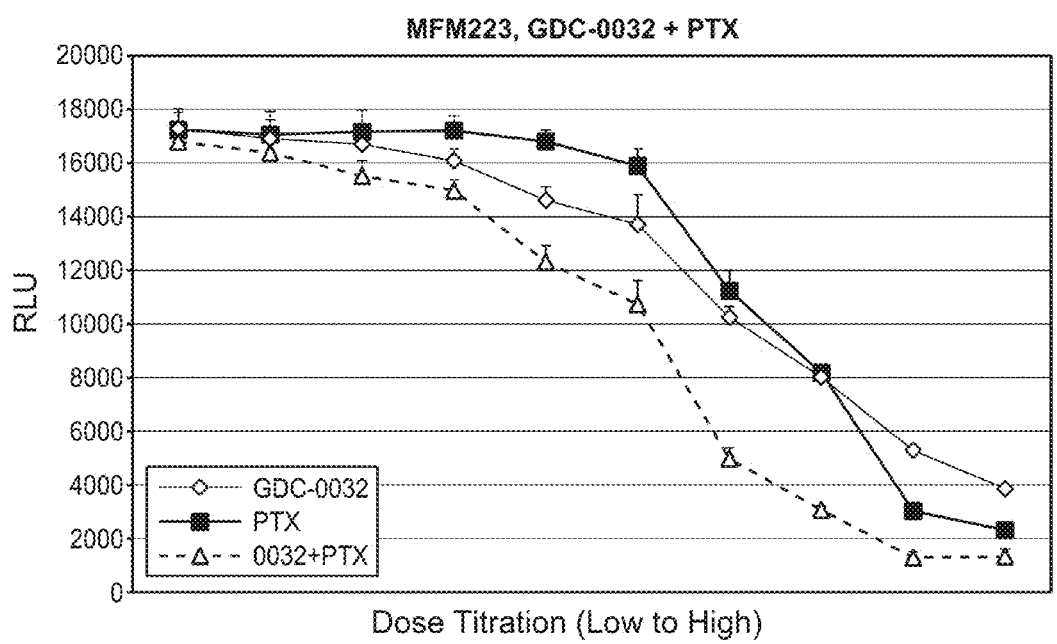
FIG. 5a shows the effect of GDC-0032, paclitaxel (PTX), and the combination of GDC-0032 and paclitaxel on breast cancer cell line MFM223 with PIK3CA H1047R, and D350N. An in vitro assay (Cell-Titer Glo®, Promega) measured viable cells (RLU=Relative Light Units) over varying inhibitor concentrations by 2-fold dose titration of GDC-0032, paclitaxel (PTX), and the combination of GDC-0032 and paclitaxel.

FIG. 5a shows the effect of GDC-0032, paclitaxel (PTX), and the combination of GDC-0032 and paclitaxel on breast cancer cell line MFM223 with H1047R, and D350N mutations. An in vitro cell survival and proliferation assay (Cell-Titer Glo, Promega) measured viable cells over varying inhibitor concentrations by dose titration (RLU=Relative Light Units) of GDC-0032, paclitaxel (PTX), and the combination of GDC-0032 and paclitaxel. When the two drugs were combined a marked improvement in cell viability inhibition is observed.

Figure 5B:
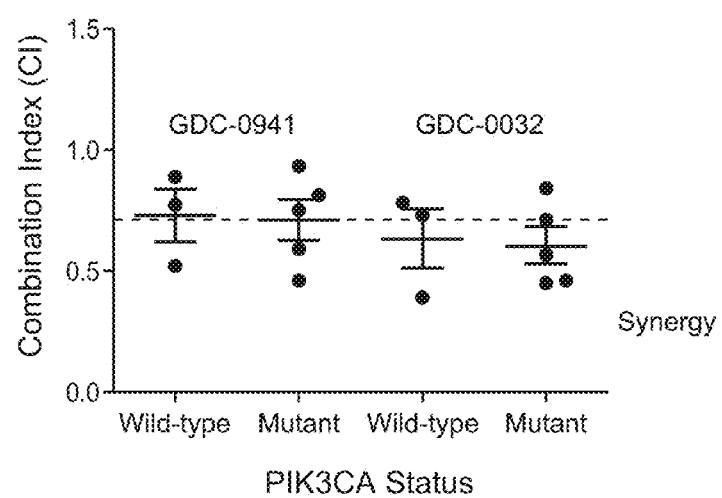
FIG. 5b shows the Combination Indices (CI) of GDC-0032+paclitaxel and GDC-0941+paclitaxel combinations against PIK3CA wild type and mutant breast cancer cell lines of both the basal and luminal types. PIK3CA mutations include E545K and H1047R. A CI value below about 0.7 indicates synergy. Each dot represents a cancer cell line.

FIG. 5b shows the Combination Indices (CI) of GDC-0032+paclitaxel and GDC-0941+paclitaxel combinations against PIK3CA wild type and mutant breast cancer cell lines of both the basal and luminal types. PIK3CA mutations include E545K and H1047R. A CI value below about 0.7 indicates synergy. Each dot represents a cancer cell line. The results show similar trends for the activity of the two combinations against the PIK3CA wild type and mutant breast cancer cell lines.

Figure 6A:
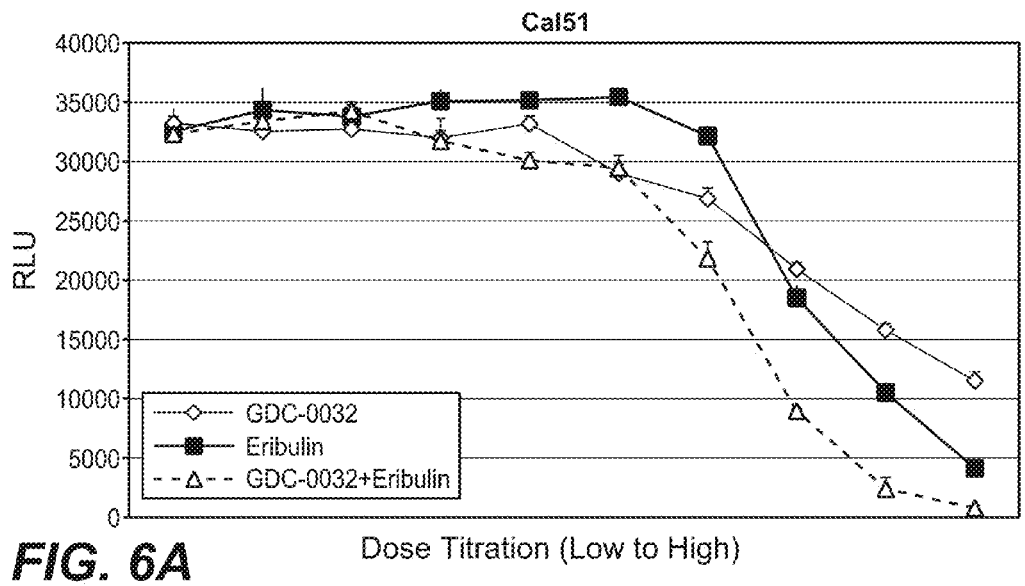
FIG. 6a shows the effect of GDC-0032, eribulin, and the combination of GDC-0032 and eribulin on basal breast cancer cell line Cal51 with PIK3CA E542K mutation and PTEN loss. An in vitro cell survival and proliferation assay (Cell-Titer Glo®, Promega) measured viable cells (RLU=Relative Light Units) over varying inhibitor concentrations by 2-fold dose titration of GDC-0032, eribulin, and the combination of GDC-0032 and eribulin.

FIG. 6a shows the effect of GDC-0032, eribulin, and the combination of GDC-0032 and eribulin on breast cancer cell line Cal51 with E542K PIK3CA mutation and loss of PTEN protein expression of the basal subtype. An in vitro cell survival and proliferation assay (Cell-Titer Glo, Promega) measured viable cells over varying inhibitor concentrations by dose titration (RLU=Relative Light Units) of GDC-0032, eribulin, and the combination of GDC-0032 and eribulin. When the two drugs were combined a marked improvement in cell viability inhibition is observed.

Figure 6B:
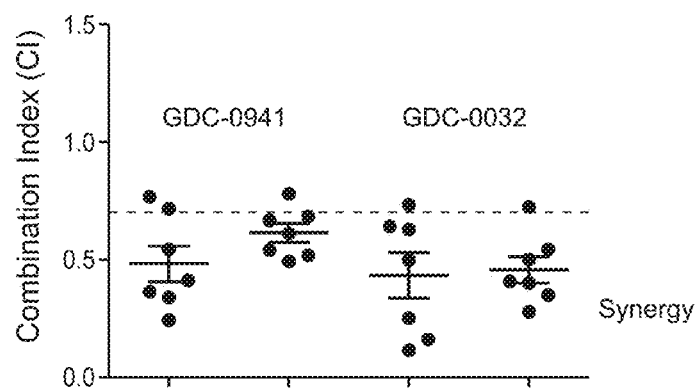
FIG. 6b shows the Combination Indices (CI) of GDC-0032+eribulin, GDC-0032+docetaxel, GDC-0941+eribulin, and GDC-0941+docetaxel combinations against breast cancer cell lines of both the basal and luminal types. A CI value below about 0.7 indicates synergy. Each dot represents a breast cancer cell line.

FIG. 6b shows the Combination Indices (CI) of GDC-0032+eribulin, GDC-0032+docetaxel, GDC-0941+eribulin, and GDC-0941+docetaxel combinations against PIK3CA wild type, and E545K, H1047R, PTEN negative, and PTEN neg/E542K mutant breast cancer cell lines of both the basal and luminal types. A CI value below about 0.7 indicates synergy. Each dot represents a cancer cell line. Synergy was observed for these combinations in the majority of evaluated cell lines.

Figure 7:
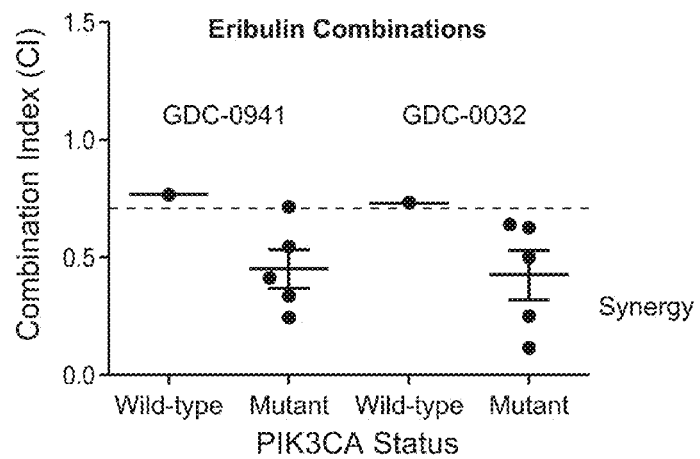
FIG. 7 shows the Combination Indices (CI) of GDC-0032+eribulin and GDC-0941+eribulin combinations against PIK3CA wild type, and PIK3CA E545K, H1047R mutant breast cancer cell lines of both the basal and luminal types. A CI value below about 0.7 indicates synergy. Each dot represents a cancer cell line.

FIG. 7 shows the Combination Indices (CI) of GDC-0032+eribulin and GDC-0941+eribulin combinations against PIK3CA wild type, and E545K, H1047R PIK3CA mutant breast cancer cell lines of both the basal and luminal types. A CI value below about 0.7 indicates synergy. Each dot represents a cancer cell line. Synergy was observed for these combinations in the majority of evaluated cell lines.

TABLE 3

In vitro activity of GDC-0032 + chemotherapeutic second agent combinations in cell proliferation assays

| Cell Line | Tumor Type | Gene Mutations | Chemo. Second agent | CI EC50 (μmol) | HER2 | Basal/ Luminal |
|---|---|---|---|---|---|---|
| CAL-120 | Breast | | 5-FU | 0.8 | | Basal |
| CAL-85-1 | Breast | | 5-FU | 0.75 | | Basal |
| CAMA-1 | Breast | | 5-FU | 1.01 | | Luminal |
| EFM-19 | Breast | PI3K H1047L | 5-FU | 0.73 | | Luminal |
| EVSA-T | Breast | PTEN neg | 5-FU | 1.19 | | Luminal |
| HCC-1143 | Breast | | 5-FU | 0.94 | | Basal |
| HCC-1395 | Breast | | 5-FU | 0.55 | | Basal |
| HCC-1419 | Breast | | 5-FU | 0.91 | Her2 | |
| HCC-1428 | Breast | | 5-FU | 0.42 | | Luminal |
| HCC-1500 | Breast | | 5-FU | 1.28 | | Luminal |
| HCC-70 | Breast | PTEN neg | 5-FU | 1.14 | | Basal |
| HCC1954 | Breast | PI3K H1047R | 5-FU | 0.92 | Her2 | |
| HDQ-P1 | Breast | | 5-FU | 0.76 | | Basal |
| Hs578T | Breast | N-RAS | 5-FU | 0.95 | | Basal |
| KPL4 | Breast | PI3K H1047R | 5-FU | 0.33 | Her2 | |
| MCF7.1-neo/HER2 | Breast | PI3K E545K | 5-FU | 0.6 | Her2 | |
| MDA-MB-436 | Breast | PTEN neg | 5-FU | 0.31 | | Basal |
| MDA-MB-453 | Breast | PI3K H1047R | 5-FU | 0.61 | | Luminal |
| MFM-223 | Breast | PI3K H1047R | 5-FU | 0.59 | | Luminal |
| SKBR3 | Breast | | 5-FU | 0.6 | Her2 | |
| T47D | Breast | PI3K H1047R | 5-FU | 0.49 | | Luminal |
| ZR75-1 | Breast | PTEN neg | 5-FU | 0.55 | | Luminal |
| Cal51 | Breast | PI3K E542K/ PTEN neg | Docetaxel | 0.5 | | Basal |
| HCC-1954 | Breast | PI3K H1047R | Docetaxel | 0.56 | Her2 | |
| HCC-1954 | Breast | PI3K H1047R | Docetaxel | 0.407 | Her2 | |
| Hs578T | Breast | N-RAS | Docetaxel | 0.44 | | Basal |
| Hs578Tx1 | Breast | | Docetaxel | 0.542 | | Basal |
| KPL4 | Breast | PI3K H1047R | Docetaxel | 0.348 | Her2 | |
| MCF7 | Breast | PI3K E545K | Docetaxel | 0.72 | | Luminal |
| MCF7.1-neo/HER2 | Breast | PI3K E545K | Docetaxel | 0.63 | Her2 | |
| MCF7.1-neo/HER2 | Breast | PI3K E545K | Docetaxel | 0.277 | Her2 | |
| MX-1 | Breast | PTEN neg | Docetaxel | 0.401 | | Basal |
| SKOV3 | Ovarian | PI3K H1047R | Docetaxel | 0.54 | | |
| MCF7 | Breast | PI3K E545K | Doxorubicin | 0.37 | | Luminal |
| Cal51 | Breast | PI3K E542K/ PTEN neg | Eribulin | 0.626 | | Basal |
| HCC-1954 | Breast | PI3K H1047R | Eribulin | 0.497 | Her2 | |
| Hs578Tx1 | Breast | | Eribulin | 0.729 | | Basal |
| KPL4 | Breast | PI3K H1047R | Eribulin | 0.25 | Her2 | |
| MCF7 | Breast | PI3K E545K | Eribulin | 0.64 | | Luminal |
| MCF7.1-neo/HER2 | Breast | PI3K E545K | Eribulin | 0.115 | Her2 | |
| MX-1 | Breast | PTEN neg | Eribulin | 0.161 | | Basal |
| A549 | NSCLC | K-RAS G12S | GDC-0623 (MEKi) | 0.15 | | |
| H2122 | NSCLC | K-RAS G12C | GDC-0623 (MEKi) | 0.11 | | |
| HCT-116 | Colon | PI3K H1047R/ K-RAS G12D | GDC-0623 (MEKi) | 0.08 | | |
| HT29 | NSCLC | BRAF V600E | GDC-0623 (MEKi) | 0.25 | | |
| HCT-116 | Colon | PI3K H1047R/ K-RAS G12D | GDC-0973 (MEKi) | 0.08 | | |
| HDQ-P1 | Breast | | Gemcitabine | 0.57 | | Basal |
| Hs578T | Breast | N-RAS | Gemcitabine | 0.95 | | Basal |
| MDA-MB-436 | Breast | PTEN neg | Gemcitabine | 0.48 | | Basal |
| MDA-MB-453 | Breast | PI3K H1047R | Gemcitabine | 0.64 | | Luminal |
| MFM-223 | Breast | PI3K H1047R | Gemcitabine | 0.55 | | Luminal |
| SKOV3 | Ovarian | PI3K H1047R | Gemcitabine | 0.78 | | |

TABLE 3-continued

In vitro activity of GDC-0032 + chemotherapeutic second agent combinations in cell proliferation assays

| Cell Line | Tumor Type | Gene Mutations | Chemo. Second agent | CI EC50 (μmol) | HER2 | Basal/ Luminal |
|---|---|---|---|---|---|---|
| T47D | Breast | PI3K H1047R | Gemcitabine | 0.44 | | Luminal |
| BT474 | Breast | | trastuzumab | 0.57 | Her2 | |
| KPL4 | Breast | PI3K H1047R | trastuzumab | 0.48 | Her2 | |
| MCF7.1-neo/HER2 | Breast | PI3K E545K | trastuzumab | 0.96 | Her2 | |
| SKBR3 | Breast | | trastuzumab | 0.49 | Her2 | |
| Cal120 | Breast | | paclitaxel | 0.78 | | Basal |
| Cal148 | Breast | PI3K H1047R | paclitaxel | 0.71 | | ? |
| EFM19 | Breast | PI3K H1047R | paclitaxel | 0.84 | | Luminal |
| HDQ-P1 | Breast | | paclitaxel | 0.73 | | Basal |
| Hs578Tx1 | Breast | N-RAS | paclitaxel | 0.39 | | Basal |
| MCF7 | Breast | PI3K E545K | paclitaxel | 0.45 | | |
| MFM223 | Breast | PI3K H1047R | paclitaxel | 0.46 | | Luminal |
| T47D | Breast | PI3K H1047R | paclitaxel | 0.57 | | Luminal |
| BT474 | Breast | trastuzumab-resistant | pertuzumab | 0.64 | Her2 | |
| KPL4 | Breast | PI3K H1047R | pertuzumab | 0.63 | Her2 | |
| KPL4 | Breast | PI3K H1047R | T-DM1 | 0.62 | Her2 | |
| MCF7.1-neo/HER2 | Breast | PI3K E545K | T-DM1 | 0.25 | Her2 | |
| SKBR3 | Breast | | T-DM1 | 0.49 | Her2 | |
| BT474 | Breast | trastuzumab-resistant | T-DM1 | 0.57 | Her2 | |

Table 3 shows that synergy is observed for GDC-0032 in combination with several different chemotherapy drugs and targeted agents.

GDC-0032 showed superior synergy (CI 0.25) than GDC-0941 (CI 0.39) in combination with trastuzumab emtansine (T-DM1) against MCF7.1-neo/HER2 breast cancer cells with E545K PIK3CA mutation.

Figure 8A:
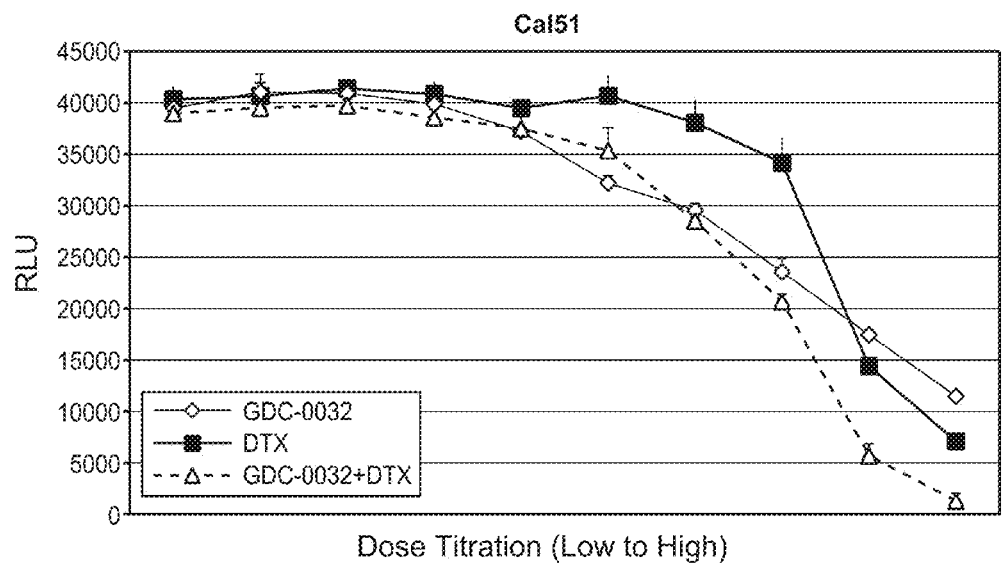
FIG. 8a shows the effect of GDC-0032, docetaxel, and the combination of GDC-0032+docetaxel on basal breast cancer cell line Cal51 with PIK3CA E542K mutation and PTEN null. An in vitro assay (Cell-Titer Glo®, Promega) measured viable cells (RLU=Relative Light Units) over varying inhibitor concentrations by dose titration of GDC-0032, docetaxel, and the combination of GDC-0032+docetaxel.

FIG. 8a shows the effect of GDC-0032, docetaxel, and the combination of GDC-0032+docetaxel on breast cancer cell line Cal51 with E542K mutation and loss of PTEN protein expression of the basal subtype. An in vitro cell survival and proliferation assay (Cell-Titer Glo®, Promega) measured viable cells over varying inhibitor concentrations by dose titration (RLU=Relative Light Units) of GDC-0032, docetaxel, and the combination of GDC-0032+docetaxel. When the two drugs were combined a marked improvement in cell viability inhibition is observed.

Figure 8B:
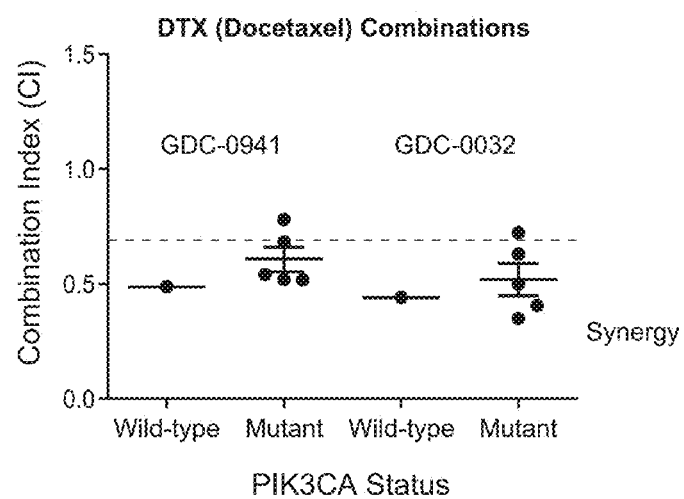
FIG. 8b shows the Combination Indices (CI) of GDC-0032+docetaxel and GDC-0941+docetaxel combinations against PIK3CA wild type and mutant breast cancer cell lines. A CI value below about 0.7 indicates synergy. Each dot represents a cancer cell line.

FIG. 8b shows the Combination Indices (CI) of GDC-0032+docetaxel and GDC-0941+docetaxel combinations against PIK3CA wild type and mutant breast cancer cell lines. A CI value below about 0.7 indicates synergy. Each dot represents a different cell line. Synergy was observed with this combination in the majority of evaluated cell lines.

Figure 9A:
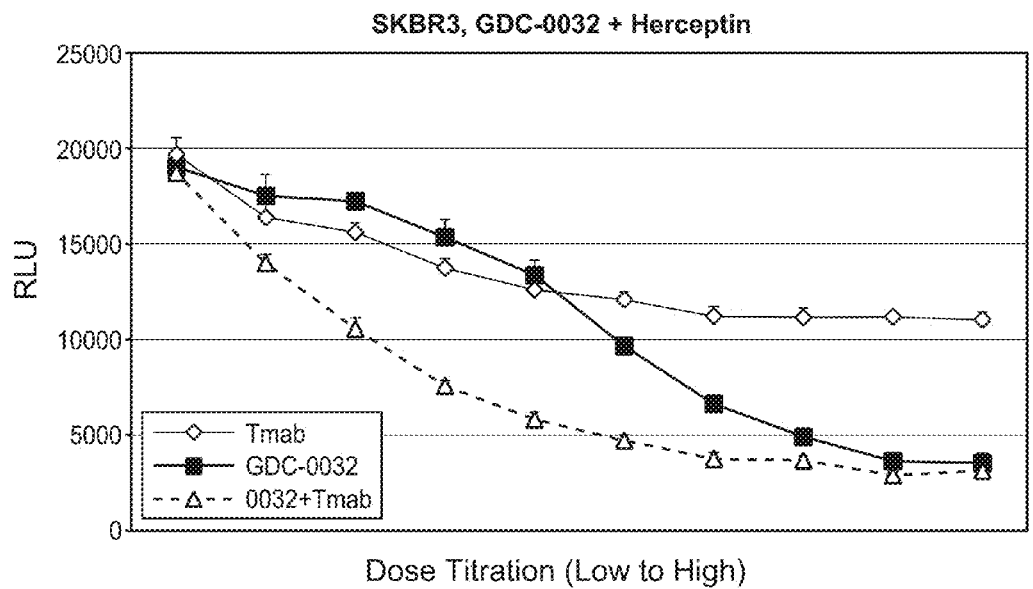
FIG. 9a shows the effect of GDC-0032, trastuzumab, and the combination of GDC-0032+trastuzumab on breast cancer cell line SKBR3 with high HER2 expression. An in vitro cell survival and proliferation assay (Cell-Titer Glo®, Promega) measured viable cells (RLU=Relative Light Units) over varying inhibitor concentrations by dose titration of GDC-0032, trastuzumab, and the combination of GDC-0032+trastuzumab.

FIG. 9a shows the effect of GDC-0032, trastuzumab, and the combination of GDC-0032+trastuzumab on breast cancer cell line SKBR3 with high HER2 expression. An in vitro cell survival and proliferation assay (Cell-Titer Glo®, Promega) measured viable cells over varying inhibitor concentrations by dose titration (RLU=Relative Light Units) of GDC-0032, trastuzumab, and the combination of GDC-0032+trastuzumab. When the two drugs were combined a marked improvement in cell viability inhibition is observed.

Figure 9B:
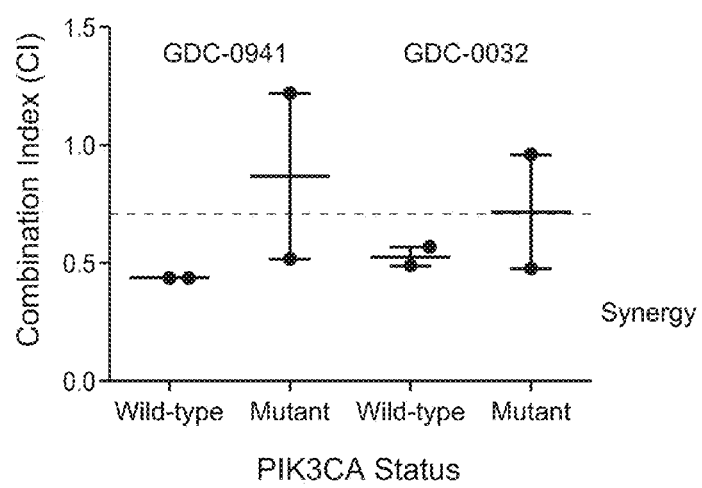
FIG. 9b shows the Combination Indices (CI) of GDC-0032+docetaxel and GDC-0941+docetaxel combinations against HER2+ PIK3CA wild type and PIK3CA mutant breast cancer cell lines including E545K and H1047R. A CI value below about 0.7 indicates synergy. Each dot represents a cancer cell line.

FIG. 9b shows the Combination Indices (CI) of GDC-0032+docetaxel and GDC-0941+docetaxel combinations against HER2+ PIK3CA wild type and mutant breast cancer cell lines including E545K and H1047R. A CI value below about 0.7 indicates synergy. Each dot represents a different cell line. Synergy was observed with this combination in the majority of evaluated cell lines.

Figure 10A:
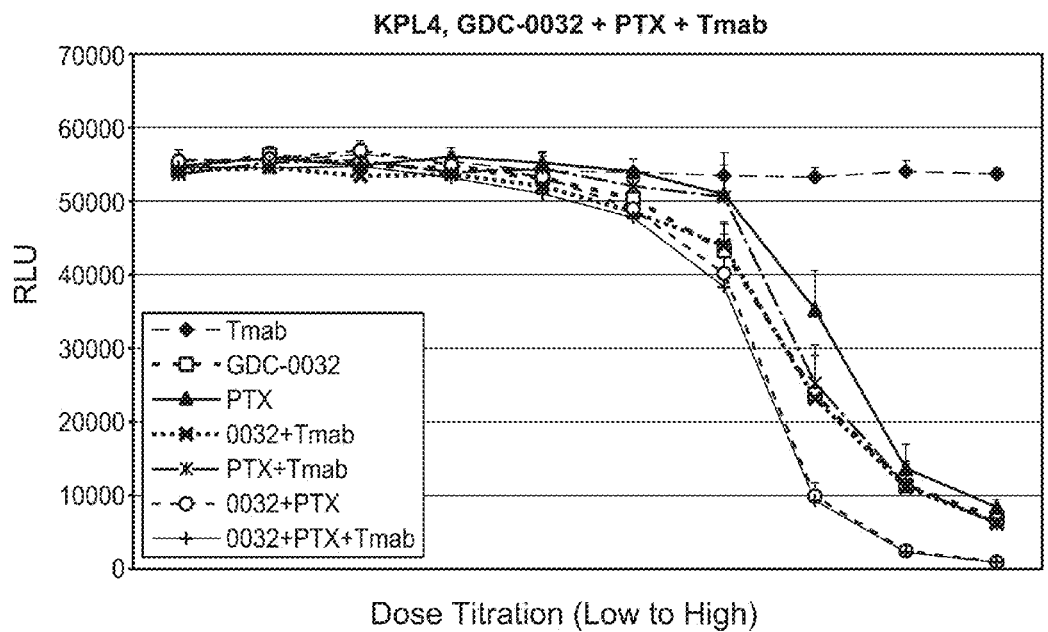
FIG. 10a shows the effects of trastuzumab, GDC-0032, paclitaxel, and the combinations of GDC-0032+trastuzumab, paclitaxel+trastuzumab, GDC-0032+paclitaxel, and triple combination GDC-0032+paclitaxel+trastuzumab on breast cancer cell line KPL4 with HER2, PIK3CA H1047R and D350N. An in vitro cell survival and proliferation assay (Cell-Titer Glo®, Promega) measured viable cells (RLU=Relative Light Units) over varying inhibitor concentrations by dose titration.

FIG. 10a shows the effects of trastuzumab, GDC-0032, paclitaxel, and the combinations of GDC-0032+trastuzumab, paclitaxel+trastuzumab, GDC-0032+paclitaxel, and triple combination GDC-0032+paclitaxel+trastuzumab on breast cancer cell line KPL4 with H1047R and D350N PIK3CA mutations. An in vitro cell survival and proliferation assay (Cell-Titer Glo, Promega) measured viable cells over varying inhibitor concentrations by dose titration (RLU=Relative Light Units). The combination of paclitaxel+GDC-0032 decreased cell viability. Trastuzumab in this combination did not have an effect on cell viability in this cell line.

Figure 10B:
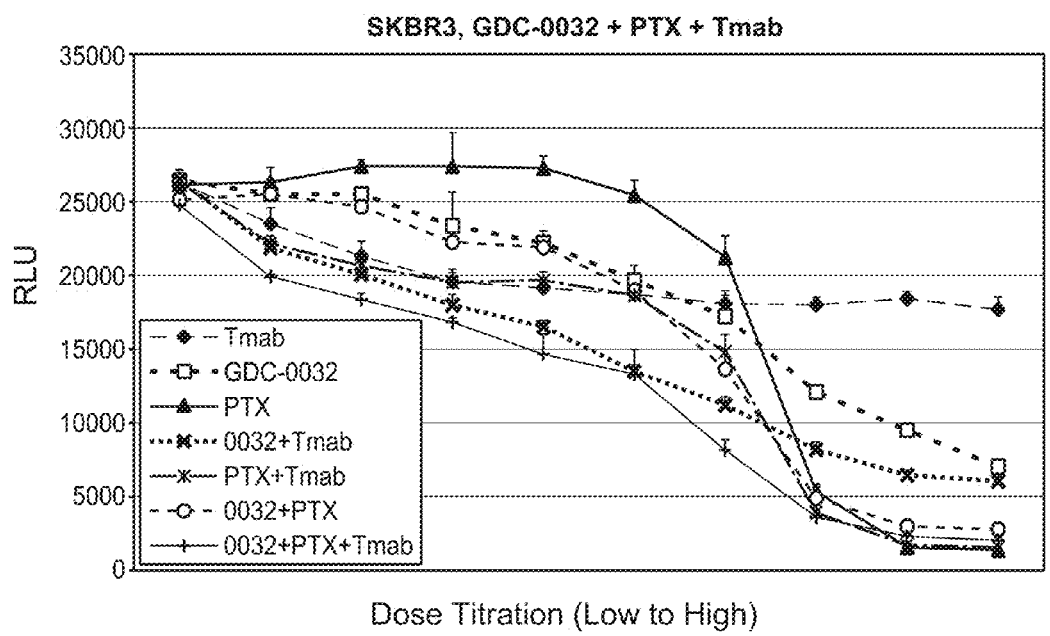
FIG. 10b shows the effect of trastuzumab, GDC-0032, paclitaxel, and the combinations of GDC-0032+trastuzumab, paclitaxel+trastuzumab, GDC-0032+paclitaxel, and GDC-0032+paclitaxel+trastuzumab on breast cancer cell line SKBR3 with high HER2 expression. An in vitro cell survival and proliferation assay (Cell-Titer Glo®, Promega) measured viable cells over varying inhibitor concentrations by dose titration (RLU=Relative Light Units).

FIG. 10b shows the effect of trastuzumab, GDC-0032, paclitaxel, and the combinations of GDC-0032+trastuzumab, paclitaxel+trastuzumab, GDC-0032+paclitaxel, and GDC-0032+paclitaxel+trastuzumab on breast cancer cell line SKBR3 with high HER2 expression. An in vitro cell survival and proliferation assay (Cell-Titer Glo, Promega) measured viable cells over varying inhibitor concentrations by dose titration (RLU=Relative Light Units). A marked improvement in decreased cell viability was observed with double and triple combinations in this cell line.

Figure 11A:
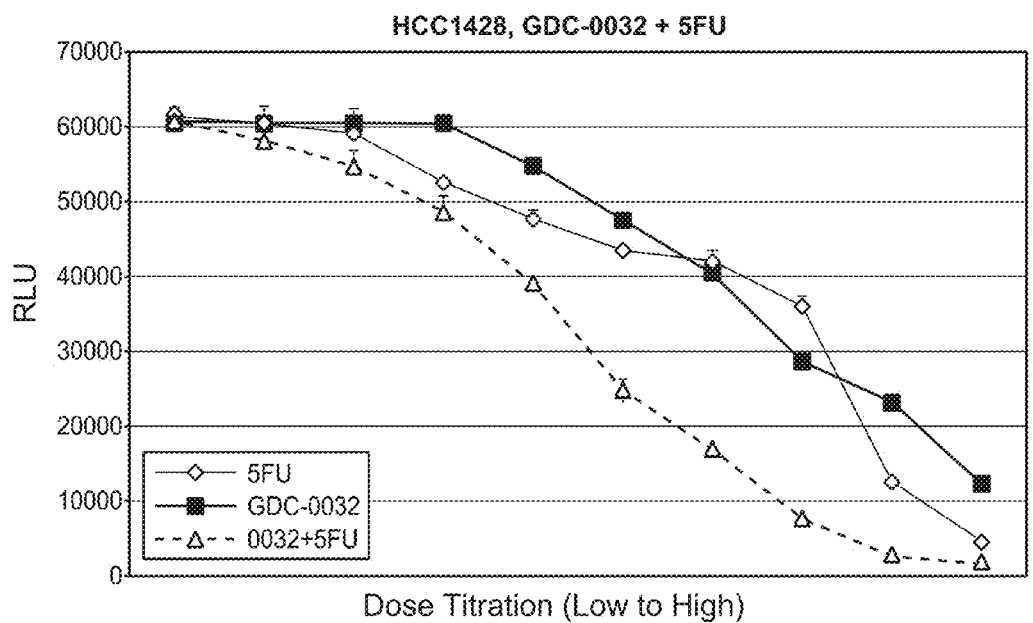
FIG. 11a shows the effect of 5-FU, GDC-0032, and the combination of 5-FU and GDC-0032 on ER+ breast cancer cell line HCC1428. An in vitro cell survival and proliferation assay (Cell-Titer Glo®, Promega) measured viable cells over varying inhibitor concentrations by dose titration (RLU=Relative Light Units) of 5-FU, GDC-0032, and the combination of 5-FU+GDC-0032.

FIG. 11a shows the effect of 5-FU, GDC-0032, and the combination of 5-FU and GDC-0032 on breast cancer cell line HCC1428. An in vitro cell survival and proliferation assay (Cell-Titer Glo, Promega) measured viable cells over varying inhibitor concentrations by dose titration (RLU=Relative Light Units) of 5-FU, GDC-0032, and the combination of 5-FU+GDC-0032. When the two drugs were combined in this cell line a marked improvement in cell viability inhibition was observed.

Figure 11B:
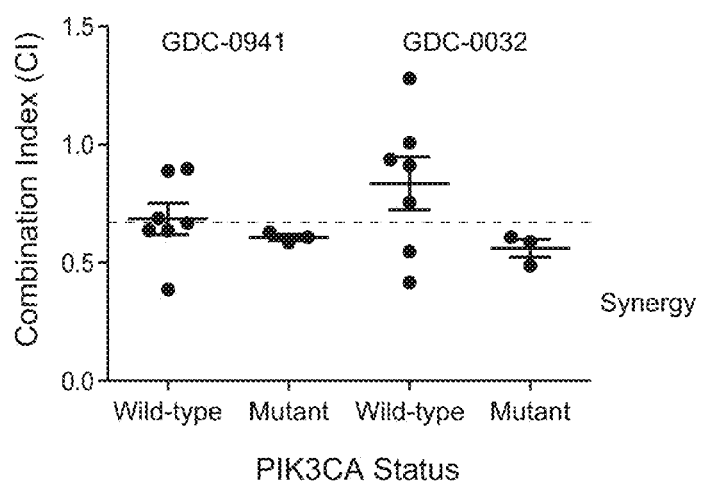
FIG. 11b shows the Combination Indices (CI) of GDC-0032+5-FU and GDC-0941+5-FU combinations against HER2+(HER2 positive) PIK3CA wild type and mutant breast cancer cell lines including E545K and H1047R of the basal and luminal subtypes. A CI value below about 0.7 indicates synergy. Each dot represents a cancer cell line.

FIG. 11b shows the Combination Indices (CI) of GDC-0032+5-FU and GDC-0941+5-FU combinations against HER2+ PIK3CA wild type and mutant breast cancer cell lines including E545K and H1047R of the basal and luminal subtypes. A CI value below about 0.7 indicates synergy. Each dot represents a different cell line. Synergy was observed with this combination in several of the evaluated cell lines.

Figure 12A:
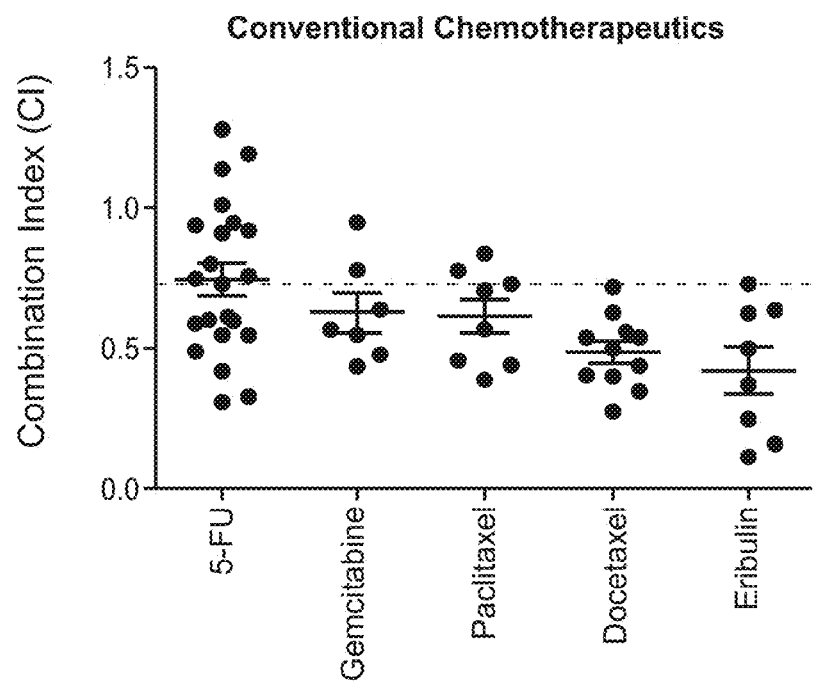
FIG. 12a shows the Combination Indices (CI) of combinations of GDC-0032+conventional chemotherapeutic agents including 5-FU, gemcitabine, paclitaxel, docetaxel and eribulin against cancer cell lines. A CI value below about 0.7 indicates synergy. Each dot represents a different cell line used in the chemotherapeutic agent+GDC-0032 combination.

FIG. 12a shows the Combination Indices (CI) of combinations of GDC-0032+conventional chemotherapeutic agents including 5-FU, gemcitabine, paclitaxel, docetaxel and eribulin against cancer cell lines. A CI value below about 0.7 indicates synergy. Each dot represents a different cell line. CI values indicating synergy was observed in the majority of cell lines and chemotherapeutic agent combinations evaluated.

Figure 12B:
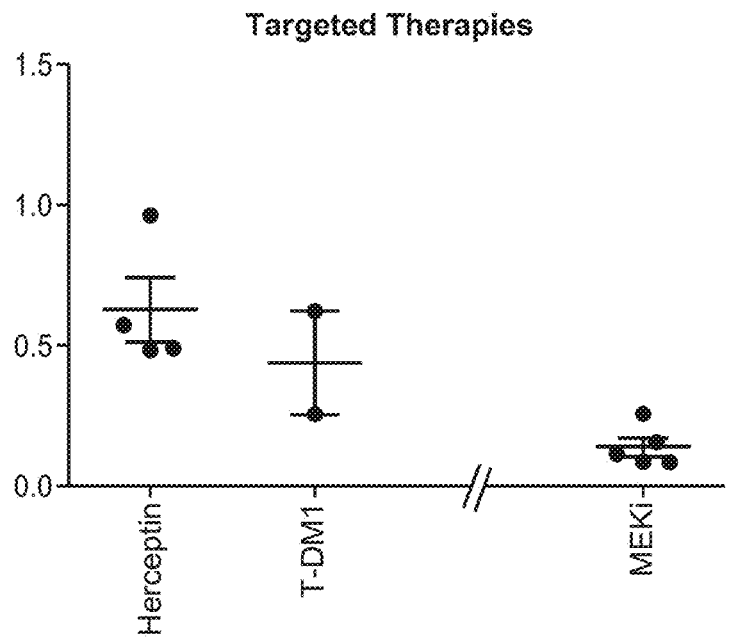
FIG. 12b shows the Combination Indices (CI) of combinations of GDC-0032+targeted chemotherapeutic agents including trastuzumab (Herceptin®), trastuzumab emtansine (T-DM1), and MEKi (GDC-0973) against cancer cell lines. A CI value below about 0.7 indicates synergy. Each dot represents a different cell line.

FIG. 12b shows the Combination Indices (CI) of combinations of GDC-0032+targeted chemotherapeutic agents including trastuzumab (Herceptin®), trastuzumab emtansine (T-DM1), and MEKi (GDC-0973) against cancer cell lines. A CI value below about 0.7 indicates synergy. Each dot represents a different cell line. Synergy was observed with targeted agent combinations in the majority of cell lines evaluated.

Endocrine therapies such as letrozole or fulvestrant are commonly used treatment options for metastatic Hormone Receptor positive (HR+) breast cancer but patients ultimately relapse. Phosphatidylinositol 3-kinases (PI3K) regulate breast tumor cell growth, migration and survival. The alpha isoform of PI3K is frequently mutated and activated in HR+ breast cancer and has been implicated in resistance to endocrine therapies. PI3K inhibitors are therefore attractive for combination with endocrine therapies. GDC-0032 is an orally bioavailable, potent, and selective inhibitor of Class I PI3K alpha, delta, and gamma isoforms, with 30-fold less inhibition of the PI3K beta isoform relative to the PI3K alpha isoform. Preclinical data show that GDC-0032 has increased activity against PI3K alpha isoform (PIK3CA) mutant and HER2-amplified cancer cell lines. Single agent and combination studies were carried out to determine if GDC-0032 enhances the anti-tumor activity of endocrine therapies in human breast cancer models. FIGS. 37A and 37B show the activity of letrozole and PI3K inhibitor GDC-0032 in aromatase expressing MCF7 cells. Sensitivity to endocrine therapies increases in MCF7-ARO cells grown with estrogen precursor androstenedione in media. Aromatase-expressing MCF7 cells convert androstenedione to estrogen in culture. MCF7 cells (Estrogen Receptor positive (ER+), PI3K alpha E545K mutant) were transfected with the aromatase gene and stable clones (MCF7-ARO) were selected that are capable of converting androstenedione to estrogen in culture. When grown in the presence of androstenedione, MCF7-ARO cells were more reliant on estrogen for growth. Sensitivity to endocrine therapies increases in MCF7-ARO cells grown with estrogen precursor in media. Under these conditions the cells were treated with GDC-0032 in combination with endocrine therapies and assayed for cellular viability, modulation of PI3K pathway and ER pathway markers and apoptosis induction. The combination of GDC-0032 and endocrine therapies decreased the cellular viability of MCF7-ARO cells and increased apoptosis relative to either single agent. The GDC-0032 and letrozole combination increases apoptosis in responsive cells because letrozole decreases PI3K pathway signaling at mTOR and letrozole upregulates pAKT and HER2, as does fulvestrant.

FIGS. 38A-D show GDC-0032 combines well with letrozole in vitro by quantitative scoring of inhibition of cell viability (FIG. 38A), BLISS (FIG. 38B), and HSA (FIG. 38C). FIGS. 39A and 39B show cross-talk between the PI3K and ER pathways was observed that suggests a mechanism of action for the combination of GDC-0032 and letrozole. Twenty-four hour treatment of cells with letrozole increases HER2 and pAkt, but decreases pmTOR and pp 70S6K. FIGS. 40A-C show endocrine-resistant cells have elevated PI3K pathway signaling and are sensitive to GDC-0032. Endocrine-resistant MCF7-ARO cells were obtained by letrozole dose escalation over about 4 months. The cells were resistant to exemestane, fulvestrant, tamoxifen and letrozole (FIG. 40A). The data (FIGS. 40B and 40C) provide rationale for evaluating GDC-0032 in combination with endocrine therapies for HR+ breast cancer treatment in the clinic.

GDC-0032 Single Agent In Vivo Tumor Xenograft Activity

The efficacy of GDC-0032 was measured in vivo by implanting xenografts of tumor cells representing breast, non-small cell lung cancer, ovarian, prostate, melanoma and colorectal cancers in immunocompromised mice and treating tumor-bearing animals with GDC-0032. Results are dependent on the cell line, the presence or absence of certain mutations in the tumor cells, the dosing regimen of GDC-0032, and other factors. Subject mice were treated with drug(s) or control (Vehicle) and monitored over several weeks or more to measure the time to tumor doubling, log cell kill, and tumor inhibition (Example 4). FIGS. 13-22 show plots of tumor volume change over time after treatment of tumor-bearing mice with GDC-0032 according to the protocol of Example 4.

Figure 13:
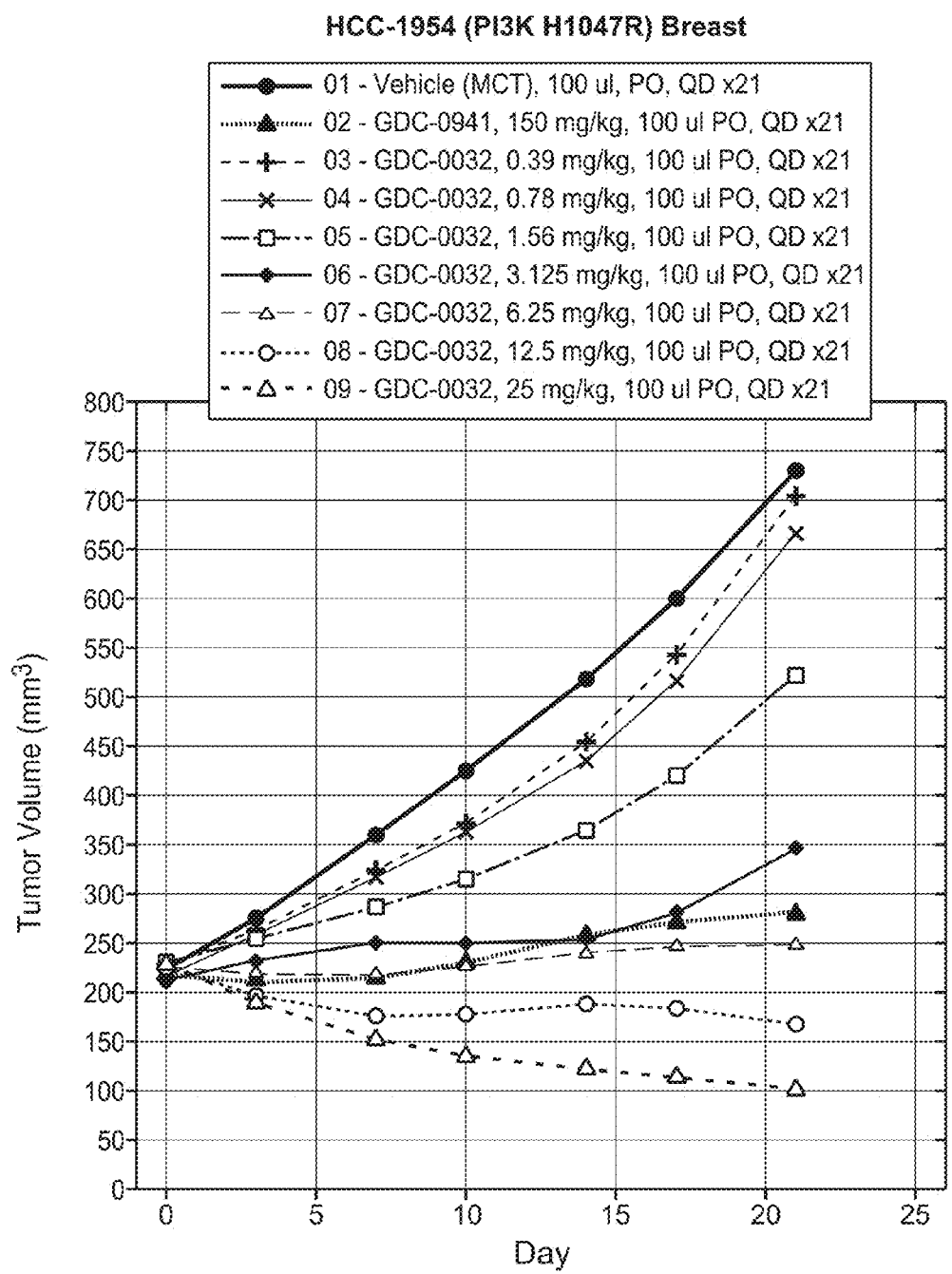
FIG. 13 shows the fitted tumor volume change over 21 days in cohorts of 8-10 immunocompromised mice bearing HCC1954.x1 breast tumor xenografts harboring PIK3CA H1047R (PI3Kα) mutation dosed once daily by 100 microliter (ul) PO (oral) administration with Vehicle (MCT; 0.5% methylcellulose/0.2% Tween 80), GDC-0941, and GDC-0032. The term uL means microliter.

FIG. 13 shows the fitted tumor volume change over 21 days in cohorts of immunocompromised (nude) mice bearing HCC1954.x1 breast tumor xenografts harboring PI3Kα mutation (H1047R) mutation dosed according to the schedule in Table 4 by 100 microliter (ul) PO (oral) and daily (QD) administration with Vehicle (MCT; 0.5% methylcellulose/0.2% Tween 80), GDC-0941, and GDC-0032. A dose-depended increase in tumor growth inhibition (TGI) was observed with daily dosing of GDC-0032 and a maximum TGI of 138% was achieved at the end of dosing on day 21. Tumor regressions were observed at doses of 12.5 and 25 mg/kg of GDC-0032. The term uL means microliter.

TABLE 4

Single agent activity of GDC-0032 Dosed Daily (QD) in HCC1954.x1 Breast Cancer Xenografts with H1047R mutation.

| Test Agent | Schedule | Dose (mg/kg) | % TGI@ day 21 (lower |
|---|---|---|---|
| Vehicle (MCT) | QD x 21 | 0.0 | 0 (0, 0) |
| GDC-0941 | QD x 21 | 150 | 90 (68, 106) |
| GDC-0032 | QD x 21 | 0.39 | 19 (−45, 56) |
| GDC-0032, | QD x 21 | 0.78 | 22 (−37, 57) |
| GDC-0032 | QD x 21 | 1.56 | 53 (7, 78) |
| GDC-0032, | QD x 21 | 3.125 | 79 (53, 98) |
| GDC-0032, | QD x 21 | 6.25 | 98 (80, 115) |
| GDC-0032 | QD x 21 | 12.5 | 118 (105, 139) |
| GDC-0032, | QD x 21 | 25 | 138 (123, 163) |

*values in parenthesis represents 95% confidence intervals; TGI (tumor growth inhibition); MCT (0.5% methylcellulose/0.2% Tween-80)

Figure 14:
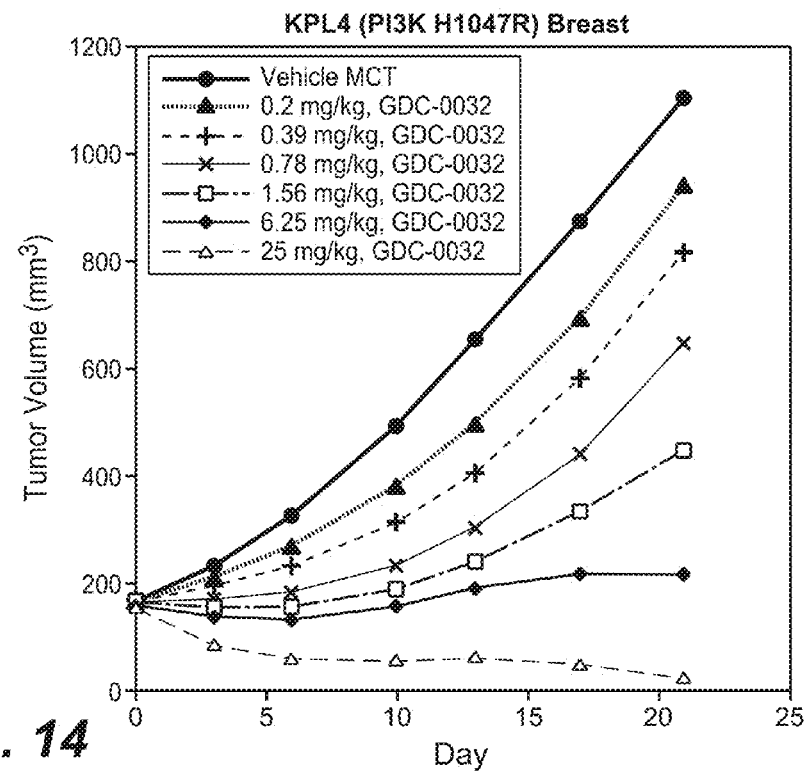
FIG. 14 shows the fitted tumor volume change over 21 days in cohorts of 8-10 immunocompromised mice bearing KPL4 breast tumor xenografts with HER2+ and PIK3CA H1047R mutation dosed by PO (oral) administration with Vehicle and GDC-0032.

FIG. 14 shows the fitted tumor volume change over 21 days in cohorts of immunocompromised (SCID beige) mice bearing KPL4 breast tumor xenografts harboring PI3Kα (H1047R) mutation dosed by PO (oral) and daily (QD) administration with Vehicle (MCT; 0.5% methylcellulose/0.2% Tween 80) and GDC-0032. A dose dependent decrease in tumor volume was achieved with daily dosing of GDC-0032 in the KPL4 xenograft model with increased tumor regressions observed with 25 mg/kg of GDC-0032 compared to vehicle control treated mice at the end of treatment on day 21.

Figure 15:
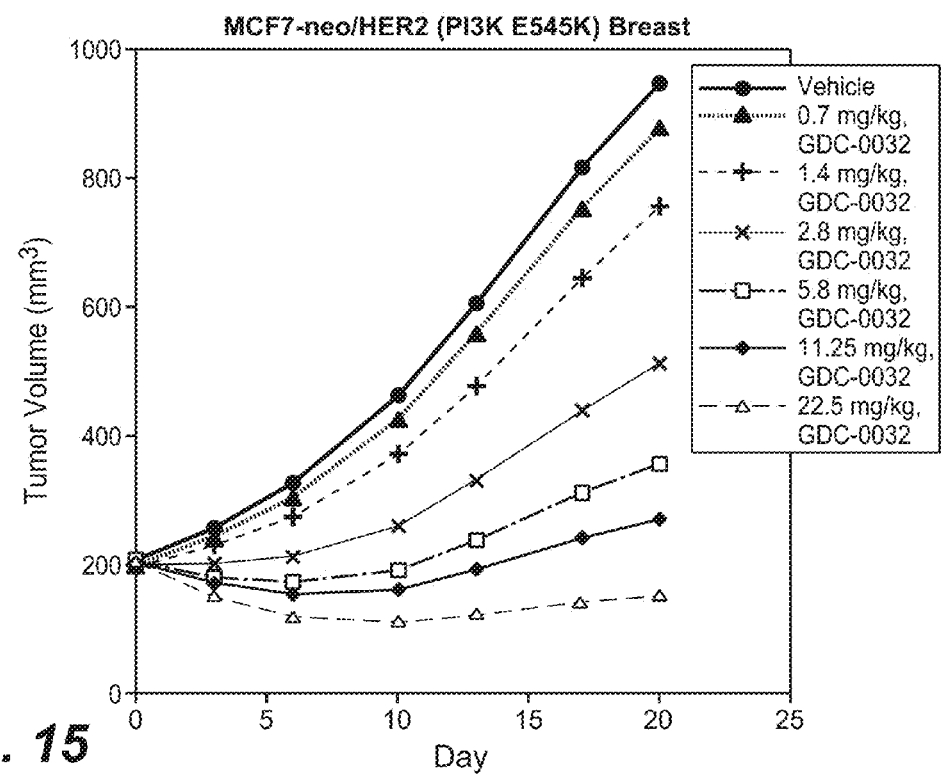
FIG. 15 shows the fitted tumor volume change over 21 days in 8-10 immunocompromised mice with MCF7-neo/HER2 (HER2+, PIK3CA E545K) breast cancer tumor xenografts dosed once daily by PO (oral) administration with Vehicle and GDC-0032.

FIG. 15 shows the fitted tumor volume change over 20 days in cohorts of immunocompromised (nude) mice bearing MCF7-neo/HER2 breast tumor xenografts harboring PI3Kα mutations (E545K) dosed by PO (oral) and daily (QD) administration with Vehicle (MCT; 0.5% methylcellulose/0.2% Tween 80) and GDC-0032. A dose dependent decrease in tumor volume was achieved with daily dosing of GDC-0032 in the MCF7-neo/HER2 xenograft model with increased tumor regressions observed with 22.5 mg/kg of GDC-0032 compared to vehicle control treated mice after 10 days of treatment.

Figure 16:
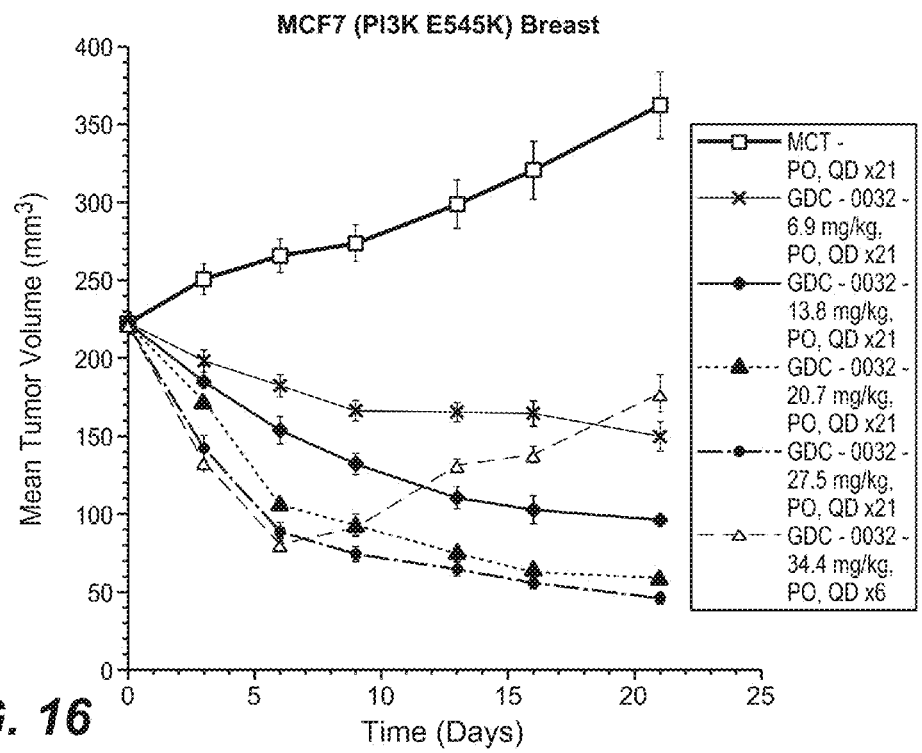
FIG. 16 shows the fitted tumor volume change over 21 days in cohorts of 8-10 immunocompromised mice bearing MCF-7 with PIK3CA E545K mutation breast cancer tumor xenografts dosed once daily by PO (oral) administration with MCT vehicle and GDC-0032.

FIG. 16 shows the fitted tumor volume change over 21 days in cohorts of immunocompromised (nude) mice bearing MCF-7 breast tumor xenografts harboring PI3Ka mutations (E545K) dosed by PO (oral) and daily (QD) administration with vehicle (MCT; 0.5% methycellulose/0.2% Tween 80) and GDC-0032. A dose-dependent decrease in tumor volume was achieved with daily dosing of GDC-0032 in the MCF-7 xenograft model. Increased tumor regressions was observed with all doses of GDC-0032 tested compared to vehicle controls.

Figure 17:
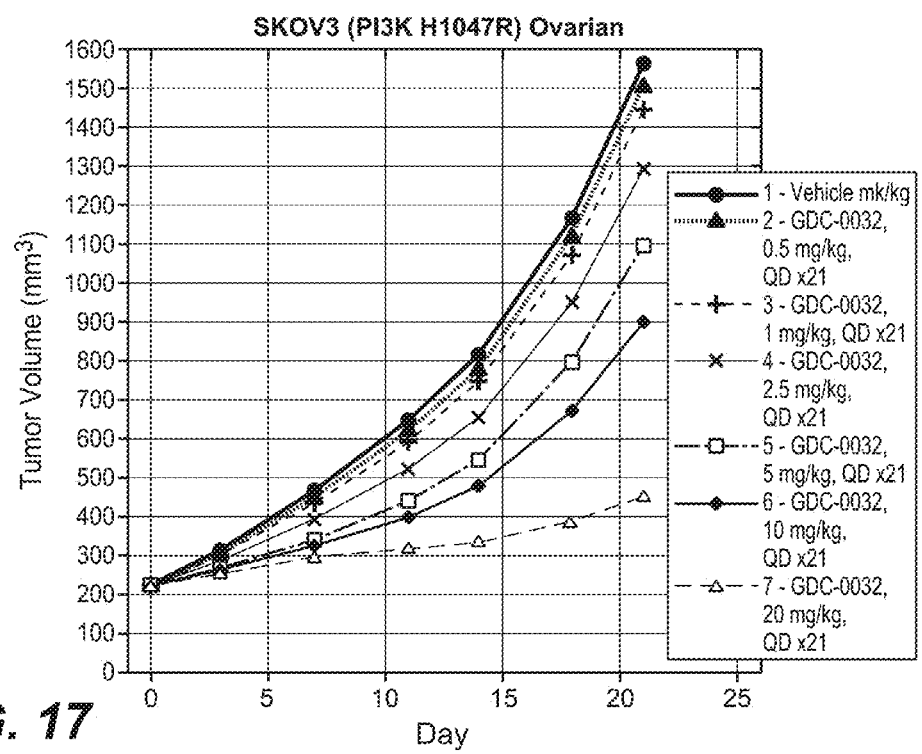
FIG. 17 shows the fitted tumor volume change over 21 days in cohorts of 8-10 immunocompromised mice bearing SKOV3 ovarian tumor xenografts harboring PIK3CA H1047R mutation dosed once daily by PO (oral) administration with Vehicle and GDC-0032.

FIG. 17 shows the fitted tumor volume change over 21 days in cohorts of immunocompromised (nude) mice bearing SKOV3 ovarian tumor xenografts harboring PI3Kα mutation (H1047R) dosed by PO (oral) and daily (QD) administration with Vehicle (MCT; 0.5% methycellulose/0.2% Tween 80) and GDC-0032. A dose-dependent decrease in tumor volume was achieved with daily dosing of GDC-0032 during a 21 day treatment period in the SKOV3 xenograft model.

Figure 18:
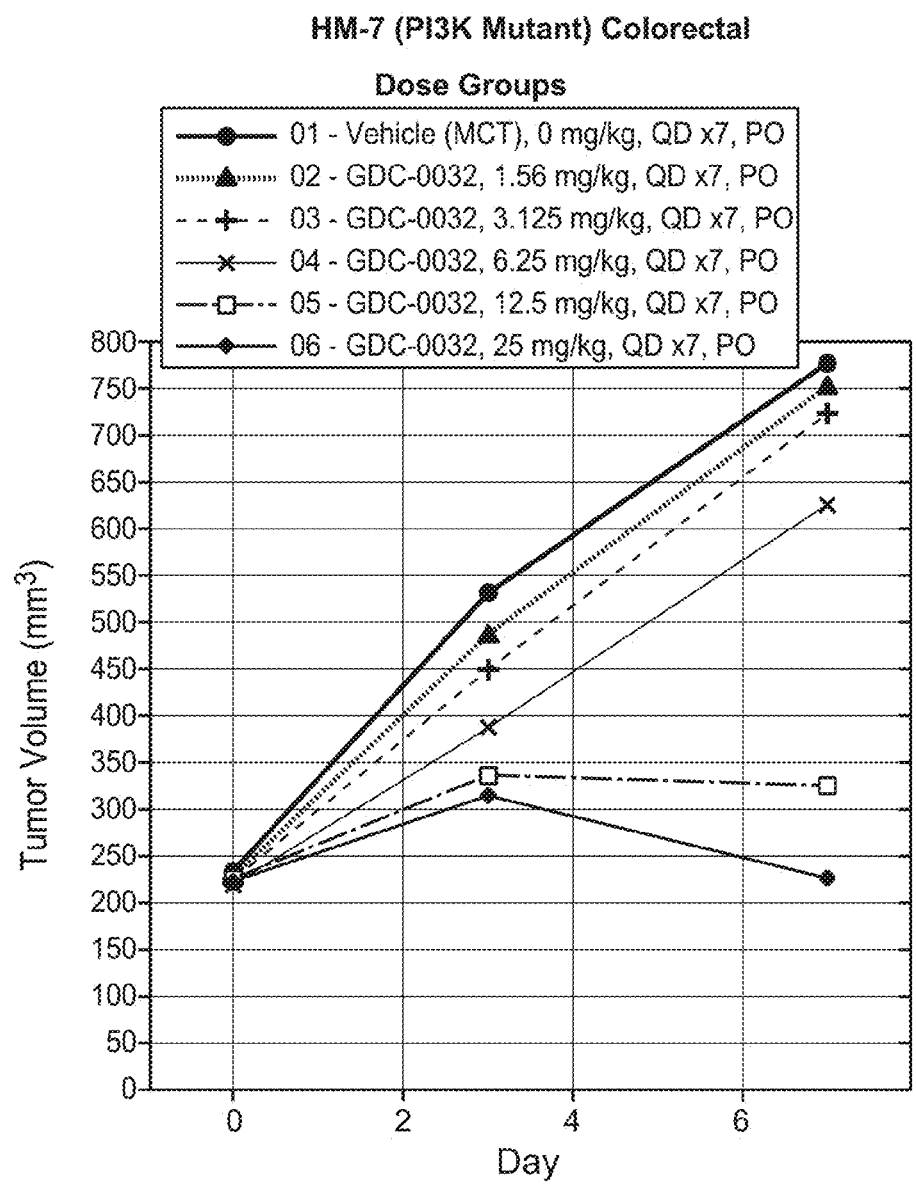
FIG. 18 shows the fitted tumor volume change over 6+days in cohorts of 8-10 immunocompromised mice with HM-7 colorectal tumor xenografts with PI3K alpha (α) mutation (H1047R) dosed once daily by PO (oral) administration with Vehicle and GDC-0032.

FIG. 18 shows the fitted tumor volume change over 7 days in cohorts of immunocompromised (nude) mice bearing HM-7 colorectal cancer tumor xenografts harboring PI3Kα mutation (H1047R) dosed by PO (oral) and daily (QD) administration with Vehicle (MCT; 0.5% methycellulose/0.2% Tween 80) and GDC-0032. A dose dependent decrease in tumor volume was achieved with daily dosing of GDC-0032 in the HM-7 xenograft model with increased tumor regressions observed with 25 mg/kg of GDC-0032 compared to vehicle control treated mice at the end of treatment on day 7.

Figure 19:
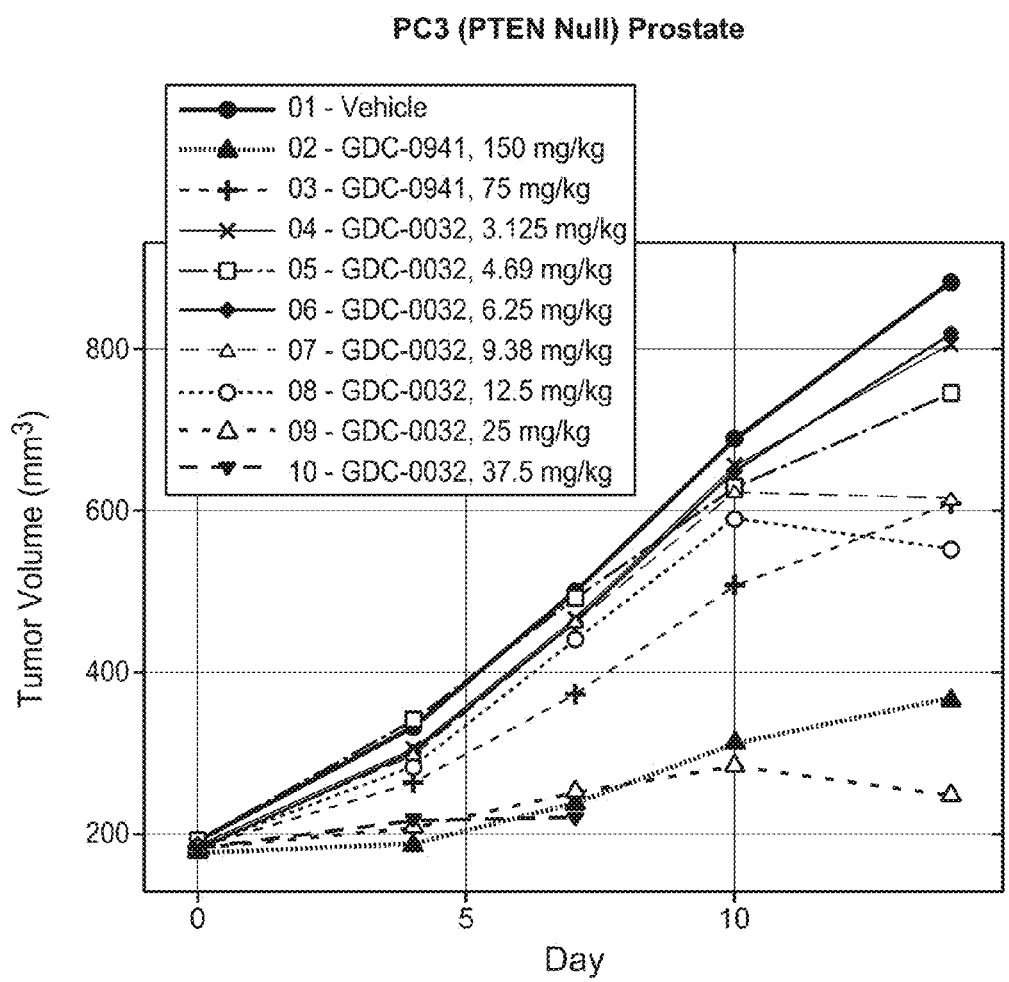
FIG. 19 shows the fitted tumor volume change over 14 days in cohorts of 8 to 10 immunocompromised mice with PC3 prostate tumor xenografts that are PTEN null dosed once daily by PO (oral) administration with Vehicle and GDC-0032.

FIG. 19 shows the fitted tumor volume change over 14 days in cohorts of immunocompromised (nude) mice bearing PC3 prostate cancer tumor xenografts that are PTEN negative (null) dosed by PO (oral) and daily (QD) administration with Vehicle (MCT; 0.5% methycellulose/0.2% Tween 80) and GDC-0032. Doses of GDC-0032<12.5 mg/kg were not efficacious after daily dosing of GDC-0032 for 14 days. However, an anti-tumor response was observed in the PC3 xenograft model at the highest dose tested (25 mg/kg) and was characterized as tumor stasis.

Figure 20:
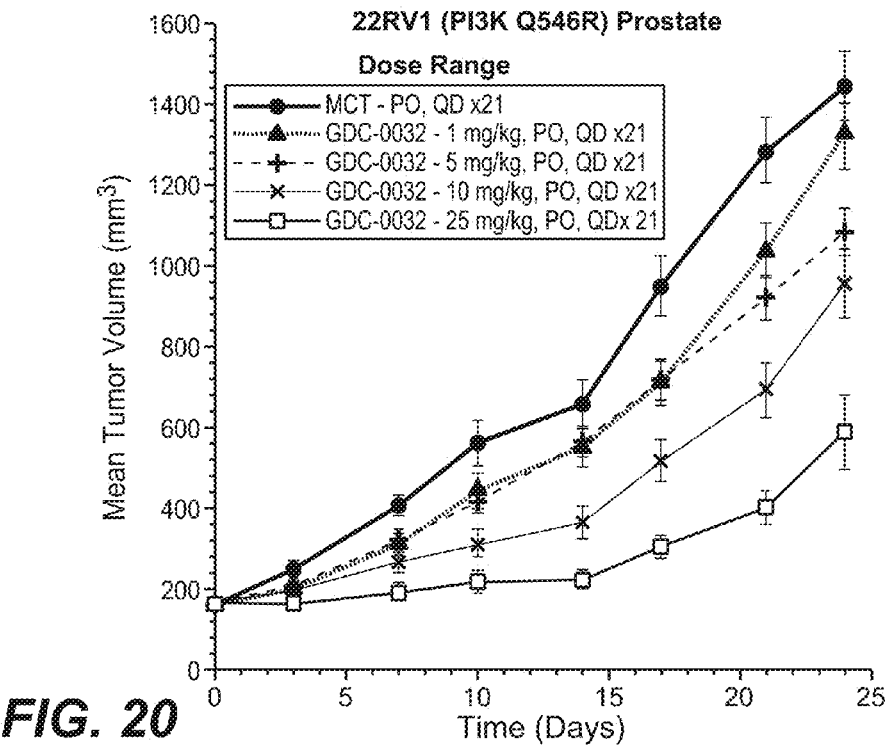
FIG. 20 shows the fitted tumor volume change over 24 days in cohorts of 8 to 10 immunocompromised mice bearing 22RV1 prostate tumor xenografts harboring PI3Kα mutation (Q546R) dosed by PO (oral) administration with Vehicle and GDC-0032.

FIG. 20 shows the fitted tumor volume change over 24 days in cohorts of immunocompromised (nude) mice bearing 22RV1 prostate cancer tumor xenografts that were PTEN negative (null) dosed by PO (oral) or daily (QD) administration with Vehicle (MCT; 0.5% methycellulose/0.2% Tween 80) and GDC-0032. A dose-dependent decrease in tumor volume was achieved with daily dosing of GDC-0032 in the 22RV1 xenograft model.

Figure 21:
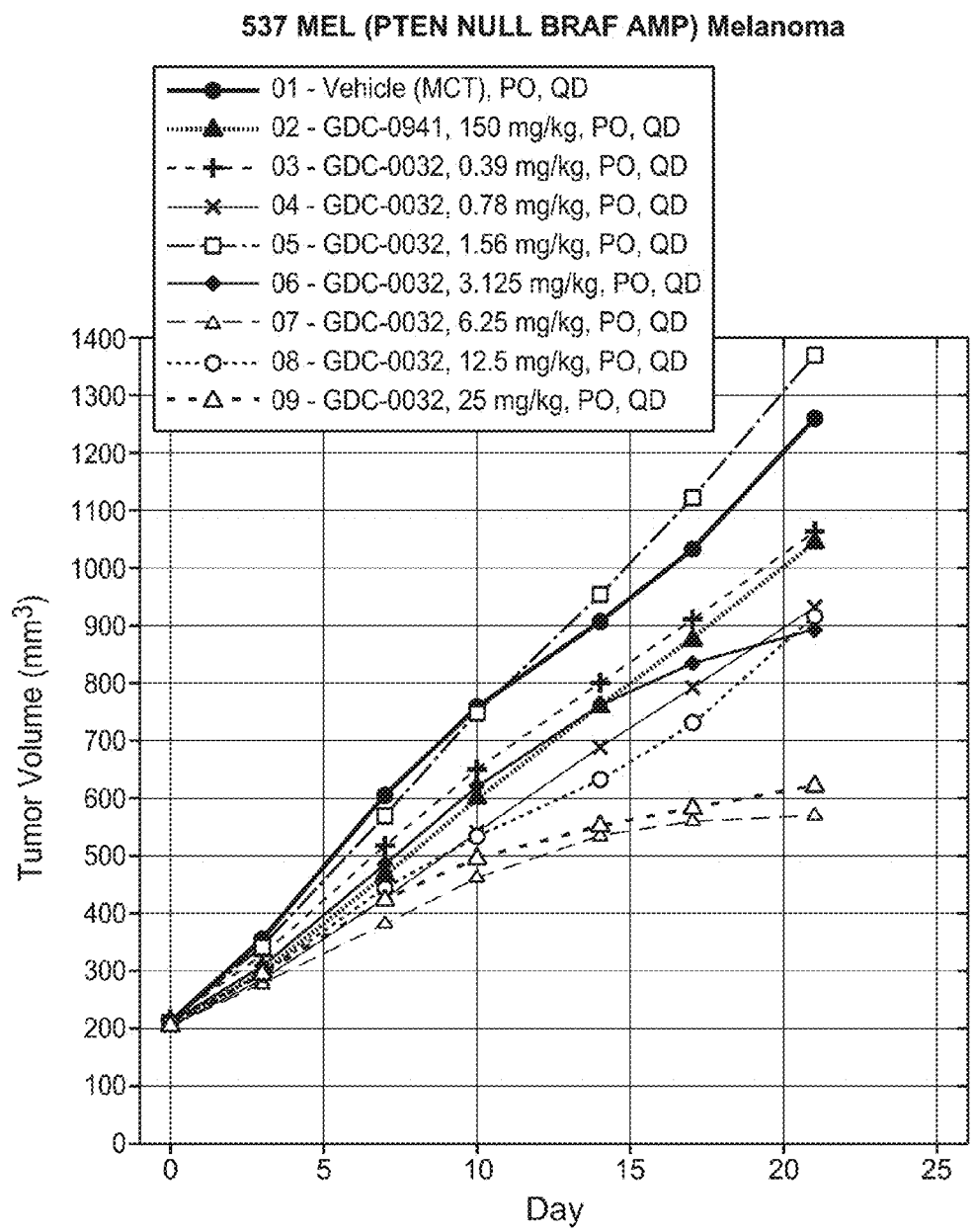
FIG. 21 shows the fitted tumor volume change over 21 days in cohorts of 8 to 10 immunocompromised mice bearing 537 MEL melanoma tumor xenografts that are deficient in PTEN and harbor B-Raf amplifications dosed by PO (oral) administration with Vehicle, GDC-0941 and GDC-0032.

FIG. 21 shows the fitted tumor volume change over 21 days in cohorts of immunocompromised (nude) mice bearing 537 MEL melanoma cancer tumor xenografts that are PTEN null and have B-Raf amplifications dosed by PO (oral) and daily (QD) administration with Vehicle (MCT; 0.5% methycellulose/0.2% Tween 80), GDC-0941 and GDC-0032. A dose-dependent decrease in tumor volume was achieved with daily dosing of GDC-0032 in the 22RV1 xenograft model.

Figure 22:
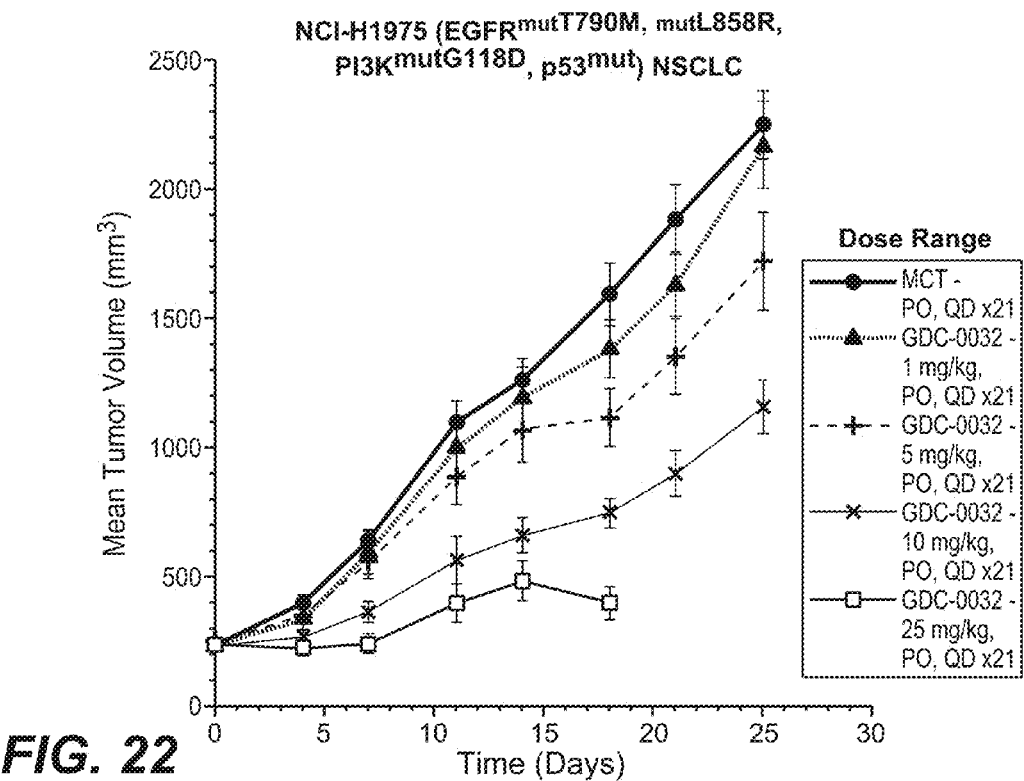
FIG. 22 shows the fitted tumor volume change over 0 to 24+ days in cohorts of 8 to 10 immunocompromised mice bearing NCI-H1975 non-small cell lung cancer (NSCLC) tumor xenografts harboring EGFR-double mutant L858R and T790M, PIK3CA G118D, p53 mutation, dosed by PO (oral) administration with Vehicle (MCT) and GDC-0032.

FIG. 22 shows the mean tumor volume change over 24 days in cohorts of immunocompromised (nude) mice bearing NCI-H1975 non-small cell lung cancer (NSCLC) tumor xenografts harboring EGFR mutations (T790M), PI3K mutations (G118D) and p53 mutations dosed by PO (oral) and daily (QD) administration with Vehicle (MCT; 0.5% methycellulose/0.2% Tween 80) and GDC-0032. A dose-dependent decrease in tumor volume was observed over a 24 day treatment period with GDC-0032 compared to vehicle control treated mice.

GDC-0032 and Chemotherapeutic Combinations In Vivo Tumor Xenograft Activity

The efficacy of the combinations of GDC-0032 and various chemotherapeutic agents, including small-molecule and large-molecule targeted agents, was measured in vivo by implanting allografts or xenografts of cancer cells in rodents and treating the tumor-bearing animals with the drug combinations. Results are dependent on the cell line, the presence or absence of certain mutations in the tumor cells, the sequence of administration of GDC-0032 and chemotherapeutic agent, dosing regimen, and other factors. Subject mice were treated with drug(s) or control (Vehicle) and monitored over several weeks or more to measure the time to tumor doubling, log cell kill, and tumor inhibition (Example 4). FIGS. 23-36 show plots of tumor volume change over time after treatment of tumor-bearing mice treated with combinations of GDC-0032 and various chemotherapeutic agents according to the protocol of Example 4.

Figure 23:
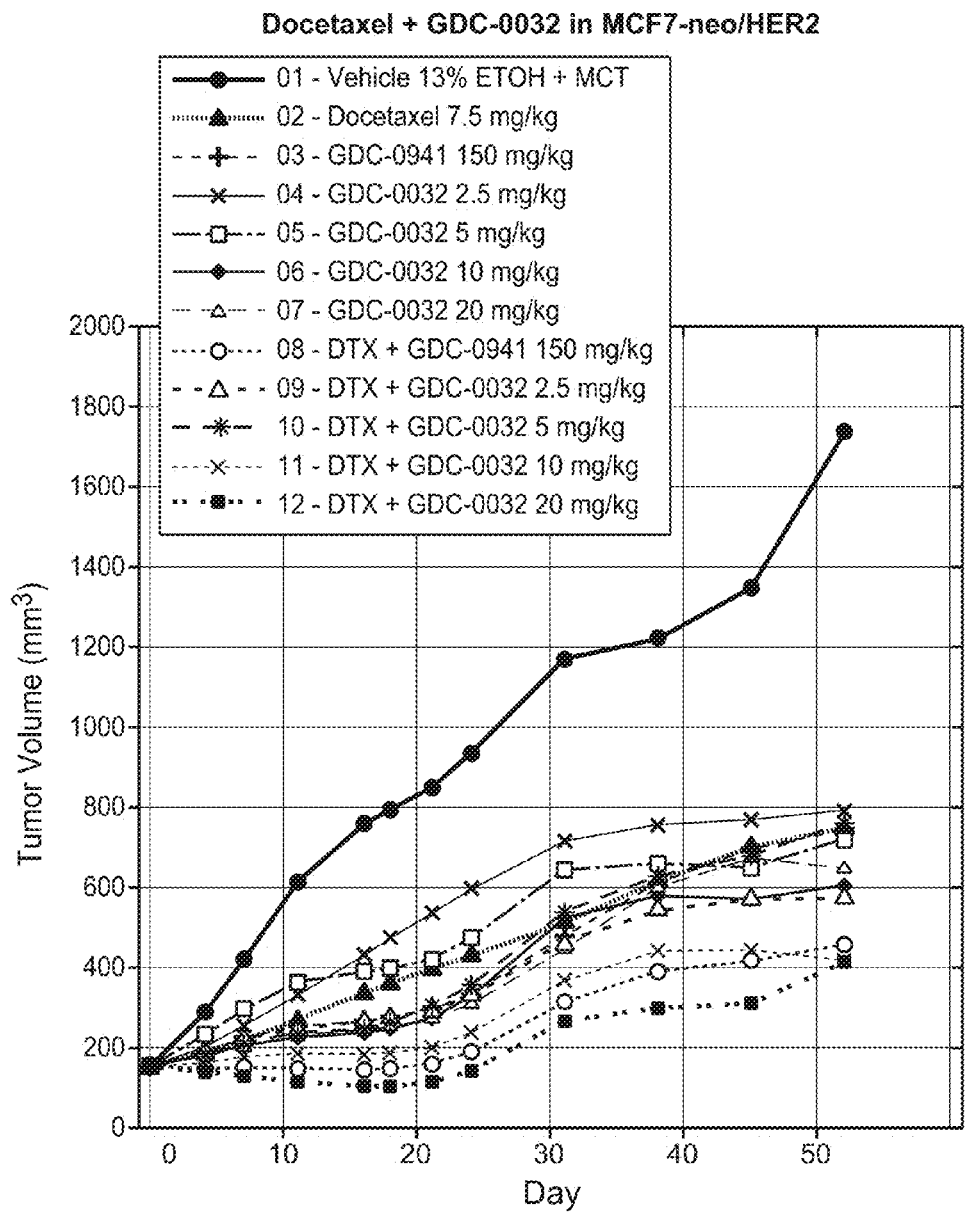
FIG. 23 shows the fitted tumor volume change over 51 days in cohorts of 8 to 10 immunocompromised mice bearing MCF-7 neo/HER2 breast tumor xenografts harboring PI3K alpha (E545K) dosed according to the schedule in Table 5. GDC-0032 and GDC-0941 were dosed once daily by PO (oral) administration and docetaxel by IP administration, with final dosing on day 21. Cohorts are Vehicle, docetaxel (DTX), GDC-0941, GDC-0032, and the combinations of docetaxel+GDC-0941 and docetaxel+GDC-0032.

FIG. 23 shows the mean tumor volume change over 51 days in cohorts of immunocompromised mice (nude) mice bearing MCF-7 neo/HER2 breast cancer tumor xenografts dosed according to the schedule in Table 5 by administration with Vehicle, docetaxel (DTX), GDC-0941, GDC-0032, and the combinations of docetaxel+GDC-0941 or docetaxel+GDC-0032. GDC-0941 and GDC-0032 was dosed orally (PO) and daily (QD) for 21 days. Docetaxel was dosed intravenously and weekly (QW) for 3 weeks. After dosing ended on day 21, mice were monitored for tumor regrowth for an additional 30 days. When compared to each single agent alone, the combination of GDC-0032 enhanced the anti-tumor activity of DTX by increasing tumor regressions. At the highest doses tested of GDC-0032 (20 mg/kg) in combination with DTX was comparable in terms of % TGI to GDC-00941 in combination with DTX (Table 5).

TABLE 5

Combinations of GDC-0941/GDC-0032 with docetaxel (DTX) in MCF-7 neo/HER2 Breast Cancer Xenografts with daily (QD) or weekly (QW) schedule dosing, oral (PO) route of administration, and measured tumor growth inhibition (TGI) at 21 days.

| Test Agent | Schedule | Dose (mg/kg) | % TGI @ day 21 |
|---|---|---|---|
| 01 Vehicle (0.5% methylcellulose/ 0.2% Tween 80) | QD | 0.0 | 0 |
| 02 Docetaxel | QW | 7.5 | 69 |
| 03 GDC-0941 | QD | 150 | 80 |
| 04 GDC-0032 | QD | 2.5 | 53 |
| 05 GDC-0032 | QD | 5.0 | 57 |
| 06 GDC-0032 | QD | 10 | 83 |
| 07 GDC-0032 | QD | 20 | 83 |
| 08 DTX + GDC-0941 | QW + QD | 5 + 150 | 99 |
| 09 DTX + GDC-0032 | QW + QD | 5 + 2.5 | 80 |
| 10 DTX + GDC-0032 | QW + QD | 5 + 5 | 82 |
| 11 DTX + GDC-0032 | QW + QD | 5 + 10 | 92 |
| 12 DTX + GDC-0032 | QW + QD | 5 + 20 | 108 |

Figure 24:
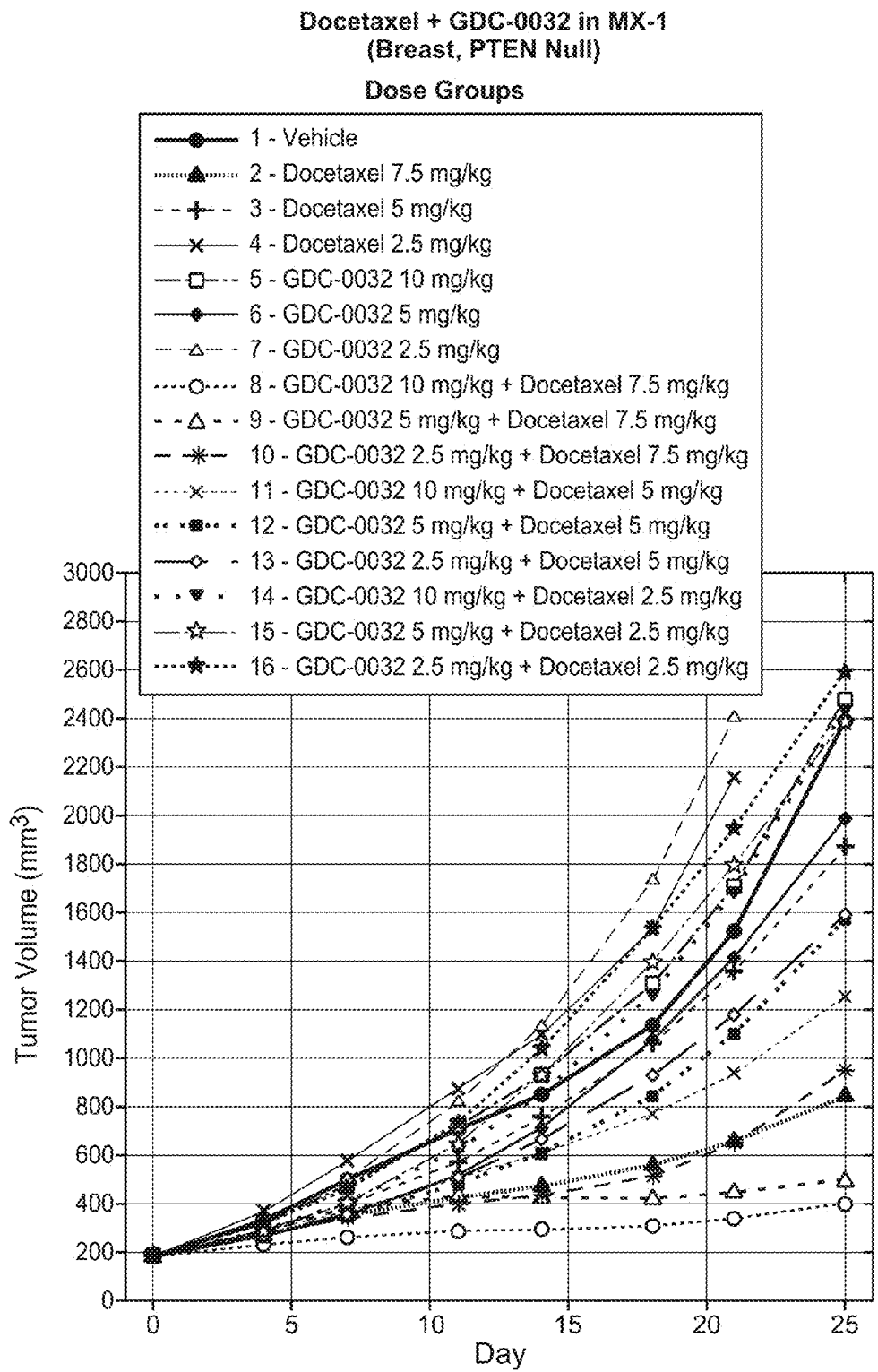
FIG. 24 shows the fitted tumor volume change over 25 days in cohorts of 8 to 10 immunocompromised mice with MX-1 triple Negative (ER$^-$ (estrogen receptor), PR$^-$ (progesterone receptor), HER2$^-$ (HER2 negative) breast cancer tumor xenografts with PTEN null dosed with Vehicle, docetaxel, GDC-0032, and combinations of GDC-0032+docetaxel.

FIG. 24 shows the mean tumor volume change over 25 days in cohorts of immunocompromised mice bearing MX-1 Triple Negative (ER⁻ (estrogen receptor), PR (progesterone receptor, neu/HER2⁻ (HER2 receptor) breast cancer tumor xenografts that are PTEN negative (null) and dosed by administration with vehicle (0.5% methylcelluose/0.2% Tween-80), docetaxel (DTX), GDC-0032, and combinations of GDC-0032+docetaxel. GDC-0032 was dosed orally (PO) and daily (QD) for 21 days. DTX was dosed intravenously and weekly (QW) for 3 weeks with 2.5, 5.0 and 7.5 mg/kg of drug. After dosing ended on day 21, mice were monitored for tumor regrowth for an additional 4 days. GDC-0032 enhanced the anti-tumor activity of DTX at all doses tested. Maximum combination activity was observed with 5 and 10 mg/kg of GDC-0032 plus 7.5 mg/kg of DTX when compared to each drug alone.

Figure 25:
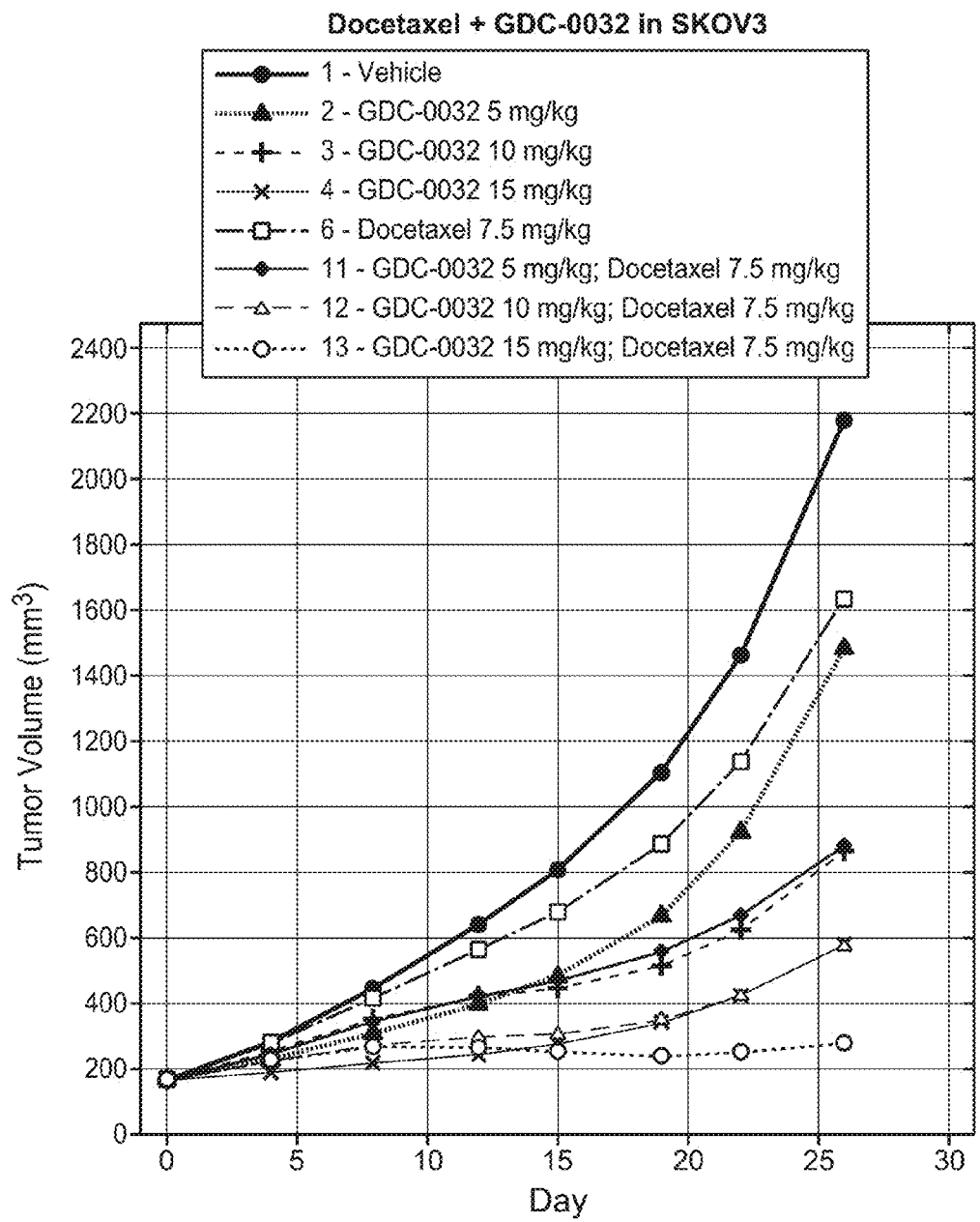
FIG. 25 shows the fitted tumor volume change over 26 days in cohorts of 8 to 10 immunocompromised mice bearing SKOV3 ovarian tumor xenografts with PIK3CA (PI3Kα) H1047R dosed for 21 days with Vehicle, docetaxel, GDC-0032, and combinations of GDC-0032+docetaxel.

FIG. 25 shows the mean tumor volume change over 25 days in cohorts of immunocompromised mice bearing SKOV3 ovarian cancer tumor xenografts that harbor PI3K mutations (H1047R) mutation dosed by administration with vehicle (0.5% methylcelluose/0.2% Tween-80), docetaxel (DTX), GDC-0032, and combinations of GDC-0032+docetaxel. GDC-0032 was dosed orally (PO) and daily (QD) for 21 days. DTX was dosed intravenously and weekly (QW) for 3 weeks with 7.5 mg/kg of drug. After dosing ended on day 21, mice were monitored for tumor regrowth for an additional 4 days. GDC-0032 enhanced the anti-tumor activity of DTX at all doses of GDC-0032 tested. Maximum combination activity was observed with 15 mg/kg of GDC-0032 plus 7.5 mg/kg of DTX when compared to each drug alone.

Figure 26:
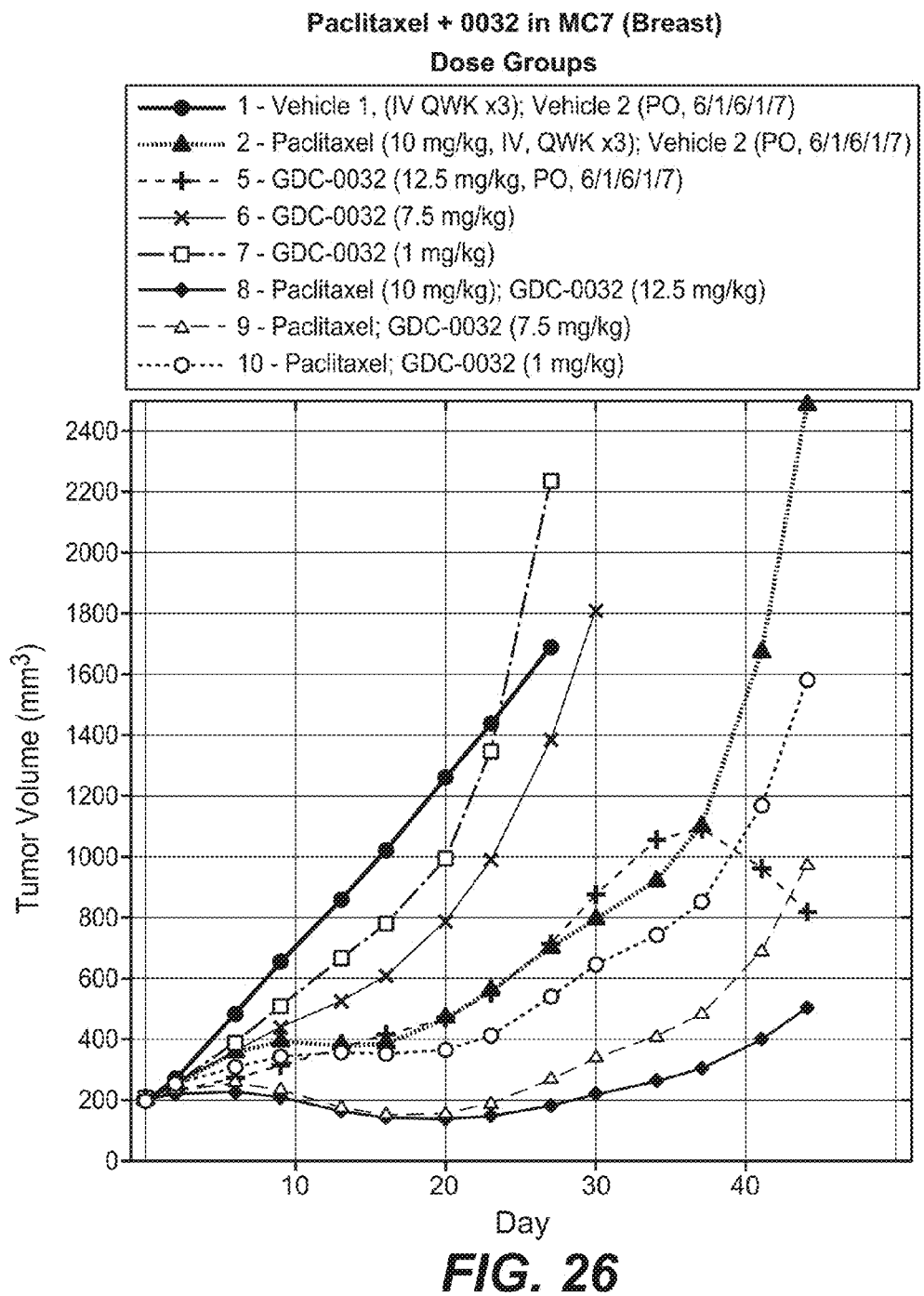
FIG. 26 shows the fitted tumor volume change over 40 days in cohorts of 8 to 10 immunocompromised mice bearing MCF-7 PIK3CA mutant breast tumor xenografts harboring PI3Kα mutation (E545K) dosed for 21 days with Vehicle, paclitaxel, GDC-0032, and the combinations of paclitaxel+GDC-0032.

FIG. 26 shows the mean tumor volume change over 40+ days in cohorts of immunocompromised (nude) mice bearing MCF-7 breast cancer tumor xenografts that harbor PI3K mutations (E545K) dosed by administration with vehicle (0.5% methylcelluose/0.2% Tween-80), paclitaxel, GDC-0032, and combinations of GDC-0032+paclitaxel. GDC-0032 was dosed orally (PO) and daily (QD) for 21 days. Paclitaxel was dosed intravenously and weekly (QW) for 3 weeks with 10 mg/kg of drug. 7.5 and 12.5 mg/kg of GDC-0032 enhanced the anti-tumor activity of paclitaxel when compared to each drug alone.

Figure 27:
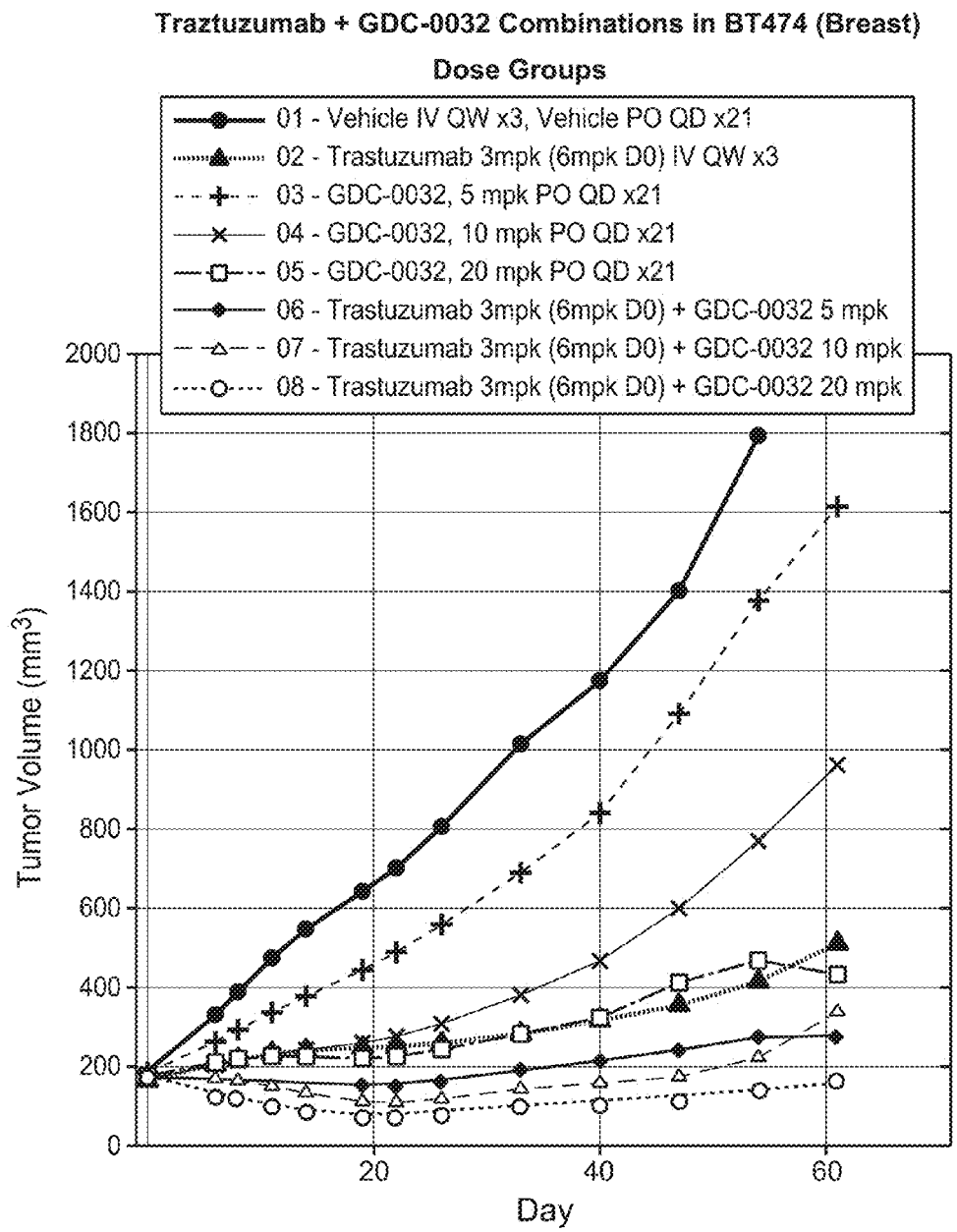
FIG. 27 shows the fitted tumor volume change over 61 days in cohorts of 8 to 10 immunocompromised mice bearing BT474, HER2+ breast cancer tumor xenografts dosed for 21 days with Vehicle, trastuzumab, GDC-0032, and the combinations of trastuzumab+GDC-0032.

FIG. 27 shows the mean tumor volume change over 60 days in cohorts of immunocompromised mice bearing BT474, HER2+ breast cancer tumor xenografts that harbor PI3K mutations (K111N) dosed by PO (oral) administration with vehicle (0.5% methylcelluose/0.2% Tween-80), trastuzumab (Herceptin®), GDC-0032, and the combinations of trastuzumab+GDC-0032. GDC-0032 was dosed orally (PO) and daily (QD) for 21 days with 5, 10 and 20 mg/kg. Trastuzumab was dosed intravenously (IV) and weekly (qW) at 3 mg/kg. A loading dose of 6 mg/kg of trastuzumab was given prior to the IV administration. GDC-0032 enhanced the efficacy of trastuzumab in a dose-dependent fashion.

Figure 28:
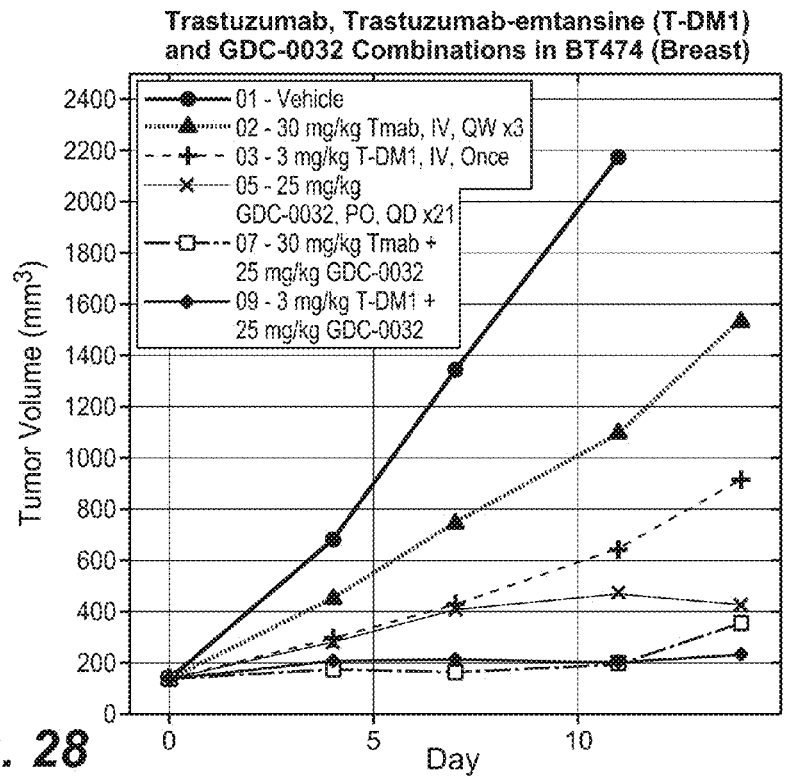
FIG. 28 shows the fitted tumor volume change over 14 days in cohorts of 8 to 10 immunocompromised mice bearing BT474, HER2+ breast cancer tumor xenografts dosed with Vehicle, trastuzumab, trastuzumab emtansine (T-DM1), GDC-0032, the combination of trastuzumab+GDC-0032, and the combination of trastuzumab emtansine and GDC-0032.

FIG. 28 shows the mean tumor volume change over 10+ days in cohorts of immunocompromised mice (nude) bearing Founder 5 (Fo5) HER2+ breast tumor allografts that are engineered to overexpress HER2 through the mouse mammary tumor virus (MMTV) dosed by oral (PO) administration with vehicle (0.5% methylcelluose/0.2% Tween-80), trastuzumab (Herceptin®), trastuzumab emtansine (T-DM1), GDC-0032, the combination of trastuzumab+GDC-0032, and the combination of T-DM1 and GDC-0032. GDC-0032 was dosed orally (PO) and daily (QD) for 15 days with 25 mg/kg of drug. Trastuzumab was dosed intravenously (IV) and weekly (qW) at 30 mg/kg and T-DM1 was dosed IV once. Compared to each agent alone, the combination of GDC-0032 enhanced the anti-tumor activity of trastuzumab and T-DM1 and induced tumor stasis. Differences in combination activity with GDC-0032 and trastuzumab vs. GDC-0032 and T-DM1 were not observed.

Figure 29:
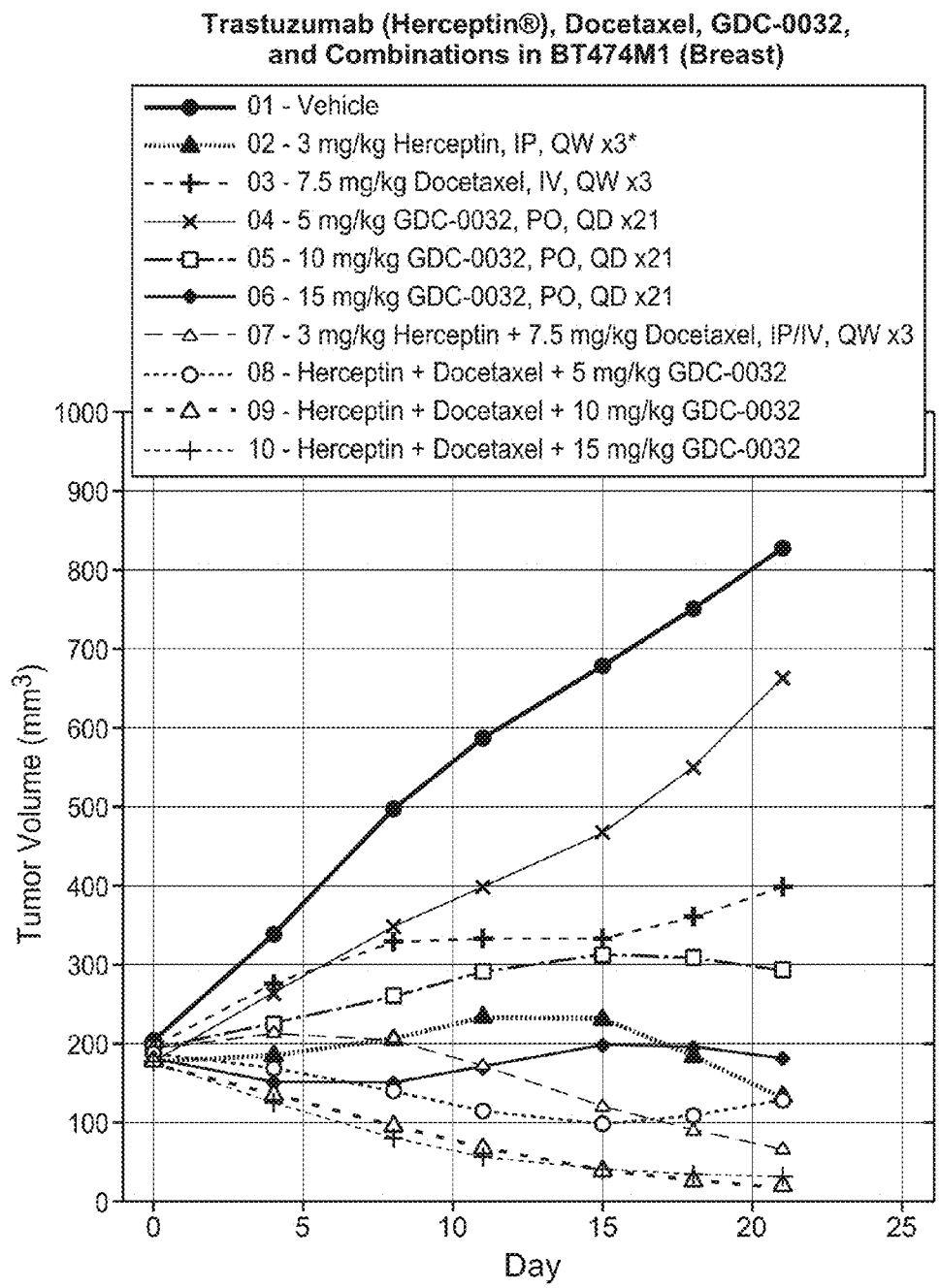
FIG. 29 shows the fitted tumor volume change over 21 days in cohorts of 8 to 10 immunocompromised mice with BT474, HER2+ breast cancer tumor xenografts dosed with Trastuzumab (Herceptin®), docetaxel, GDC-0032, the combination of trastuzumab and docetaxel, and the triple combination of trastuzumab, docetaxel, and GDC-0032.

FIG. 29 shows the mean tumor volume change over 21 days in cohorts of immunocompromised (nude) mice bearing BT474, HER2+ breast cancer tumor xenografts dosed by PO (oral) administration with vehicle (0.5% methylcellulose/0.2% Tween-80) trastuzumab (Herceptin®), docetaxel, GDC-0032, the combination of trastuzumab and docetaxel or the triple combination of trastuzumab, docetaxel, and GDC-0032. GDC-0032 was dosed orally (PO) and daily (QD) for 21 days with 5, 10 and 15 mg/kg. Trastuzumab was dosed intravenously (IV) and weekly (qW) at 3 mg/kg. Docetaxel was dosed intravenously and weekly (QW) for 3 weeks with 7.5 mg/kg of drug. Compared to trastuzumab and docetaxel monotherapy, the combination of both drugs resulted in increased tumor regressions. Addition of GDC-0032 at all doses tested to the double combination of docetaxel and trastuzumab further increased tumor regression during the treatment period.

Figure 30:
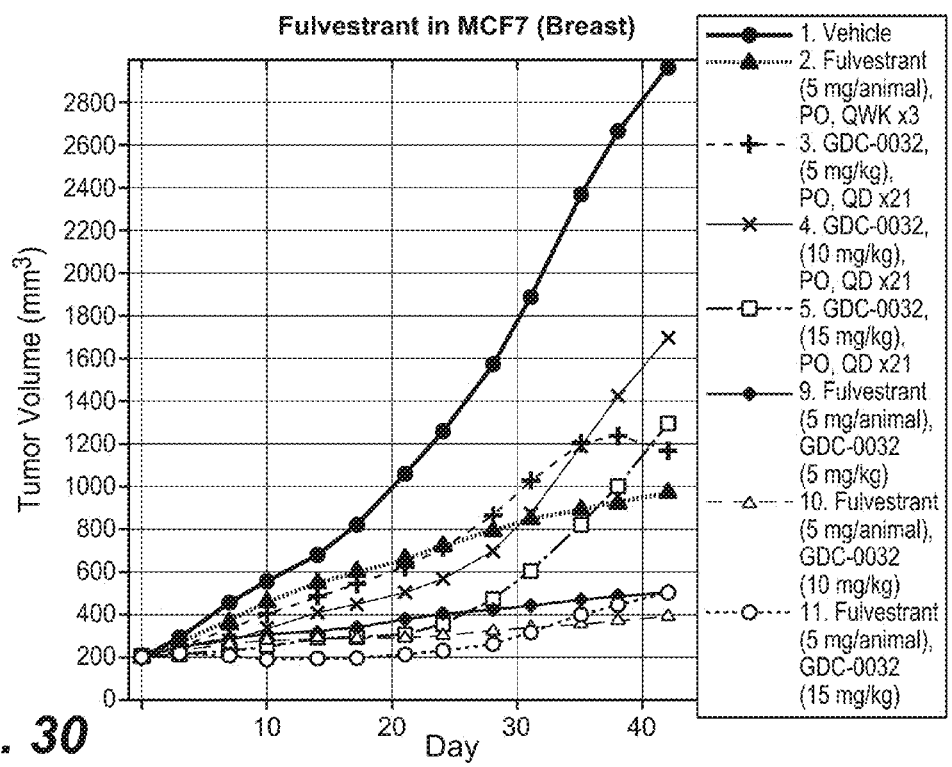
FIG. 30 shows the fitted tumor volume change over 42 days in cohorts of 8 to 10 immunocompromised mice bearing MCF-7 ER+, harboring PI3Kα mutation (E545K) PIK3CA dosed by PO (oral) administration with fulvestrant, GDC-0032, and the combination of fulvestrant and GDC-0032 for 21 days.

FIG. 30 shows the mean tumor volume change over 40+ days in cohorts of immunocompromised (nude) mice bearing MCF-7 breast cancer tumor xenografts harboring PI3K mutations (E545K) and dosed by PO (oral) administration with vehicle (0.5% methylcelluose/0.2% Tween-80), fulvestrant, GDC-0032, and the combination of fulvestrant and GDC-0032. GDC-0032 was dosed orally (PO) and daily (qd) for 21 days with 5, 10 and 15 mg/kg. Fulvestrant was dosed subcutaneously with 5 mg of drug once a week (qw) for 3 weeks. Compared to monotherapy, 5 and 10 mg/kg GDC-0032 enhanced the anti-tumor activity of fulvestrant during the treatment period and for an additional 20 days after dosing ended. Compared to GDC-0032 single agent activity, combination 15 mg/kg of GDC-0032 and fulvestrant resulted in sustained tumor growth inhibition after the treatment period.

Figure 31:
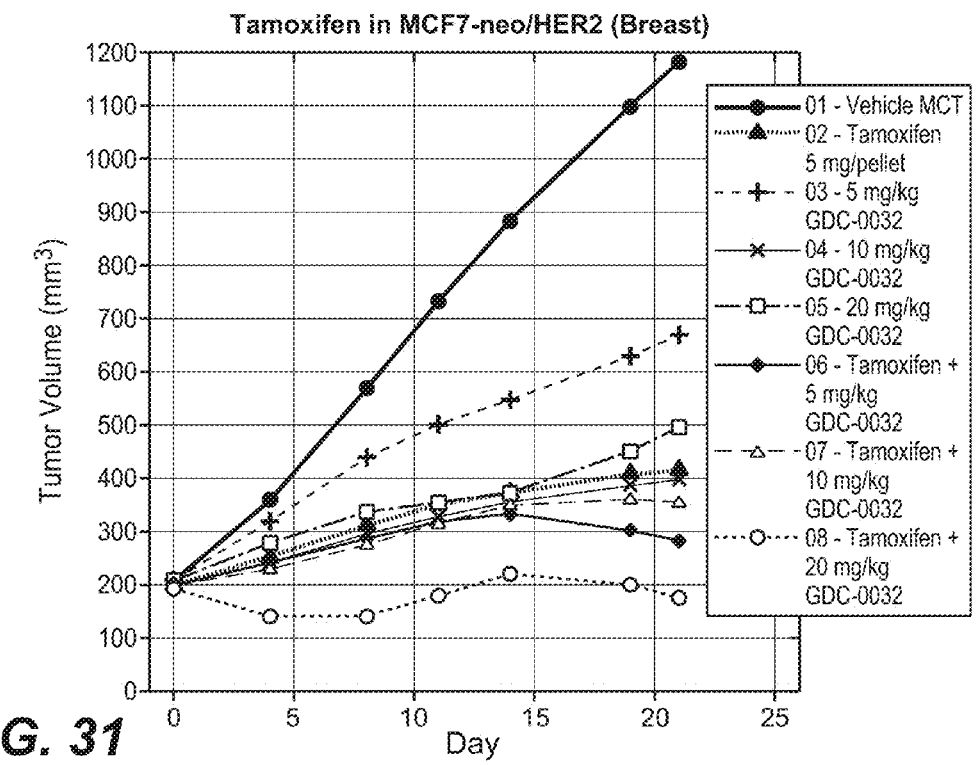
FIG. 31 shows the fitted tumor volume change over 21 days in cohorts of 8 to 10 immunocompromised mice bearing MCF-7 neo/HER2 (ER+, PIK3CA (PI3Kα) mutation (E545K), HER2+) breast cancer tumor xenografts dosed with tamoxifen, GDC-0032, and the combination of tamoxifen and GDC-0032.

FIG. 31 shows the mean tumor volume change over 20+ days in cohorts of immunocompromised (nude) mice bearing MCF-7 neo/HER2 breast cancer tumor xenografts harboring PI3K mutations (E545K) dosed by PO (oral) administration with vehicle (MCT; 0.5% methylcellulose/0.2% Tween 80), tamoxifen, GDC-0032, and the combination of tamoxifen and GDC-0032. GDC-0032 was dosed orally (PO) and daily for 21 days with 5, 10 and 20 mg/kg. Tamoxifen was administered through 5 mg pellets implanted sub-cutaneous in mice. Compared to monotherapy, 20 mg/kg of GDC-0032 enhanced the anti-tumor activity of tamoxifen and resulted in tumor regressions.

Figure 32:
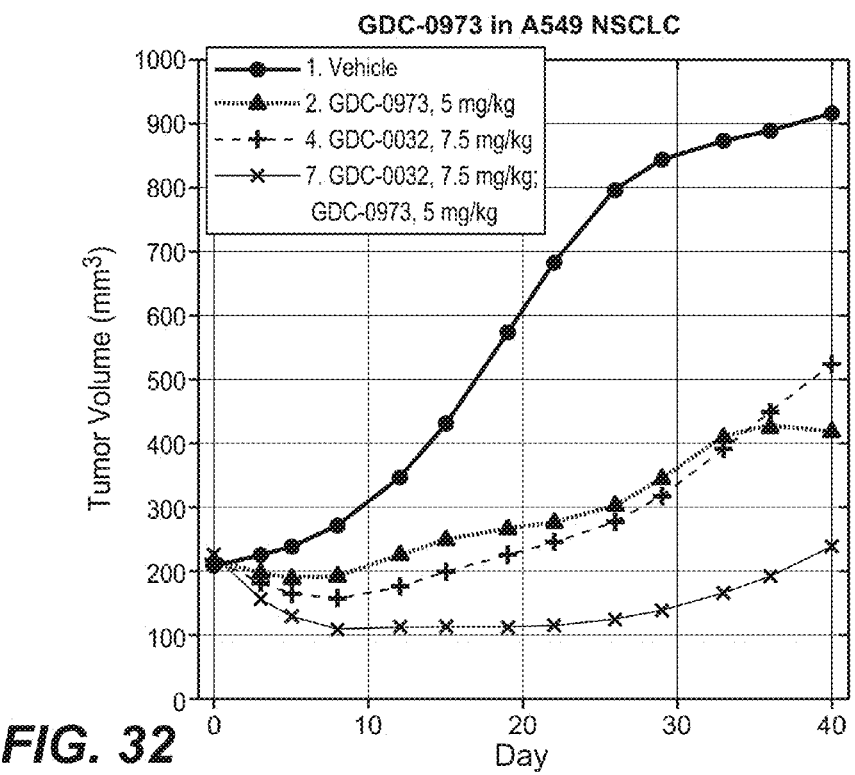
FIG. 32 shows the fitted tumor volume change over 40 days in cohorts of 8 to 10 immunocompromised mice bearing A549 non-small cell lung cancer (NSCLC) tumor xenografts dosed once daily for 21 days by PO (oral) administration with GDC-0973, GDC-0032, and the combination of GDC-0973 and GDC-0032.

FIG. 32 shows the mean tumor volume change over 40 days in cohorts of immunocompromised (nude) mice bearing A549 mutant non-small cell lung cancer (NSCLC) tumor xenografts dosed by PO (oral) administration with vehicle (0.5% methylcelluose/0.2% Tween 80), GDC-0973, GDC-0032, and the combination of GDC-0973 and GDC-0032. GDC-0032 and GDC-0973 were dosed daily for 21 days with 7.5 and 5.0 mg/kg respectively. The combination of GDC-0032 and GDC-0973 resulted in increased tumor regressions during the treatment period. The combination effects of both drugs was durable as sustained anti-tumor activity was observed for additional 19 days after treatment ended.

Figure 33:
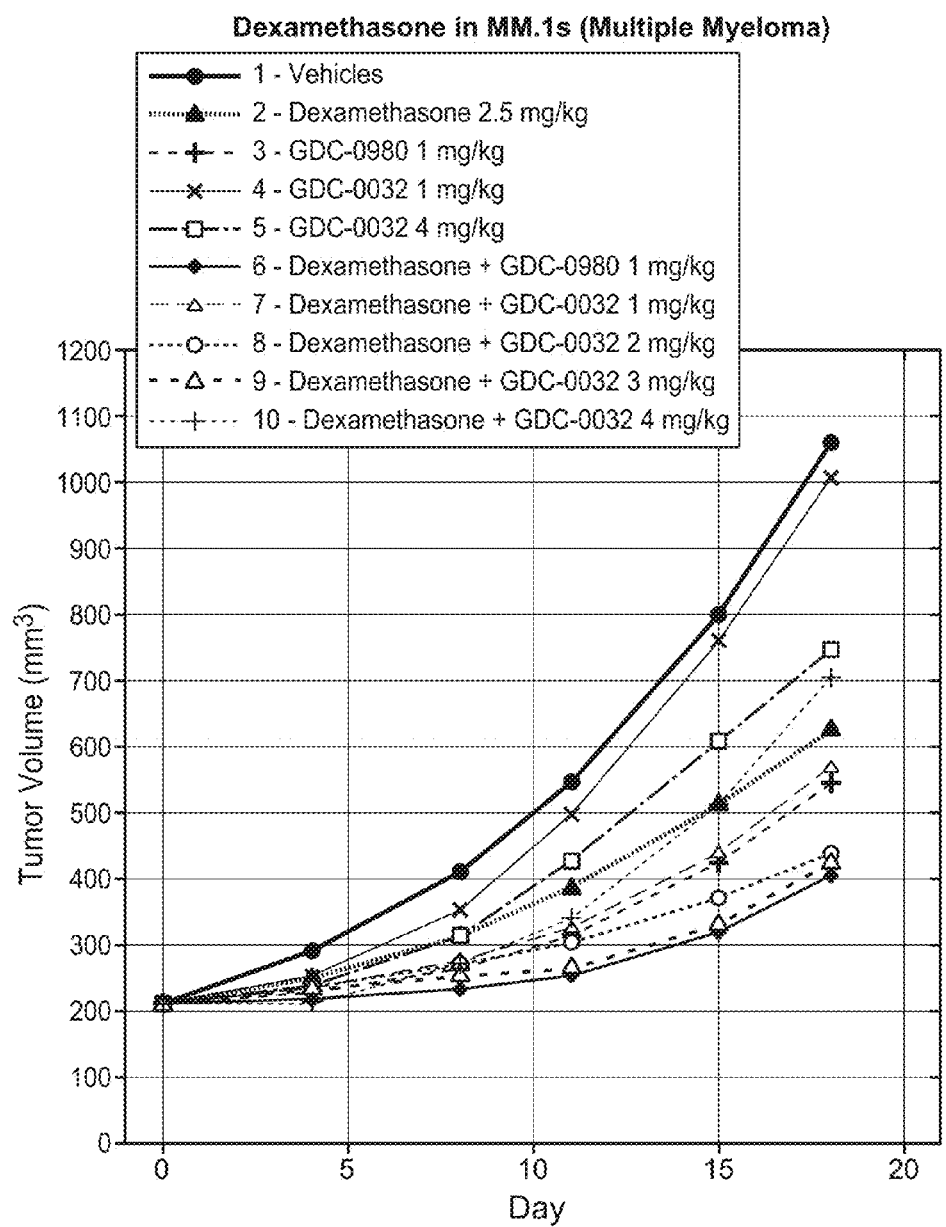
FIG. 33 shows the fitted tumor volume change over 18 days in cohorts of 8 to 10 immunocompromised mice with MM.1s multiple myeloma tumor xenografts dosed with dexamethasone, GDC-0980, GDC-0032, the combination of dexamethasone and GDC-0980, and the combination of dexamethasone and GDC-0032.

FIG. 33 shows the mean tumor volume change over 15+ days in cohorts of immunocompromised (SCID beige) mice bearing MM.1s multiple myeloma tumor xenografts dosed by administration with vehicles, dexamethasone, GDC-0980, GDC-0032, the combination of dexamethasone and GDC-0980, and the combination of dexamethasone and GDC-0032. GDC-0032 was dosed orally (PO) and daily with 1 and 4 mg/kg of drug. GDC-0980 was dose orally and daily with 1 mg/kg of drug. Compared to mono-therapy, combination of GDC-0032 at 1 and 4 mg/kg of drug enhanced the anti-tumor activity of dexamethasone (2.5 mg/kg). The anti-tumor combination effect observed with GDC-0032 and dexamethasone was comparable to the combination of GDC-0980 with dexamethasone.

Figure 34:
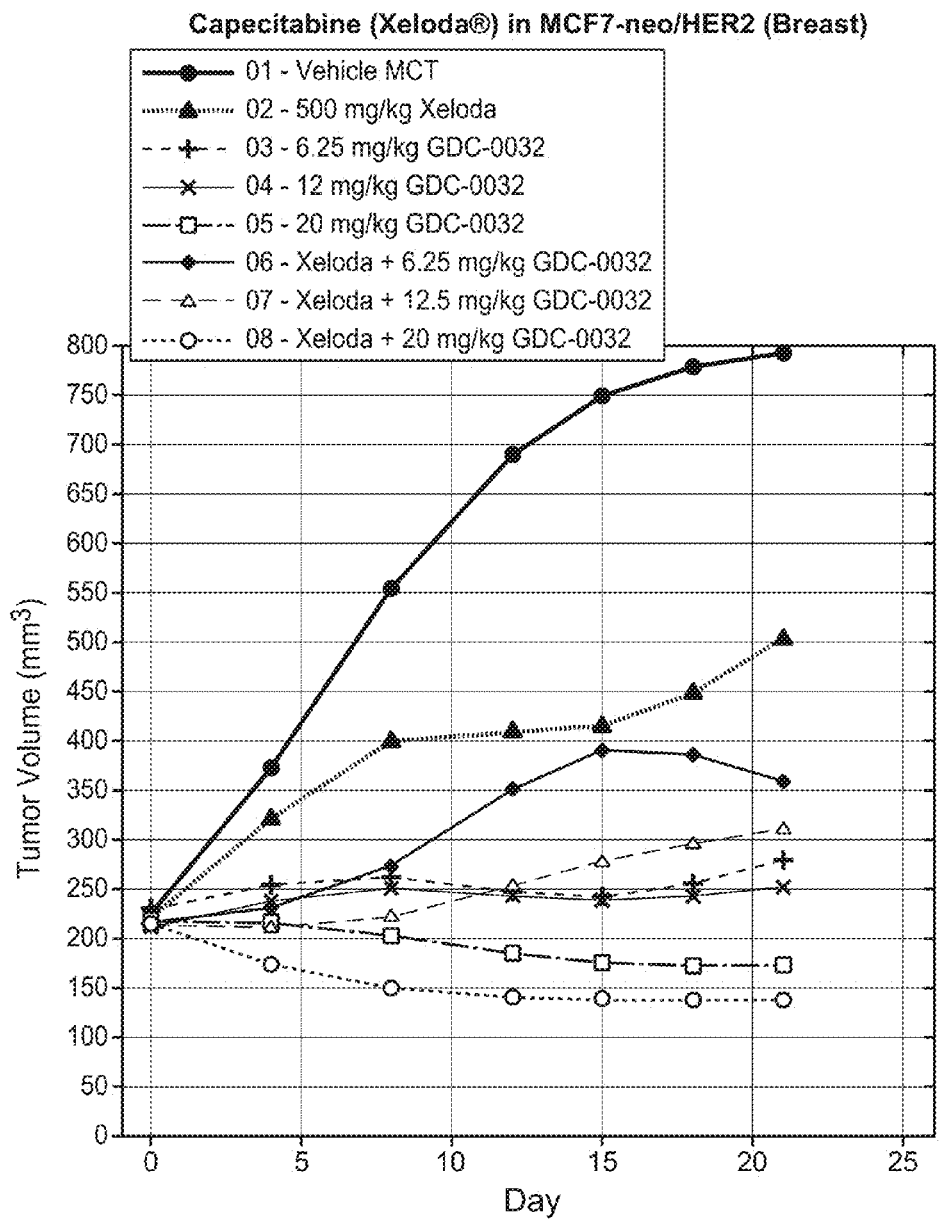
FIG. 34 shows the fitted tumor volume change over 21 days in cohorts of 8 to 10 immunocompromised mice with MCF-7 neo/HER2 breast cancer tumor xenografts dosed by PO (oral) administration with capecitabine (Xeloda®), GDC-0032, and the combination of capecitabine and GDC-0032.

FIG. 34 shows the mean tumor volume change over 21 days in cohorts of 10 mice with MCF-7 neo/HER2 breast cancer tumor xenografts dosed once daily by PO (oral) administration with capecitabine (Xeloda®), GDC-0032, and the combination of capecitabine and GDC-0032.

Figure 35:
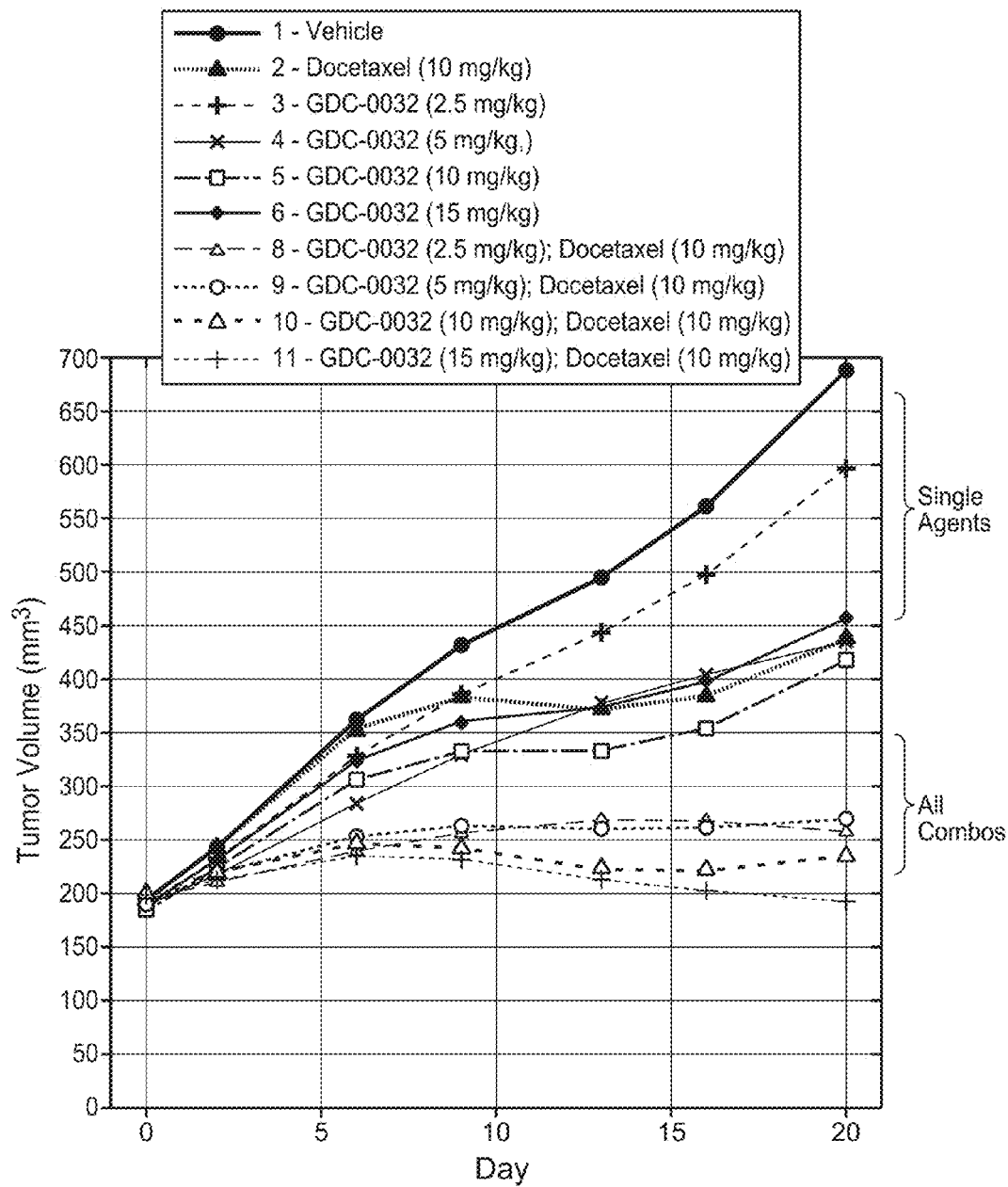
FIG. 35 shows the fitted tumor volume change over 20 days in cohorts of 8 to 10 immunocompromised mice with A549 (KRAS$^{G12S}$, PI3K$^{M772X,N996H}$) NSCLC (non-small cell lung cancer) xenografts dosed with Vehicle, docetaxel, GDC-0032, and combinations of GDC-0032+docetaxel.

FIG. 35 shows the fitted tumor volume change over 20 days in cohorts of 8 to 10 immunocompromised mice with A549 (KRAS$^{G12S}$, PI3K$^{M772X,N996H}$) NSCLC (non-small cell lung cancer) xenografts dosed with Vehicle, docetaxel, GDC-0032, and combinations of GDC-0032+docetaxel. GDC-0032 was dosed orally (PO) and daily (QD) for 21 days. DTX was dosed intravenously and weekly (QW) for 3 weeks with 10 mg/kg of drug. After dosing ended on day 21, mice were monitored for tumor regrowth for an additional 4 days. GDC-0032 enhanced the anti-tumor activity of DTX at all doses of GDC-0032 tested. Maximum combination activity was observed with 15 mg/kg of GDC-0032 plus 10 mg/kg of DTX when compared to each drug alone.

Figure 36:
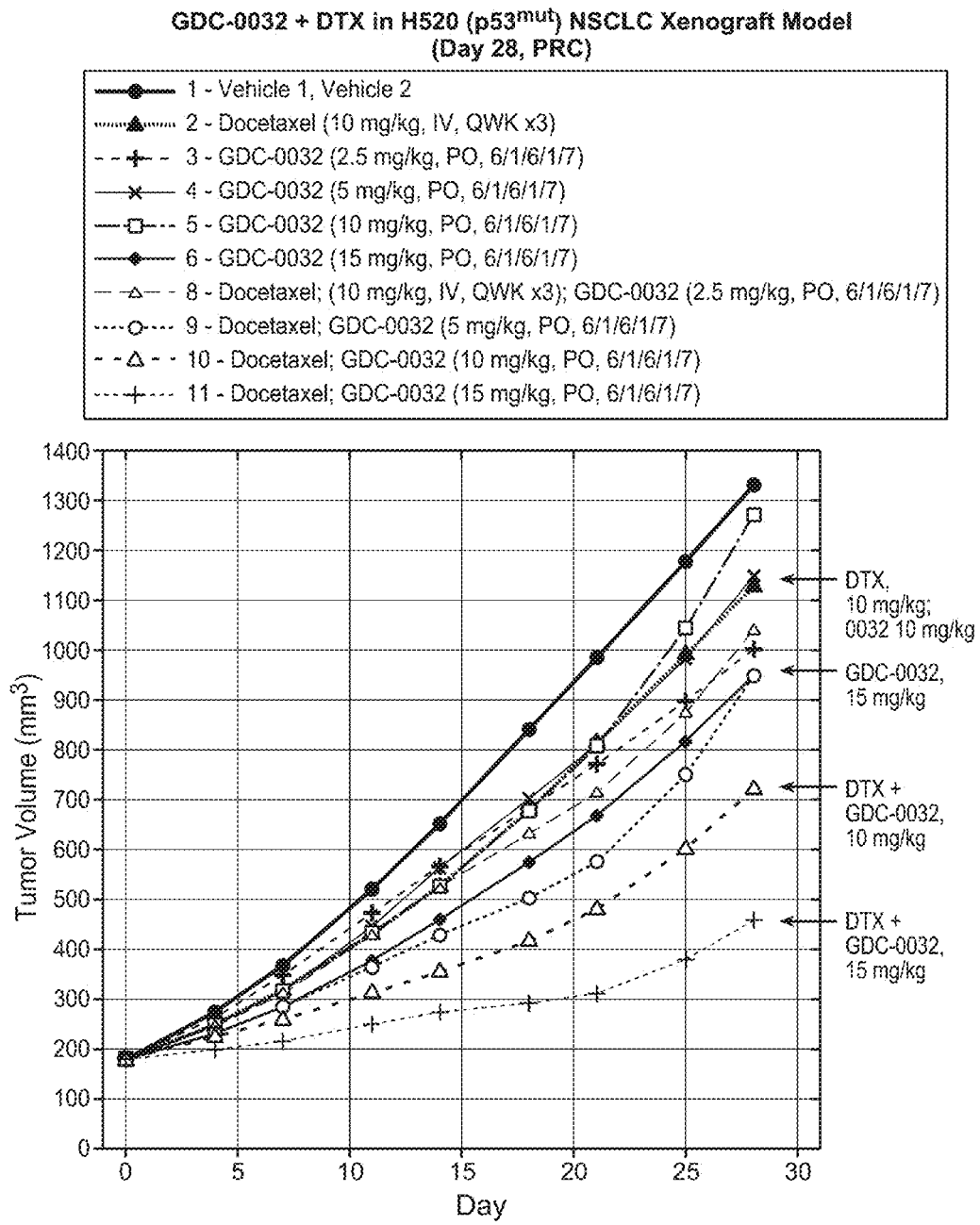
FIG. 36 shows the fitted tumor volume change over 28 days in cohorts of 8 to 10 immunocompromised mice with H520 (p53$^{mut}$) NSCLC (non-small cell lung cancer) xenografts dosed with Vehicle, docetaxel, GDC-0032, and combinations of GDC-0032+docetaxel.

FIG. 36 shows the fitted tumor volume change over 28 days in cohorts of 8 to 10 immunocompromised mice with H520 (p53$^{mut}$) NSCLC (non-small cell lung cancer) xenografts dosed with Vehicle, docetaxel, GDC-0032, and combinations of GDC-0032+docetaxel. GDC-0032 was dosed orally (PO) and daily (QD) for 21 days. DTX was dosed intravenously and weekly (QW) for 3 weeks with 10 mg/kg of drug. After dosing ended on day 21, mice were monitored for tumor regrowth for an additional 4 days. GDC-0032 enhanced the anti-tumor activity of DTX at all doses of GDC-0032 tested, except 2.5 mg/kg. Maximum combination activity was observed with 15 mg/kg of GDC-0032 plus 10 mg/kg of DTX when compared to each drug alone.

Figures 41A, 41B:
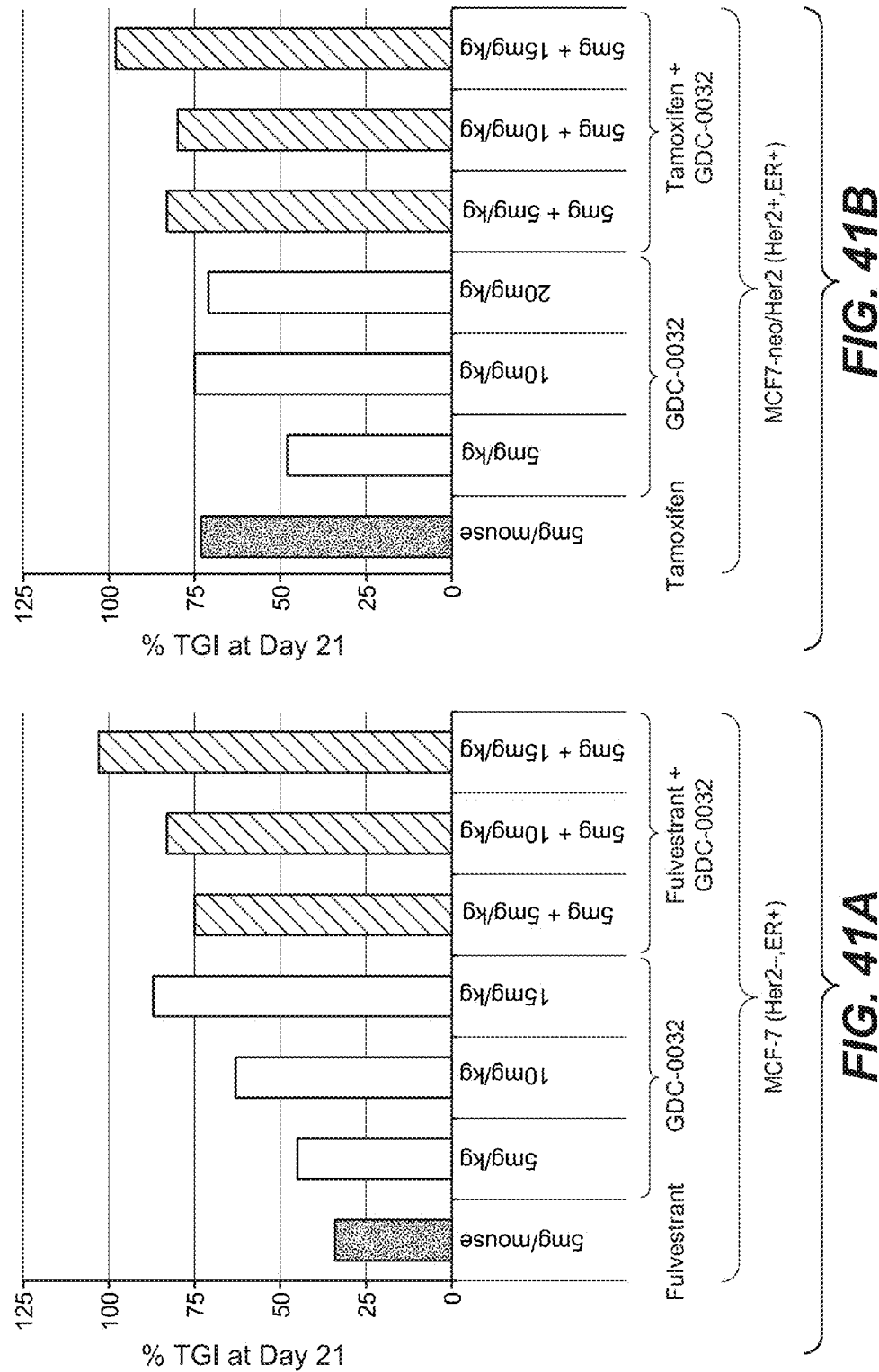
FIG. 41A shows the tumor growth inhibition (% TGI) as a percentage of vehicle control at day 21 was measured in MCF-7/ER+/HER2− mice dosed with fulvestrant and GDC-0032 alone, and in combination in MCF-7/ER+/HER2− mice.
FIG. 41B shows the tumor growth inhibition (% TGI) as a percentage of vehicle control at day 21 was measured in MCF-7/ER+/HER2− mice dosed with tamoxifen and GDC-0032 alone, and in combination in MCF-7/ER+/HER2+mice.

FIGS. 41A and 41B show increased in vivo anti-tumor activity when GDC-0032 is combined with anti-estrogen agents fulvestrant and tamoxifen. Tumor growth inhibition (% TGI) as a percentage of vehicle control at day 21 was measured in MCF-7/ER+/HER2-mice dosed with fulvestrant and GDC-0032 alone, and in combination in MCF-7/ER+/HER2-mice (FIG. 41A), and tamoxifen and GDC-0032 alone, and in combination in MCF-7/ER+/HER2+mice (FIG. 41B). Combinations of GDC-0032 with both estrogen receptor antagonists fulvestrant and tamoxifen have increased TGI compared to the single agents, demonstrating synergistic effects.

Figure 42:
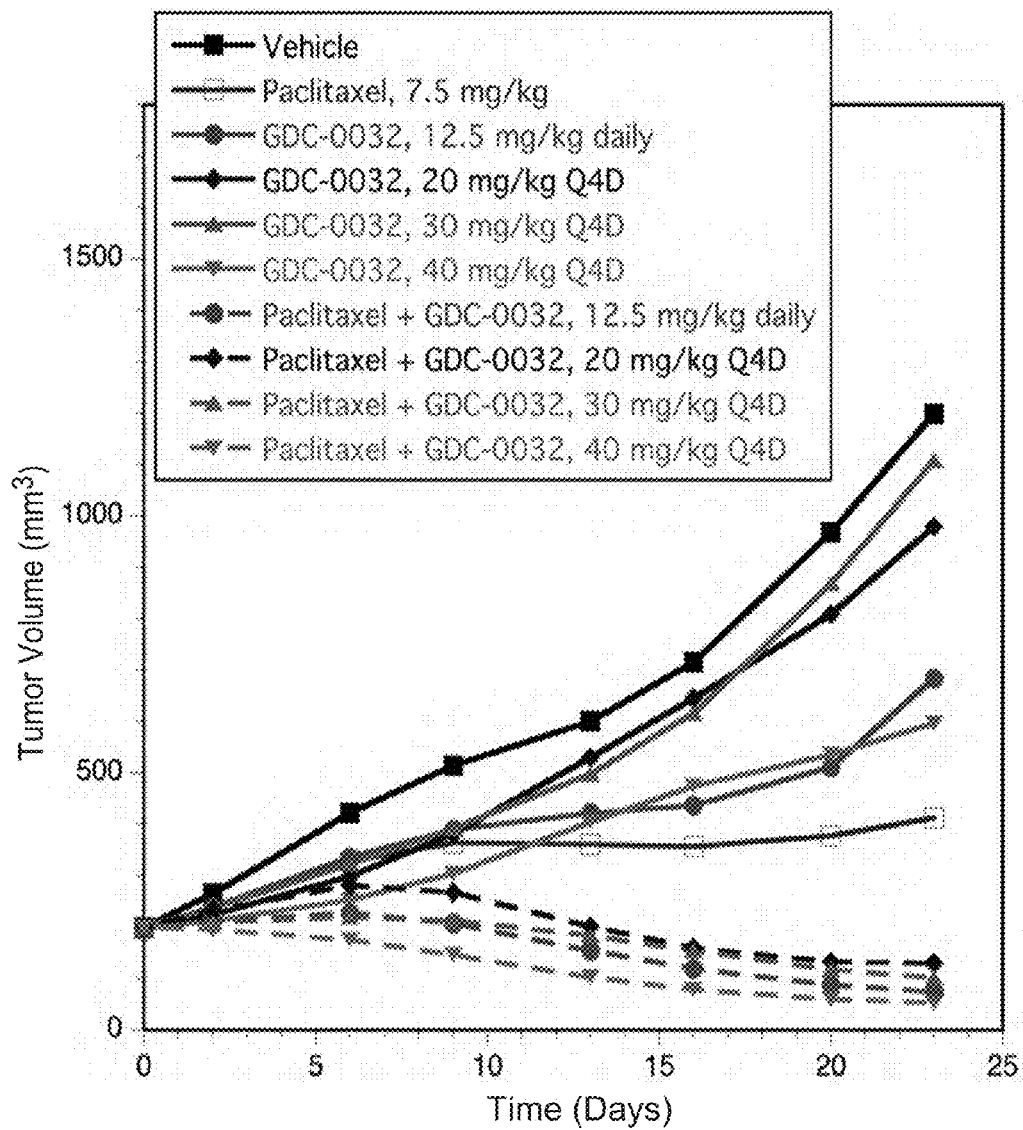
FIG. 42 shows the fitted tumor volume change over 23 days in cohorts of 12 immunocompromised mice with MCF-7 (PI3Kmut, ER+) breast xenografts dosed with vehicle, paclitaxel, GDC-0032, and combinations of GDC-0032 and paclitaxel. GDC-0032 was dosed orally (PO) and either daily (QD, with dosing holiday the day before paclitaxel dose) for 21 days or every 4 days (Q4D) for 5 cycles. Paclitaxel was dosed intravenously every 4 days for 5 cycles with 7.5 mg/kg of drug.

FIG. 42 shows the fitted tumor volume change over 23 days in cohorts of 12 immunocompromised mice with MCF-7 (PI3Kmut, ER+) breast xenografts dosed with vehicle, paclitaxel, GDC-0032, and combinations of GDC-0032+paclitaxel. GDC-0032 was dosed orally (PO) and either daily (QD, with dosing holiday the day before paclitaxel dose) for 21 days or every 4 days (Q4D) for 5 cycles. Paclitaxel was dosed intravenously every 4 days for 5 cycles with 7.5 mg/kg of drug. Both regimens of GDC-0032 (QD and Q4D) enhanced the anti-tumor activity of the combination. Maximum combination activity was observed with 40 mg/kg of GDC-0032 plus paclitaxel when compared to each drug.

Figure 43:
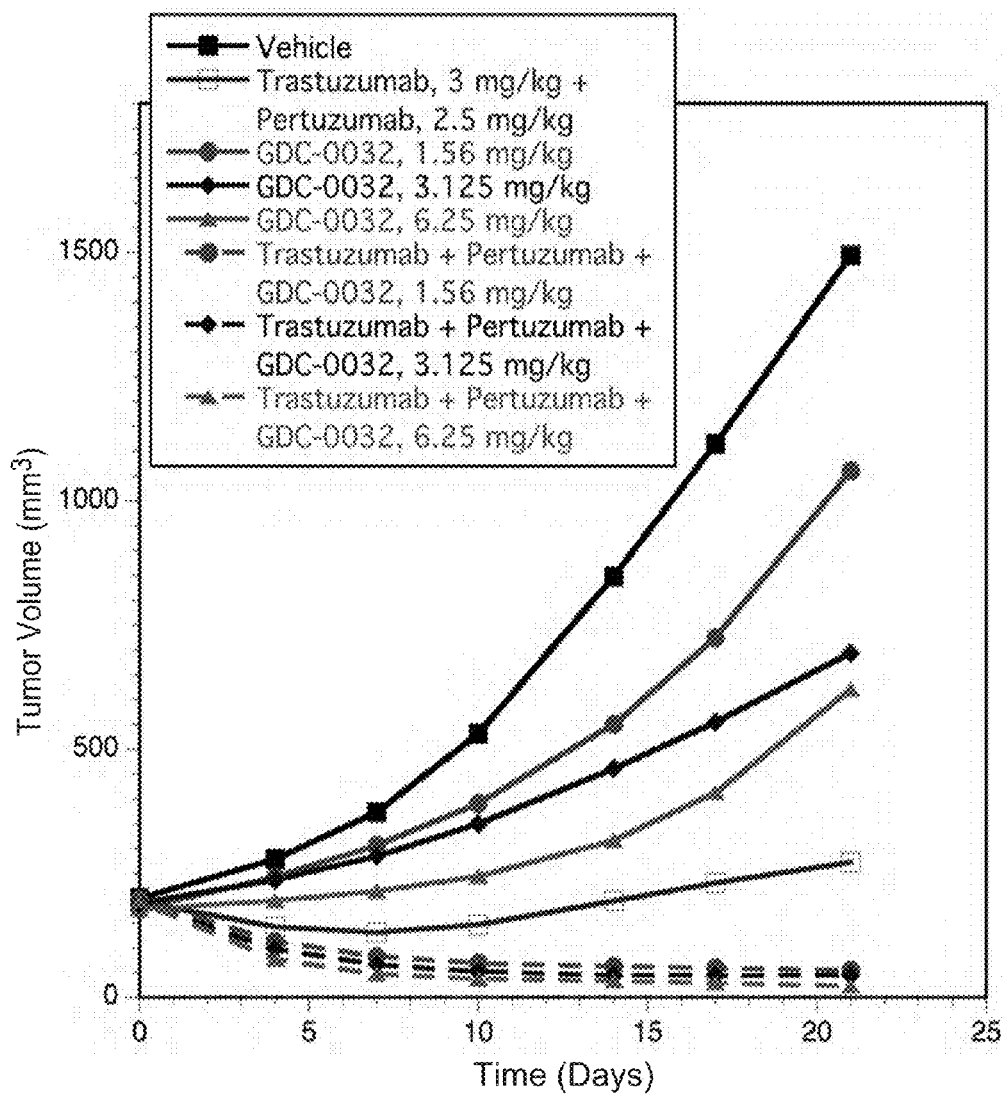
FIG. 43 shows the fitted tumor volume change over 21 days in cohorts of 8 to 10 immunocompromised mice with KPL-4 (PI3Kmut, Her2+) breast xenografts dosed with vehicle, trastuzumab, pertuzumab, GDC-0032, and triple combinations of GDC-0032 plus trastuzumab and pertuzumab. GDC-0032 was dosed orally (PO) and daily (QD) for 21 days. Trastuzumab was dosed intraperitoneally once week for 3 weeks with 3 mg/kg of drug, pertuzumab was dosed intraperitoneally once week for 3 weeks with 2.5 mg/kg of drug.

FIG. 43 shows the fitted tumor volume change over 21 days in cohorts of 8 to 10 immunocompromised mice with KPL-4 (PI3Kmut, Her2+) breast xenografts dosed with vehicle, trastuzumab, pertuzumab, GDC-0032, and triple combinations of GDC-0032 plus trastuzumab and pertuzumab, GDC-0032 was dosed orally (PO) and daily (QD) for 21 days. Trastuzumab was dosed intraperitoneally once week for 3 weeks with 3 mg/kg of drug, pertuzumab was dosed intraperitoneally once week for 3 weeks with 2.5 mg/kg of drug. GDC-0032 enhanced the anti-tumor activity of the combination at all doses of GDC-0032 tested. Maximum combination activity was observed with 1.56-6.25 mg/kg of GDC-0032 plus trastuzumab and pertuzumab when compared to each drug alone or the combination without GDC-0032.

FIG. 44 shows the fitted tumor volume change over 22 days in cohorts of 10 immunocompromised mice with H292 (KRASmut) NSCLC (non-small cell lung cancer) xenografts dosed with vehicle, paclitaxel, carboplatin, B20-4.1.1 Anti-mouse VEGF antibody (Bagri et al (2010) Clin. Cancer Res. 16:3887; Shrimali et al (2010) Cancer Res. 70(15):6171-6180), GDC-0032, and triple and quadruple combinations of GDC-0032+paclitaxel (PTX), carboplatin+/−B20-4.1.1 anti-VEGF. B20-4.1.1 is a bevacizumab (AVASTIN®, Genentech Inc.) surrogate (Liang et al (2006) Jour. Biol. Chem. 281:951-961). GDC-0032 was dosed orally (PO) and daily (QD) for 21 days. Paclitaxel was dosed intravenously on day 1 with 10 mg/kg of drug, carboplatin was dosed intraperitoneally on day 1 with 80 mg/kg of drug, and anti-VEGF was dosed intraperitoneally twice a week for 3 weeks with 5 mg/kg of drug. GDC-0032 enhanced the anti-tumor activity of the combination at all doses of GDC-0032 tested. Maximum combination activity was observed with 5 mg/kg of GDC-0032 plus paclitaxel (PTX), carboplatin and anti-VEGF when compared to each drug alone or the combination without GDC-0032.

Pharmaceutical Compositions and Formulations

Pharmaceutical compositions or formulations of the present invention include combinations of GDC-0032, a chemotherapeutic agent, and one or more pharmaceutically acceptable carrier, glidant, diluent, or excipient.

GDC-0032 and chemotherapeutic agents of the present invention may exist in unsolvated as well as solvated forms with pharmaceutically acceptable solvents such as water, ethanol, and the like, and it is intended that the invention embrace both solvated and unsolvated forms.

The compounds of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Pharmaceutical compositions encompass both the bulk composition and individual dosage units comprised of more than one (e.g., two) pharmaceutically active agents including GDC-0032 and a chemotherapeutic agent selected from the lists of the additional agents described herein, along with any pharmaceutically inactive excipients, diluents, carriers, or glidants. The bulk composition and each individual dosage unit can contain fixed amounts of the aforesaid pharmaceutically active agents. The bulk composition is material that has not yet been formed into individual dosage units. An illustrative dosage unit is an oral dosage unit such as tablets, pills, capsules, and the like. Similarly, the methods of treating a patient by administering a pharmaceutical composition is also intended to encompass the administration of the bulk composition and individual dosage units.

Pharmaceutical compositions also embrace isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^2$H, $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Certain isotopically-labeled compounds of the present invention (e.g., those labeled with $^3$H and $^{14}$C) are useful in compound and/or substrate tissue distribution assays. Tritiated ($^3$H) and carbon-14 ($^{14}$C) isotopes are useful for their ease of preparation and detectability. Further, substitution with heavier isotopes such as deuterium (2H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C and $^{18}$F are useful for positron emission tomography (PET) studies to examine substrate receptor occupancy. Isotopically labeled compounds of the present invention can generally be prepared by following procedures analogous to those disclosed in the Examples herein below, by substituting an isotopically labeled reagent for a non-isotopically labeled reagent.

GDC-0032 and chemotherapeutic agents are formulated in accordance with standard pharmaceutical practice for use in a therapeutic combination for therapeutic treatment (including prophylactic treatment) of hyperproliferative disorders in mammals including humans. The invention provides a pharmaceutical composition comprising GDC-0032 in association with one or more pharmaceutically acceptable carrier, glidant, diluent, additive, or excipient.

Suitable carriers, diluents, additives, and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), dimethylsulfoxide (DMSO), cremophor (e.g. CREMOPHOR EL®, BASF), and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, GDC-0032 having the desired degree of purity may optionally be mixed with pharmaceutically acceptable diluents, carriers, excipients or stabilizers (Remington's Pharmaceutical Sciences (1995) 18th edition, Mack Publ. Co., Easton, Pa.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8.

The pharmaceutical formulation is preferably sterile. In particular, formulations to be used for in vivo administration must be sterile. Such sterilization is readily accomplished by filtration through sterile filtration membranes.

The pharmaceutical formulation ordinarily can be stored as a solid composition, a lyophilized formulation or as an aqueous solution.

The pharmaceutical formulations of the invention will be dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

The initial pharmaceutically effective amount of GDC-0032 administered orally or parenterally per dose will be in the range of about 0.01-1000 mg/kg, namely about 0.1 to 20 mg/kg of patient body weight per day, with the typical initial range of compound used being 0.3 to 15 mg/kg/day. The dose of GDC-0032 and the dose of the chemotherapeutic agent to be administered may range for each from about 1 mg to about 1000 mg per unit dosage form, or from about 10 mg to about 100 mg per unit dosage form. The doses of GDC-0032 compound and the chemotherapeutic agent may be administered in a ratio of about 1:50 to about 50:1 by weight, or in a ratio of about 1:10 to about 10:1 by weight.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, CREMOPHOR EL®, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences 18th edition, (1995) Mack Publ. Co., Easton, Pa.

Sustained-release preparations of GDC-0032 and chemotherapeutic compounds may be prepared. Suitable examples of sustained-release preparations include semipermeable matrices of solid hydrophobic polymers containing GDC-0032, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D (−) 3-hydroxybutyric acid.

The pharmaceutical formulations include those suitable for the administration routes detailed herein. The formulations may conveniently be presented in unit dosage form and may be prepared by any of the methods well known in the art of pharmacy. Techniques and formulations generally are found in Remington's Pharmaceutical Sciences 18$^{th}$ Ed. (1995) Mack Publishing Co., Easton, Pa. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of GDC-0032 and/or chemotherapeutic agent suitable for oral administration may be prepared as discrete units such as pills, hard or soft e.g., gelatin capsules, cachets, troches, lozenges, aqueous or oil suspensions, dispersible powders or granules, emulsions, syrups or elixirs each containing a predetermined amount of GDC-0032 and/or a chemotherapeutic agent. The amount of GDC-0032 and the amount of chemotherapeutic agent may be formulated in a pill, capsule, solution or suspension as a combined formulation. Alternatively, GDC-0032 and the chemotherapeutic agent may be formulated separately in a pill, capsule, solution or suspension for administration by alternation.

Formulations may be prepared according to any method known to the art for the manufacture of pharmaceutical compositions and such compositions may contain one or more agents including sweetening agents, flavoring agents, coloring agents and preserving agents, in order to provide a palatable preparation. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablet excipients of a pharmaceutical formulation of the invention may include: Filler (or diluent) to increase the bulk volume of the powdered drug making up the tablet; Disintegrants to encourage the tablet to break down into small fragments, ideally individual drug particles, when it is ingested and promote the rapid dissolution and absorption of drug; Binder to ensure that granules and tablets can be formed with the required mechanical strength and hold a tablet together after it has been compressed, preventing it from breaking down into its component powders during packaging, shipping and routine handling; Glidant to improve the flowability of the powder making up the tablet during production; Lubricant to ensure that the tabletting powder does not adhere to the equipment used to press the tablet during manufacture. They improve the flow of the powder mixes through the presses and minimize friction and breakage as the finished tablets are ejected from the equipment; Antiadherent with function similar to that of the glidant, reducing adhesion between the powder making up the tablet and the machine that is used to punch out the shape of the tablet during manufacture; Flavor incorporated into tablets to give them a more pleasant taste or to mask an unpleasant one, and Colorant to aid identification and patient compliance.

Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

The aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner, including a mixture of at least one emulsifier with a fat or an oil, or with both a fat and an oil. Preferably, a hydrophilic emulsifier is included together with a lipophilic emulsifier which acts as a stabilizer. Together, the emulsifier(s) with or without stabilizer(s) make up an emulsifying wax, and the wax together with the oil and fat comprise an emulsifying ointment base which forms the oily dispersed phase of cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of the pharmaceutical formulations of the invention contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Pharmaceutical compositions may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may be a solution or a suspension in a non-toxic parenterally acceptable diluent or solvent, such as a solution in 1,3-butanediol or prepared from a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

GDC-0032 may be employed in combination with certain chemotherapeutic agents for the treatment of a hyperproliferative disorder, including solid tumor or hematopoietic malignancy, along with pre-malignant and non-neoplastic or non-malignant hyperproliferative disorders. In certain embodiments, GDC-0032 is combined with a chemotherapeutic agent in a single formulation as a single tablet, pill, capsule, or solution for simultaneous administration of the combination. In other embodiments, GDC-0032 and the chemotherapeutic agent are administered according to a dosage regimen or course of therapy in separate formulations as separate tablets, pills, capsules, or solutions for sequential administration of GDC-0032 and the chemotherapeutic agent selected from 5-FU, docetaxel, eribulin, gemcitabine, GDC-0973, GDC-0623, paclitaxel, tamoxifen, fulvestrant, dexamethasone, pertuzumab, trastuzumab emtansine, trastuzumab and letrozole. The chemotherapeutic agent has anti-hyperproliferative properties or is useful for treating the hyperproliferative disorder. The combination of GDC-0032 and chemotherapeutic agent may have synergistic properties. The chemotherapeutic agent of the pharmaceutical combination formulation or dosing regimen preferably has complementary activities to GDC-0032, and such that they do not adversely affect each other. Such compounds of the therapeutic combination may be administered in amounts that are effective for the purpose intended. In one embodiment, a pharmaceutical formulation of this invention comprises GDC-0032 and a chemotherapeutic agent such as described herein. In another embodiment, the therapeutic combination is administered by a dosing regimen wherein the therapeutically effective amount of GDC-0032 is administered in a range from twice daily to once every three weeks (q3wk), and the therapeutically effective amount of the chemotherapeutic agent is administered separately, in alternation, in a range from twice daily to once every three weeks.

Therapeutic combinations of the invention include a GDC-0032, and a chemotherapeutic agent selected from 5-FU, docetaxel, eribulin, gemcitabine, GDC-0973, GDC-0623, paclitaxel, tamoxifen, fulvestrant, dexamethasone, pertuzumab, trastuzumab emtansine, trastuzumab and letrozole, for separate, simultaneous or sequential use in the treatment of a hyperproliferative disorder.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments, such as to increase the therapeutic index or mitigate toxicity or other side-effects or consequences.

In a particular embodiment of anti-cancer therapy, the therapeutic combination may be combined with surgical therapy and radiotherapy, as adjuvant therapy. Combination therapies according to the present invention include the administration of GDC-0032 and one or more other cancer treatment methods or modalities. The amounts of GDC-0032 and the chemotherapeutic agent(s) and the relative timings of administration will be selected in order to achieve the desired combined therapeutic effect.

Administration of Pharmaceutical Compositions

The therapeutic combinations of the invention may be administered by any route appropriate to the condition to be treated. Suitable routes include oral, parenteral (including subcutaneous, intramuscular, intravenous, intraarterial, inhalation, intradermal, intrathecal, epidural, and infusion techniques), transdermal, rectal, nasal, topical (including buccal and sublingual), vaginal, intraperitoneal, intrapulmonary and intranasal. Topical administration can also involve the use of transdermal administration such as transdermal patches or iontophoresis devices. Formulation of drugs is discussed in Remington's Pharmaceutical Sciences, 18$^{th}$ Ed., (1995) Mack Publishing Co., Easton, Pa. Other examples of drug formulations can be found in Liberman, H. A. and Lachman, L., Eds., Pharmaceutical Dosage Forms, Marcel Decker, Vol 3, 2$^{nd}$ Ed., New York, N.Y. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier, glidant, or excipient. Where the compound is administered parenterally, it may be formulated with a pharmaceutically acceptable parenteral vehicle or diluent, and in a unit dosage injectable form, as detailed below.

A dose to treat human patients may range from about 1 mg to about 1000 mg of GDC-0032, such as about 5 mg to about 20 mg of the compound. A dose may be administered once a day (QD), twice per day (BID), or more frequently, depending on the pharmacokinetic (PK) and pharmacodynamic (PD) properties, including absorption, distribution, metabolism, and excretion of the particular compound. In addition, toxicity factors may influence the dosage and administration dosing regimen. When administered orally, the pill, capsule, or tablet may be ingested twice daily, daily or less frequently such as weekly or once every two or three weeks for a specified period of time. The regimen may be repeated for a number of cycles of therapy.

Methods of Treatment

The methods of the invention include:
- methods of diagnosis based on the identification of a biomarker;
- methods of determining whether a patient will respond to GDC-0032, or a combination of GDC-0032 and a chemotherapeutic agent;
- methods of optimizing therapeutic efficacy by monitoring clearance of GDC-0032, or a combination of GDC-0032 and a chemotherapeutic agent;
- methods of optimizing a therapeutic regime of GDC-0032, or a combination of GDC-0032 and a chemotherapeutic agent, by monitoring the development of therapeutic resistance mutations; and
- methods for identifying which patients will most benefit from treatment with GDC-0032 or a combination of GDC-0032 and a chemotherapeutic agent therapies and monitoring patients for their sensitivity and responsiveness to treatment with GDC-0032 or a combination of GDC-0032 and a chemotherapeutic agent therapies.

The methods of the invention are useful for inhibiting abnormal cell growth or treating a hyperproliferative disorder such as cancer in a mammal (e.g., human). For example, the methods are useful for diagnosing, monitoring, and treating multiple myeloma, lymphoma, leukemias, prostate cancer, breast cancer, hepatocellular carcinoma, pancreatic cancer, and/or colorectal cancer in a mammal (e.g., human).

Therapeutic combinations of: (1) GDC-0032 and (2) a chemotherapeutic agent are useful for treating diseases, conditions and/or disorders including, but not limited to, those characterized by activation of the PI3 kinase pathway. Accordingly, another aspect of this invention includes methods of treating diseases or conditions that can be treated by inhibiting lipid kinases, including PI3. In one embodiment, a method for the treatment of a solid tumor or hematopoietic malignancy comprises administering a therapeutic combination as a combined formulation or by alternation to a mammal, wherein the therapeutic combination comprises a therapeutically effective amount of GDC-0032, and a therapeutically effective amount of one or more chemotherapeutic agents selected from 5-FU, docetaxel, eribulin, gemcitabine, GDC-0973, GDC-0623, paclitaxel, tamoxifen, fulvestrant, dexamethasone, pertuzumab, trastuzumab emtansine, trastuzumab and letrozole. Therapeutic combinations of: (1) GDC-0032 and (2) a chemotherapeutic agent may be employed for the treatment of a hyperproliferative disease or disorder, including hematopoietic malignancy, tumors, cancers, and neoplastic tissue, along with pre-malignant and non-neoplastic or non-malignant hyperproliferative disorders. In one embodiment, a human patient is treated with a therapeutic combination and a pharmaceutically acceptable carrier, adjuvant, or vehicle, wherein GDC-0032, or metabolite thereof, of said therapeutic combination is present in an amount to detectably inhibit PI3 kinase activity.

Hematopoietic malignancies include non-Hodgkin's lymphoma, diffuse large hematopoietic lymphoma, follicular lymphoma, mantle cell lymphoma, chronic lymphocytic leukemia, multiple myeloma, AML, and MCL.

Another aspect of this invention provides a pharmaceutical composition or therapeutic combination for use in the treatment of the diseases or conditions described herein in a mammal, for example, a human, suffering from such disease or condition. Also provided is the use of a pharmaceutical composition in the preparation of a medicament for the treatment of the diseases and conditions described herein in a warm-blooded animal, such as a mammal, for example a human, suffering from such disorder.

Articles of Manufacture

In another embodiment of the invention, an article of manufacture, or "kit", containing GDC-0032 useful for the treatment of the diseases and disorders described above is provided. In one embodiment, the kit comprises a container comprising GDC-0032. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold GDC-0032 or a formulation thereof which is effective for treating the condition and may have a sterile access port (for example, the container may be an intravenous solution bag or a vial having a stopper pierceable by a hypodermic injection needle). At least one active agent in the composition is GDC-0032. The label or package insert indicates that the composition is used for treating the condition of choice, such as cancer. In one embodiment, the label or package inserts indicates that the composition comprising a Formula I compound can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of GDC-0032 and, if present, the second pharmaceutical formulation. For example, if the kit comprises a first composition comprising GDC-0032 and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of GDC-0032, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with GDC-0032 contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Where the kit comprises GDC-0032 and a second therapeutic agent, i.e. the chemotherapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

EXAMPLES

Example 1

2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanamide (GDC-0032)

Step 1: ethyl 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanoate

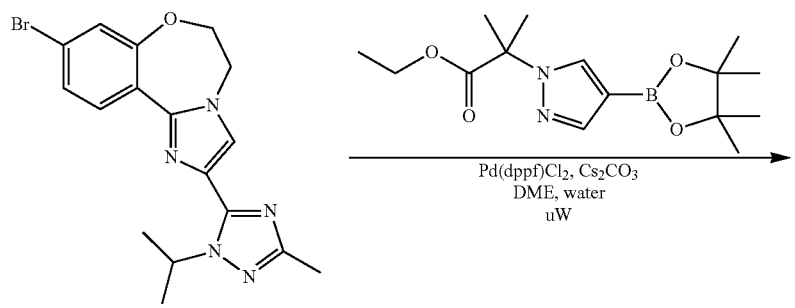

-continued

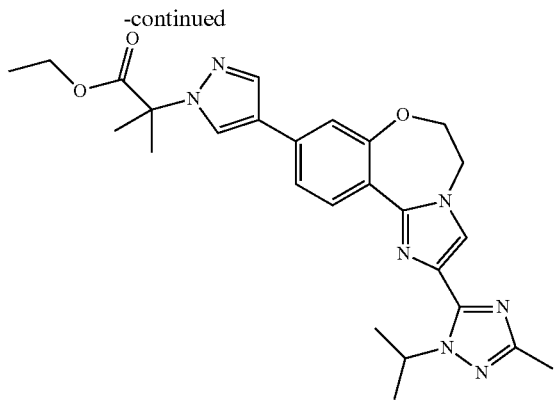

9-Bromo-2-(1-isopropyl-3-methyl-1H-1,2,4-triazol-5-yl)-5,6-dihydrobenzo[f]imidazo[1,2-d][1,4]oxazepine (500 mg, 0.001 mol) and ethyl 2-methyl-2-(4-(4,4,5,5-tetramethyl-1,3,2-dioxaborolan-2-yl)-1H-pyrazol-1-yl)propanoate (594 mg, 0.0015 mol) were reacted under microwave (uW), palladium catalyzed Suzuki coupling conditions with Pd(dppf)Cl$_2$ and Cs$_2$CO$_3$ water and dimethoxyethane to give ethyl 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanoate together with the corresponding acid. LC/MS (ESI+): m/z 490 (M+H)

Step 2: 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanoic acid

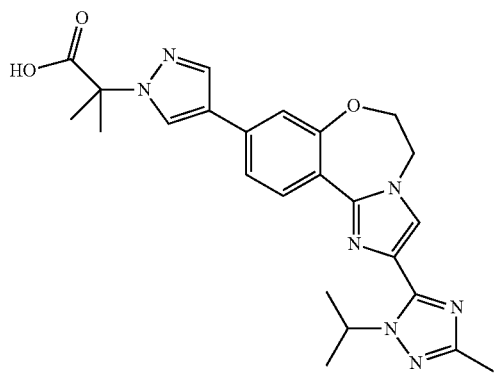 [SMILES: Cc1nc(-c2cn3c(n2)-c2ccc(-c4cnn(C(C)(C)C(=O)O)c4)cc2OCC3)n(C(C)C)n1]

Ethyl 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanoate (250 mg, 0.5 mmol) was treated with 1 M of lithium hydroxide in water (2 mL) and methanol (1 mL). The reaction was stirred at room temperature for 12 h. Acidified by 10% aqueous citric acid to pH 5 and extracted with EtOAc twice. The combined organic layers were washed with brine, dried and concentrated. The resultant 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanoic acid was used as is with no further purification steps. LC/MS (ESI+): m/z 462 (M+H). $^1$H NMR (500 MHz, DMSO) δ 8.44 (s, 1H), 8.36 (d, J=8.4, 1H), 7.97 (s, 1H), 7.86 (s, 1H), 7.44 (dd, J=8.4, 1.7, 1H), 7.35 (d, J=1.7, 1H), 5.82 (dt, J=13.1, 6.6, 1H), 4.52 (s, 4H), 2.25 (s, 3H), 1.78 (s, 6H), 1.45 (t, J=13.9, 6H)

Step 3: 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanoic acid (90 mg, 0.2 mmol) was dissolved in DMF (2 mL) and treated with NH$_4$Cl (40 mg, 0.8 mmol), DIPEA (0.3 mL, 2 mmol) followed by N,N,N',N'-tetramethyl-O-(7-azabenzotriazol-1-yl)uronium hexafluorophosphate (HATU, 100 mg, 0.4 mmol). The mixture was stirred at room temperature for 2 hours. Saturated sodium bicarbonate was added, and the mixture was extracted with EtOAc. The combined organics were dried over sodium sulfate and concentrated. The crude was purified by 10% MeOH/EtOAc following by trituration with minimal EtOAc to provide 74 mg (82% yield) of 2-(4-(2-(1-isopropyl-3-methyl-1H-1,2,4-triazol-5-yl)-5,6-dihydrobenzo[f]imidazo[1,2-d][1,4]oxazepin-9-yl)-1H-pyrazol-1-yl)-2-methylpropanamide (GDC-0032, CAS Reg. No. 1282512-48-4). LC/MS (ESI+): m/z 463(M+H). $^1$H NMR (500 MHz, DMSO) δ 8.44-8.26 (m, 2H), 8.01 (s, 1H), 7.86 (s, 1H), 7.44 (dd, J=8.4, 1.8, 1H), 7.35 (d, J=1.7, 1H), 7.15 (s, 1H), 6.79 (s, 1H), 5.82 (dt, J=13.3, 6.6, 1H), 4.52 (s, 4H), 2.25 (s, 3H), 1.75 (s, 6H), 1.47 (d, J=6.6, 6H)

Example 2 p110α (Alpha) PI3K Binding Assay

Binding Assays Initial polarization experiments were performed on an Analyst HT 96-384 (Molecular Devices Corp, Sunnyvale, Calif.). Samples for fluorescence polarization affinity measurements were prepared by addition of 1:3 serial dilutions of p110alpha PI3K (Upstate Cell Signaling Solutions, Charlottesville, Va.) starting at a final concentration of 20 ug/mL in polarization buffer (10 mM Tris pH 7.5, 50 mM NaCl, 4 mM MgCl$_2$, 0.05% Chaps, and 1 mM DTT) to 10 mM PIP$_2$ (Echelon-Inc., Salt Lake City, Utah.) final concentration. After an incubation time of 30 minutes at room temperature, the reactions were stopped by the addition of GRP-1 and PIP3-TAMRA probe (Echelon-Inc., Salt Lake City, Utah.) 100 nM and 5 nM final concentrations respectively. Read with standard cut-off filters for the rhodamine fluorophore (λex=530 nm; λem=590 nm) in 384-well black low volume Proxiplates® (PerkinElmer, Wellesley, Mass.) Fluorescence polarization values were plotted as a function of the protein concentration. EC$_{50}$ values were obtained by fitting the data to a four-parameter equation using KaleidaGraph® software (Synergy software, Reading, Pa.). This experiment also establishes the appropriate protein concentration to use in subsequent competition experiments with inhibitors.

Inhibitor $IC_{50}$ values were determined by addition of the 0.04 mg/mL p110alpha PI3K (final concentration) combined with $PIP_2$ (10 mM final concentration) to wells containing 1:3 serial dilutions of the antagonists in a final concentration of 25 mM ATP (Cell Signaling Technology, Inc., Danvers, Mass.) in the polarization buffer. After an incubation time of 30 minutes at room temperature, the reactions were stopped by the addition of GRP-1 and PIP3-TAMRA probe (Echelon-Inc., Salt Lake City, Utah.) 100 nM and 5 nM final concentrations respectively. Read with standard cut-off filters for the rhodamine fluorophore ($\lambda$ex=530 nm; $\lambda$em=590 nm) in 384-well black low volume Proxiplates® (PerkinElmer, Wellesley, Mass.) Fluorescence polarization values were plotted as a function of the antagonist concentration, and the $IC_{50}$ values were obtained by fitting the data to a 4-parameter equation in Assay Explorer software (MDL, San Ramon, Calif.).

Alternatively, inhibition of PI3K was determined in a radiometric assay using purified, recombinant enzyme and ATP at a concentration of 1 $\mu$M (micromolar). The compound was serially diluted in 100% DMSO. The kinase reaction was incubated for 1 h at room temperature, and the reaction was terminated by the addition of PBS. $IC_{50}$ values were subsequently determined using sigmoidal dose-response curve fit (variable slope).

Example 3

In Vitro Cell Proliferation Assay

Efficacy of GDC-0032 and chemotherapeutic compounds were measured by a cell proliferation assay employing the following protocol (Mendoza et al (2002) Cancer Res. 62:5485-5488).

The CellTiter-Glo® Luminescent Cell Viability Assay is a homogeneous method to determine the number of viable cells in culture based on quantitation of the ATP present, which signals the presence of metabolically active cells. The Cell-Titer-Glo® Assay is designed for use with multiwell plate formats, making it ideal for automated high-throughput screening (HTS), cell proliferation and cytotoxicity assays. The homogeneous assay procedure involves adding a single reagent (CellTiter-Glo® Reagent) directly to cells cultured in serum-supplemented medium. Cell washing, removal of medium or multiple pipetting steps are not required. The Cell Titer-Glo® Luminescent Cell Viability Assay, including reagents and protocol are commercially available (Promega Corp., Madison, Wis., Technical Bulletin TB288).

The assay assesses the ability of compounds to enter cells and inhibit cell proliferation. The assay principle is based on the determination of the number of viable cells present by quantitating the ATP present in a homogenous assay where addition of the Cell Titer-Glo® reagent results in cell lysis and generation of a luminescent signal through the luciferase reaction. The luminescent signal is proportional to the amount of ATP present.

Procedure: Day 1—Seed Cell Plates (384-well black, clear bottom, microclear, TC plates with lid from Falcon #353962), Harvest cells, Seed cells at 1000 cells per 54 µl per well into 384 well Cell Plates for 3 days assay. Cell Culture Medium: RPMI or DMEM high glucose, 10% Fetal Bovine Serum, 2 mM L-Glutamine, P/S. Incubate O/N (overnight) at 37° C., 5% $CO_2$.

Day 2—Add Drug to Cells, Compound Dilution, DMSO Plates (serial 1:2 for 9 points). Add 20 µl of compound at 10 mM in the 2nd column of 96 well plate. Perform serial 1:2 across the plate (10 µl+20 µl 100% DMSO) for a total of 9 points using Precision Media Plates 96-well conical bottom polypropylene plates from Nunc (cat.#249946) (1:50 dilution). Add 147 µl of Media into all wells. Transfer 3 µl of DMSO+compound from each well in the DMSO Plate to each corresponding well on Media Plate using Rapidplate® (Caliper, a Perkin-Elmer Co.). For 2 drug combination studies, transfer one drug 1.5 µl of DMSO+compound from each well in the DMSO Plate to each corresponding well on Media Plate using Rapidplate. Then, transfer another drug 1.5 µl to the medium plate.

Drug Addition to Cells, Cell Plate (1:10 dilution): Add 6 µl of media+compound directly to cells (54 µl of media on the cells already). Incubate 3 days at 37° C., 5% $CO_2$ in an incubator that will not be opened often.

Day 5—Develop Plates, Thaw Cell Titer Glo Buffer at room temperature: Remove Cell Plates from 37° C. and equilibrate to room temperature for about 30 minutes. Add Cell Titer-Glo® Buffer to Cell Titer-Glo® Substrate (bottle to bottle). Add 30 µl Cell Titer-Glo® Reagent (Promega cat.#G7572) to each well of cells. Place on plate shaker for about 30 minutes. Read luminescence on Analyst HT Plate Reader (half second per well).

Cell viability assays and combination assays: Cells were seeded at 1000-2000 cells/well in 384-well plates for 16 h. On day two, nine serial 1:2 compound dilutions were made in DMSO in a 96 well plate. The compounds were further diluted into growth media using a Rapidplate® robot (Zymark Corp., Hopkinton, Mass.). The diluted compounds were then added to quadruplicate wells in 384-well cell plates and incubated at 37° C. and 5% $CO_2$. After 4 days, relative numbers of viable cells were measured by luminescence using Cell Titer-Glo® (Promega) according to the manufacturer's instructions and read on a Wallac Multilabel Reader® (PerkinElmer, Foster City). EC50 values were calculated using Prism® 4.0 software (GraphPad, San Diego). Drugs in combination assays were dosed starting at 4×$EC_{50}$ concentrations. If cases where the EC50 of the drug was >2.5 µM, the highest concentration used was 10 µM. GDC-0032 and chemotherapeutic agents were added simultaneously or separated by 4 hours (one before the other) in all assays.

An additional exemplary in vitro cell proliferation assay includes the following steps:

1. An aliquot of 100 µl of cell culture containing about $10^4$ cells (see Table 3 for cell lines and tumor type) in medium was deposited in each well of a 384-well, opaque-walled plate.

2. Control wells were prepared containing medium and without cells.

3. The compound was added to the experimental wells and incubated for 3-5 days.

4. The plates were equilibrated to room temperature for approximately 30 minutes.

5. A volume of CellTiter-Glo® Reagent equal to the volume of cell culture medium present in each well was added.

6. The contents were mixed for 2 minutes on an orbital shaker to induce cell lysis.

7. The plate was incubated at room temperature for 10 minutes to stabilize the luminescence signal.

8. Luminescence was recorded and reported in graphs as RLU=relative luminescence units.

9. Analyze using the Chou and Talalay combination method and Dose-Effect Analysis with CalcuSyn® software (Biosoft, Cambridge, UK) in order to obtain a Combination Index.

Alternatively, cells were seeded at optimal density in a 96 well plate and incubated for 4 days in the presence of test compound. Alamar Blue™ was subsequently added to the assay medium, and cells were incubated for 6 h before reading at 544 nm excitation, 590 nm emission. $EC_{50}$ values were calculated using a sigmoidal dose response curve fit.

Alternatively, Proliferation/Viability was analyzed after 48 hr of drug treatment using Cell Titer-Glo® reagent (Promega Inc., Madison, Wis.). DMSO treatment was used as control in all viability assays. $IC_{50}$ values were calculated using XL fit software (IDBS, Alameda, Calif.)

The cell lines were obtained from either ATCC (American Type Culture Collection, Manassas, Va.) or DSMZ (Deutsche Sammlung von Mikroorganismen und Zellkulturen GmbH, Braunschweig, Del.). Cells were cultured in RPMI 1640 medium supplemented with 10% fetal bovine serum, 100 units/ml penicillin, 2 mM L-glutamine, and 100 mg/ml streptomycin (Life Technology, Grand Island, N.Y.) at 37° C. under 5% $CO_2$.

Example 4

In Vivo Mouse Tumor Xenograft Efficacy

Mice: Female severe combined immunodeficiency mice (Fox Chase SCID®, C.B-17/IcrHsd, Harlan) or nude mice (Taconic Farms, Harlan) were 8 to 9 weeks old and had a BW range of 15.1 to 21.4 grams on Day 0 of the study. The animals were fed ad libitum water (reverse osmosis, 1 ppm Cl) and NIH 31 Modified and Irradiated Lab Diet® consisting of 18.0% crude protein, 5.0% crude fat, and 5.0% crude fiber. The mice were housed on irradiated ALPHA-Dri® Bed-O'Cobs® Laboratory Animal Bedding in static microisolators on a 12-hour light cycle at 21-22° C. (70-72° F.) and 40-60% humidity. PRC specifically complies with the recommendations of the Guide for Care and Use of Laboratory Animals with respect to restraint, husbandry, surgical procedures, feed and fluid regulation, and veterinary care. The animal care and use program at PRC is accredited by the Association for Assessment and Accreditation of Laboratory Animal Care International (AAALAC), which assures compliance with accepted standards for the care and use of laboratory animals.

Tumor Implantation:

Xenografts were initiated with cancer cells. Cells were cultured in RPMI 1640 medium supplemented with 10% fetal bovine serum, 2 mM glutamine, 100 units/mL penicillin, 100 g/mL streptomycin sulfate and 25 g/mL gentamicin. The cells were harvested during exponential growth and resuspended in phosphate buffered saline (PBS) at a concentration of $5 \times 10^6$ or $10 \times 10^6$ cells/mL depending on the doubling time of the cell line. Tumor cells were implanted subcutaneously in the right flank, and tumor growth was monitored as the average size approached the target range of 100 to 150 mm3. Twenty-one days after tumor implantation, designated as Day 0 of the study, the mice were placed into four groups each consisting of ten mice with individual tumor volumes ranging from 75-172 mm3 and group mean tumor volumes from 120-121 mm3 (see Appendix A). Volume was calculated using the formula:

Tumor Volume $(mm^3) = (w^2 \times l)/2$, where w=width and l=length in mm of a tumor. Tumor weight may be estimated with the assumption that 1 mg is equivalent to 1 mm3 of tumor volume.

Therapeutic Agents:

GDC-0032 was supplied as a dry powder in salt form, which contained 73% active agent, and was stored at room temperature protected from light. Drug doses were prepared weekly in 0.5% methylcellulose: 0.2% Tween 80 in deionized water ("Vehicle") and stored at 4° C. The salt form containing 73% active agent was accounted for in the formulation of G-033829 doses. Doses of GDC-0032 were prepared on each day of dosing by diluting an aliquot of the stock with sterile saline (0.9% NaCl). All doses were formulated to deliver the stated mg/kg dosage in a volume of 0.2 mL per 20 grams of body weight (10 mL/kg).

Treatment:

All doses were scaled to the body weights of the individual animals and were provided by the route indicated in each of the figures.

Endpoint:

Tumor volume was measured in 2 dimensions (length and width), using Ultra Cal IV calipers (Model 54 10 111; Fred V. Fowler Company), as follows: tumor volume $(mm^3) = (length \times width^2) \times 0.5$ and analyzed using Excel version 11.2 (Microsoft Corporation). A linear mixed effect (LME) modeling approach was used to analyze the repeated measurement of tumor volumes from the same animals over time (Pinheiro J, et al. nlme: linear and nonlinear mixed effects models. R package version 3.1 92. 2009; Tan N, et al. Navitoclax enhances the efficacy of taxanes in non-small cell lung cancer models. Clin. Cancer Res. 2011; 17(6):1394-1404). This approach addresses both repeated measurements and modest dropouts due to any non-treatment-related death of animals before study end. Cubic regression splines were used to fit a nonlinear profile to the time courses of log 2 tumor volume at each dose level. These nonlinear profiles were then related to dose within the mixed model. Tumor growth inhibition as a percentage of vehicle control (% TGI) was calculated as the percentage of the area under the fitted curve (AUC) for the respective dose group per day in relation to the vehicle, using the following formula: % TGI=100×$(1-AUC_{dose}/AUC_{veh})$. Using this formula, a TGI value of 100% indicates tumor stasis, a TGI value of >1% but <100% indicates tumor growth delay, and a TGI value of >100% indicates tumor regression. Partial response (PR) for an animal was defined as a tumor regression of >50% but <100% of the starting tumor volume. Complete response (CR) was defined as 100% tumor regression (i.e., no measurable tumor) on any day during the study.

Toxicity:

Animals were weighed daily for the first five days of the study and twice weekly thereafter. Animal body weights were measured using an Adventurer Pro® AV812 scale (Ohaus Corporation). Percent weight change was calculated as follows: body weight change (%)=[(weight$_{day\ new}$−weight$_{day\ 0}$)/weight$_{day\ 0}$]×100. The mice were observed frequently for overt signs of any adverse, treatment-related side effects, and clinical signs of toxicity were recorded when observed. Acceptable toxicity is defined as a group mean body weight (BW) loss of less than 20% during the study and not more than one treatment-related (TR) death among ten treated animals. Any dosing regimen that results in greater toxicity is considered above the maximum tolerated dose (MTD). A death is classified as TR if attributable to treatment side effects as evidenced by clinical signs and/or necropsy, or may also be classified as TR if due to unknown causes during the dosing period or within 10 days of the last dose. A death is classified as NTR if there is no evidence that death was related to treatment side effects.

Although the foregoing invention has been described in some detail by way of illustration and example for purposes of clarity of understanding, the descriptions and examples should not be construed as limiting the scope of the invention.

The disclosures of all patent and scientific literature cited herein are expressly incorporated in their entirety by reference.

We claim:

1. A method for the treatment of a hyperproliferative disorder comprising administering a therapeutic combination as a combined formulation or by alternation to a mammal, wherein the therapeutic combination comprises a therapeutically effective amount of GDC-0032 having the structure:

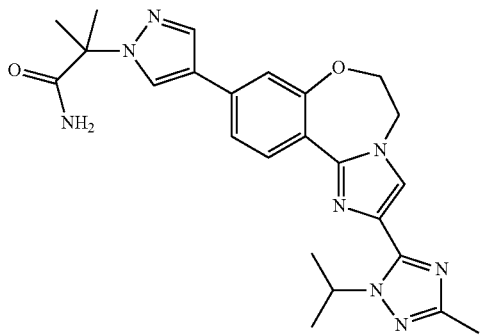 [SMILES: Cc1nc(-c2cn3c(n2)-c2ccc(-c4cnn(C(C)(C)C(N)=O)c4)cc2OCC3)n(C(C)C)n1]

and a therapeutically effective amount of fulvestrant, wherein the hyperproliferative disorder is breast cancer.

2. The method of claim 1 wherein the therapeutically effective amount of GDC-0032, and the therapeutically effective amount of fulvestrant are administered as a combined formulation.

3. The method of claim 1 wherein the therapeutically effective amount of GDC-0032, and the therapeutically effective amount of fulvestrant are administered to a mammal by alternation.

4. The method of claim 3 wherein the mammal is administered fulvestrant and subsequently administered GDC-0032.

5. The method of claim 3 wherein the therapeutic combination is administered by a dosing regimen where the therapeutically effective amount of GDC-0032 is administered in a range from twice daily to once every three weeks, and the therapeutically effective amount of fulvestrant is administered in a range from twice daily to once every three weeks.

6. The method of claim 5 wherein the dosing regimen is repeated one or more times.

7. The method of claim 1 wherein administration of the therapeutic combination results in a synergistic effect.

8. The method of claim 7 wherein administration of the therapeutic combination results in a Combination Index value of less than about 0.7.

9. The method of claim 1 wherein the breast cancer subtype is Basal or Luminal.

10. The method of claim 1 wherein GDC-0032 and fulvestrant are each administered in an amount from about 1 mg to about 1000 mg per unit dosage form.

11. The method of claim 1 wherein GDC-0032 and fulvestrant are administered in a ratio of about 1:50 to about 50:1 by weight.

* * * * *